United States Patent
Staegemann et al.

(10) Patent No.: US 10,738,059 B2
(45) Date of Patent: Aug. 11, 2020

(54) CONJUGATES OF PORPHYRINOID PHOTOSENSITIZERS AND GLYCEROL-BASED POLYMERS FOR PHOTODYNAMIC THERAPY

(71) Applicant: biolitec Unternehmensbeteiligungs II AG, Vienna (AT)

(72) Inventors: Michael Staegemann, Berlin (DE); Rainer Haag, Berlin (DE); Arno Wiehe, Berlin (DE); Susanna Graefe, Jena (DE); Burkhard Gitter, Jena (DE); Volker Albrecht, Nuthetal (DE)

(73) Assignee: Biolitec Unternehmensbeteiligungs II AG, Vienna (AT)

( * ) Notice: Subject to any disclaimer, the term of this patent is extended or adjusted under 35 U.S.C. 154(b) by 55 days.

(21) Appl. No.: 15/443,642

(22) Filed: Feb. 27, 2017

(65) Prior Publication Data

US 2017/0247384 A1 Aug. 31, 2017

Related U.S. Application Data

(60) Provisional application No. 62/300,230, filed on Feb. 26, 2016.

(51) Int. Cl.
| | | |
|---|---|---|
| A01N 43/38 | (2006.01) |
| A61K 31/40 | (2006.01) |
| C07D 487/22 | (2006.01) |
| A61K 41/00 | (2020.01) |
| C07D 403/14 | (2006.01) |
| A61K 47/60 | (2017.01) |
| C08G 65/48 | (2006.01) |

(52) U.S. Cl.
CPC ........ *C07D 487/22* (2013.01); *A61K 41/0071* (2013.01); *A61K 47/60* (2017.08); *C07D 403/14* (2013.01); *C08G 65/48* (2013.01)

(58) Field of Classification Search
None
See application file for complete search history.

(56) References Cited

U.S. PATENT DOCUMENTS

| 7,022,843 B1 | 4/2006 | MacAlpine et al. |
| 7,166,719 B2 | 1/2007 | Pandey et al. |
| 2011/0059501 A1* | 3/2011 | Davis .................. C07K 1/1077 435/183 |
| 2012/0263625 A1 | 10/2012 | Aicher et al. |

FOREIGN PATENT DOCUMENTS

| WO | 2005023220 | 3/2005 |
| WO | 2008130181 | 10/2008 |
| WO | 2010129337 | 11/2010 |
| WO | 2010129340 | 11/2010 |
| WO | 2011071968 | 6/2011 |
| WO | 2011071970 | 6/2011 |

OTHER PUBLICATIONS

"Derivative." Merriam-Webster.com. Merriam-Webster, n. d. Web. Jun. 24, 2018.*
Stefflova et al. Current Medicinal Chemistry (2007), vol. 14, pp. 2110-2125.*
Lee et al. Chemical Reviews (2013), vol. 113, pp. 5071-5109.*
B. W. Henderson Y T. J. Dougherty, Photodynamic therapy, basic principles and clinical applications, New York: Marcel Dekker, 1992.
A. P. Castano, T. N. Demidova Y M. R. Hamblin, «Mechanisms in photodynamic therapy: part one—photosensitizers, photochemistry and cellular localization,» Photodiagn. Photodyn. Ther., vol. 1, 279-293, 2004.
J. G. Moser, Photodynamic tumor therapy. 2nd and 3rd generation photosensitizers, Amsterdam: Harwood Academic Publishers, 1998.
M. S. Senge, J. C. Brandt, «Temoportin (Foscan, 5,10,15,20—Tetra(m-hydroxyphenyl)chlorin)—A Second-generation Photosensitizer,» Photochem. Photobiol., vol. 87, 1240-1296, 2011.
Y. Matsumura, H. Maeda, «A new concept for macromolecular therapeutics in cancer chemotherapy: mechanism of tumoritropic accumulation of proteins and the antitumor agent smancs,» Cancer Res., vol. 46, 6387-6392, 1986.
H. Maeda, J. Wu, T. Sawa, Y. Matsumura, K. Hori, «Tumor vascular permeability and the EPR effect in macromolecular therapeutics: a review,» J. Contr. Rel., vol. 65, 271-284, 2000.
S. Hackbarth, V. Horneffer, A. Wiehe, F. Hillenkamp, B. Röder, «Photophysical properties of pheophorbide-a-substituted diaminobutane poly-propylene-imine dendrimer,» Chem. Phys., vol. 269, 339-346, 2001.
J. S. Lindsey, I. C. Schreiman, H. C. Hsu, P. C. Kearney and A. M. Marguerettaz, «Rothemund and Adler-Longo Reactions Revisited: Synthesis of Tetraphenylporphyrins under Equilibrium Conditions,» J. Org. Chem., vol 52, 827-836, 1987.

(Continued)

*Primary Examiner* — Patrick T Lewis
(74) *Attorney, Agent, or Firm* — Bolesh J. Skutnik; BJ Associates

(57) ABSTRACT

Biologically active compounds that can be used as photosensitizers for diagnostic and therapeutic applications, particularly for PDT of cancer, infections and other hyperproliferative diseases, fluorescence diagnosis and PDT treatment of a non-tumorous indication such as arthritis, inflammatory diseases, viral or bacterial infections, dermatological, ophthalmological or urological disorders are provided as well as providing methods to obtain them in pharmaceutical quality. In addition, conjugates are provided in which these photosensitizers are attached to water-soluble polymers via cleavable linkers that can be cleaved in the body under specific conditions. Another embodiment consists of formulating the desired tetrapyrrole photosensitizer into a pharmaceutical formulation to be injected into the body avoiding undesirable effects like solubility problems or delayed pharmacokinetics of the tetrapyrrole systems.

13 Claims, 10 Drawing Sheets

(56) References Cited

OTHER PUBLICATIONS

R. Bonnett, R. D. White, U.-J. Winfield Y M. C. Berenbaum, «Hydroporphyrins of the meso-tetra (hydroxyphenyl)porphyrin series as tumor photosensitizers,» Biochem. J., vol. 261, 277-280, 1989.

D. Aicher, S. Gräfe, C. B. W. Stark Y A. Wiehe, «Synthesis of ☐-functionalized Temoporfin derivatives for an application in photodynamic therapy», Bioorg. Med. Chem. Lett. , n° 21, p. 5808-5811, 2011.

S. K. De, R. A. Gibbs, «Ruthenium(III) chloride-catalyzed chemoselective synthesis of acetals from aldehydes», Tetrahedron Lett. 2004, vol. 45, issue 44, p. 8141-8144.

M. R. Patel, A. Bhatt, J. D. Steffen, A. Chergui, J. Murai, Y. Pommier, J. M. Pascal, L. D. Trombetta, F. R. Fronczek, T. T. Talele, «Discovery and structure-activity relationship of novel 2,3-dihydrobenzofuran-7- carboxamide and 2,3-dihydrobenzofuran-3(2H)-one-7-carboxamide derivatives as poly(ADP-ribose)polymerase-1 inhibitors», J. Med. Chem. 2014, 57(13), 5579-5601.

J. Dommerholt, S. Schmidt, R. Temming, L. J. A. Hendriks, F. P. J. T Rutjes, J. C. M. Van Hest, D. J. Lefeber, P. Friedl, F. L. Van Delft, «Readily Accessible Bicyclononynes for Bioorthogonal Labeling and Three-Dimensional Imaging of Living Cells», Angew. Chem. Int. Ed. 2010, 49, 9422-9425.

D. Steinhilber, T. Rossow, S. Wedepohl, F. Paulus, S. Seiffert, R. Haag, «A Microgel Construction Kit for Bioorthogonal Encapsulation and pH-Controlled Release of Living Cells», Angewandte Chemie Int. Ed. 2013, 52, 13538-13543.

I. Papp, J. Dernedde, S. Enders, S. B. Riese, T. C. Shiao, R. Roy, R. Haag, «Multivalent presentation of mannose on hyperbranched polyglycerol and their interaction with concanavalin A lectin», ChemBioChem 2011, 12, 1075-1083.

S. Roller, H. Zhou, R. Haag, «High-loading polyglycerol supported reagents for Mitsunobu- and acylation-reactions and other useful polyglycerol derivatives», Molecular Diversity 2005, 9, 305-316.

H. R. A. Golf, H.-U. Reissig, A. Wiehe, «Regioselective Nucleophilic Aromatic Substitution Reaction of meso-Pentafluorophenyl-Substituted Porphyrinoids with Alcohols», Eur. J. Org. Chem. 2015, 2015, 1548-1568.

\* cited by examiner

Wherein:

A or B is:

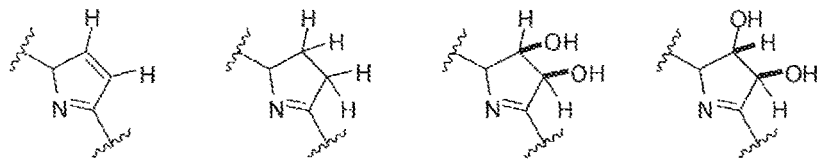

- $R^2$ is $R^2$ = -O-, -NH- or -S-.
- $R^3$ is $R^3$ = a substituted or unsubstituted alkyl group or fluoroalkyl group consisting of 4–15 carbon atoms
- M is Metallated (M = Zn, Cu, Fe, Co, Pd) or Metall-free porphyrin.
- CL is Cleavable Linker based on disulfide, acetal, ester or imine.
- L is Functional based on maleimide, cyclooctyne, alkyne, alkene, amine, carboxylic acid, hydroxyl, thiol, azide or acid chloride / targeting group based on carbohydrates (e.g. mannose, mannose-6-phosphate, galactose), antibodies (e.g. IgG, IgA, IgM, IgD, IgE antibodies), proteins (e.g. transferrin), oligopeptides (e.g. cyclic and acylic RGD-containing oligopedtides), oligonucleotides (e.g. aptamers) or vitamins (e.g. folate).
- P is a polymeric structure: hyperbranched polyglycerol (hPG), poly-ε-caprolactone (PCL), polylactic acid (PLA), polybutyl cyanoacrylate (PBCA), polyhexyl cyanoacrylate (PHCA), polystyrene (PS) or poly(methyl methacrylate) (PMMA).
- $R^1$ is a substituent either in the *meta-* or *para-* position of the phenyl ring with $R^2$ = -OH, -COOH, -NH$_2$, -COOX, -NHX, OX, -NH-Y-COOH, or -CO-Y-NH$_2$.

Wherein:

- X is a polyethyleneglycol-residue with $(CH_2CH_2O)_nCH_3$ with n = 1–30 or a carbohydrate moiety
- Y is peptides or oligopeptides wherein n=1–30.

Figure 1 (continued)

CONJUGATES OF PORPHYRINOID PHOTOSENSITIZERS AND GLYCEROL-BASED POLYMERS FOR PHOTODYNAMIC THERAPY

CROSS REFERENCE TO PRIORITY APPLICATION

This patent application claims priority to U.S. provisional patent application No. 62/300,230, filed on Feb. 26, 2016, entitled "Conjugates of Porphyrinoid Photosensitizers and Glycerol-Based Polymers for Photodynamic Therapy" by Staegemann et al., which is expressly incorporated by reference in its entirety as part of the present disclosure.

BACKGROUND OF THE INVENTION

1. Field of the Invention

The invention relates to the chemistry of biologically active compounds. More particularly to porphyrin and chlorin derivatives in combination with polymers that can be used as photosensitizers for a wide range of light irradiation treatments such as photodynamic therapy of cancer, infections and other diseases. The porphyrin and chlorin derivatives of the present invention may be attached to the polymer but may also be released upon certain triggers.

2. Invention Disclosure Statement

Photodynamic therapy (PDT) is one of the most promising techniques being explored for use in a variety of medical applications [1], [2] and particularly is a well-recognized treatment for the destruction of tumors [3]. Photodynamic therapy uses light and a photosensitizer (a dye) to achieve its desired medical effect. A large number of naturally occurring and synthetic dyes have been evaluated as potential photosensitizers for photodynamic therapy. Perhaps the most widely studied photosensitizers are the tetrapyrrolic macrocyclic compounds. Among them, especially porphyrins and chlorins have been tested for their PDT efficacy. Porphyrins are macrocyclic compounds with bridges of one carbon atom joining pyrroles to form a characteristic tetrapyrrole ring structure. There are many different classes of porphyrin derivatives including those containing dihydro-pyrrole units. Chlorins, as referred to in the present invention, are porphyrin derivatives containing one dihydro-pyrrole unit whereas bacteriochlorins are characterized by two dihydro-pyrrole units (in general in chlorins one double bond of the aromatic system in β-position is absent and in bacteriochlorins two opposite double bonds are absent compared to the porphyrin). As examples of tetrapyrrolic macrocyclic compounds used as photosensitizers, US Publication No. 2012/0,263,625A1 from Aicher et al. discloses glyco-substituted dihydroxy-chlorins for antibacterial PDT, U.S. Pat. No. 7,022,843B1 from MacAlpine et al. provides)β,β'-dihydroxy meso-substituted chlorins as photosensitizers, and U.S. Pat. No. 7,166,719B2 from Pandey et al. discloses tetrapyrrole compounds containing a fluorinated substituent where the compound is a chlorin or a bacteriochlorin for PDT diagnostic and therapeutic application.

There are several properties that an effective photosensitizer should accomplish. Among them, a desirable characteristic in order to efficiently destroy deep target tissues is a strong absorption at long wavelength. Many current photosensitizers are not efficient enough as they have low absorption in the red region of the spectrum. Chlorins have the advantage that they possess an intense absorption in the red and near-infrared region of the electromagnetic spectrum. As light of longer wavelength penetrates deeper into the tissue, it is thus possible to treat e.g. more expanded tumors, if the PDT is employed for tumor therapy. Chlorins possessing potential for PDT can either be derived from natural sources or from total synthesis. Another issue for PDT is the non-specific accumulation of the photosensitizer in undesired tissues (e.g. the skin) which leads to—in the case of skin accumulation—prolonged photosensitivity of the patient which is unpleasant for the patient and can lead to severe burns and scarring.

Thus, there is a need to enhance the effectiveness of prior art biologically active compounds used as photosensitizers in order to successfully perform a wide range of light irradiation treatments such as photodynamic therapy of cancer, infections and other diseases. Moreover, it is necessary to provide novel methods of preparation and improved photosensitizer formulations more potent than those available up to date.

Photosensitzers for anti-tumor PDT are highly lipophilic compounds with a low or no water solubility [4]. So, for the administration of photosensitizers suitable pharmaceutical formulations are needed. In this respect, International Publication No. WO2011071970 by Langer et al. discloses suitable photosensitizer formulations based on poly-lactic-co-glycolic-acid (PLGA) whereas International Publication No. WO2011071968 by Langer et al. discloses formulations based on human serum albumin (HSA) nanoparticles. International Publication No. WO2005023220 by Albrecht et al. discloses suitable liposomal formulations for the photosensitizers that are subject of the present invention. Possible oral formulations for such photosensitizers are described in International Publication No. WO2010129337 by Graefe et al. and in International Publication No. WO2010129340 by Farmer et al.

Nanoparticle formulations of photosensitizers for tumor treatment can benefit from the EPR effect (enhanced permeability and retention effect) of malign tissue where particles of a certain size can more easily leave the blood stream due to the specific structure of tumor tissue and where they are retained for longer periods due to the underdeveloped lymphatic system [5], [6]. In the art, a number of methods are described to connect photosensitizer molecules to macromolecular or nanoparticle carriers [7]. One example for possible carrier systems are polymers. International Publication No. WO2008130181A1 by Kwon et al. discloses polymers as carrier systems for pharmaceuticals. However, specifically for photosensitizers there is a need to release the photosensitizer molecule from the nanoparticle or the macromolecular carrier, given that the close proximity of the photosensitizer molecules to the carrier system changes their photophysical behavior and may lead to a suppression of the desired action, i.e. the generation of reactive oxygen species (ROS) on illumination.

OBJECTIVES AND BRIEF SUMMARY OF THE INVENTION

It is the aim of the present invention to provide biologically active compounds that can be used as photosensitizers for a wide range of applications including light irradiation treatments such as photodynamic therapy of cancer, infections and other diseases.

It is an objective of the present invention to use the chemically stable porphyrin and chlorin derivatives for various medical applications such as photodynamic therapy.

It is yet an objective of the present invention to provide $A_3B$-tetrakis-meso-substituted porphyrin and chlorin structures that can be used in the photodynamic therapy of tumors and other hyperproliferative diseases, dermatological disorders, viral or bacterial infections, opthalmological disorders or urological disorders.

It is yet another object of the present invention to provide unsymmetrically tetrakis-meso-substituted porphyrin and chlorin structures that can be used for the fluorescence diagnosis and PDT treatment of a non-tumorous indication such as arthritis and similar inflammatory diseases.

It is yet another objective of the present invention to provide pharmaceutically acceptable formulations for the biologically active compounds of the present invention such as liposomal formulation, physical encapsulation or covalent attachment to nanoparticles to be injected, avoiding undesirable effects like precipitation at the injection site or delayed pharmacokinetics of the tetrapyrrole systems.

It is yet another objective of the present invention to provide conjugates of porphyrin and chlorin photosensitizers attached to highly water-soluble polymers such as hyperbranched polyglycerol (hPG) to ensure a sufficient water-solubility of these conjugates.

It is yet another objective of the present invention to provide an $A_3B$-porphyrin or chlorin for the specific linkage to different carrier systems via various functional groups (amine, hydroxyl, maleimide, cyclooctyne, alkyne, alkene).

It is yet another objective of the present invention to provide a porphyrin or chlorin, which is linked to a carrier system. The linkage possesses one or more cleavable moieties which releases the active compound under defined conditions. This allows the controlled release at the side of action for the active compound in biological systems.

It is yet another objective of the present invention to provide a porphyrin or chlorin, which is linked to a carrier system with a functional targeting group. This allows the active targeting at the side of action, which increases the phototoxicity.

It is another object of the present invention to provide highly amphiphilic compounds to be used in the PDT-treatment of tumors, dermatological disorders, viral or bacterial infections, opthalmological disorders or urological disorders.

Briefly stated, the present invention provides methods to obtain biologically active compounds that can be used as photosensitizers for diagnostic and therapeutic applications, particularly for PDT of cancer, infections and other hyperproliferative diseases, fluorescence diagnosis and PDT treatment of a non-tumorous indication such as arthritis, inflammatory diseases, viral or bacterial infections, dermatological, ophthalmological or urological disorders. An embodiment of the present invention consists of a method to synthesize an $A_3B$-porphyrin with defined meso-substituents and then converting the B-position to a functional group which allows the connection of this porphyrin system. In another embodiment the substituent at the B-position consists of a cleavable linker, which allows the controlled release at the site of action. Another embodiment is to provide amphiphilic compounds with a higher membrane affinity and increased PDT-efficacy. Another embodiment consists of formulate the desired $A_3B$-porphyrin onto a polymeric nanoparticle formulation to be injected avoiding undesirable effects like precipitation at the injection site or delayed pharmacokinetics of the tetrapyrrole systems.

The above and other objects, features and advantages of the present invention will become apparent from the following description read in conjunction with the accompanying drawings.

DETAILED DESCRIPTION OF PREFERRED EMBODIMENTS

The present disclosure provides biologically active compounds that can be used as photosensitizers for a wide range of light irradiation treatments such as photodynamic therapy of cancer, hyperproliferative diseases, dermatological disorders, viral or bacterial infectious diseases, ophthalmological disorders and/or urological disorders. The alternative photosensitizers provided herein have the advantage that they are easily produced and characterized. Moreover, as the present disclosure provides methods to tailor amphiphilic compounds for desired PDT applications, target tissue selectivity is increased and thus PDT efficacy.

The biologically active compounds of the present disclosure that can be used for different medical indications, particularly PDT, are $A_3B$-tetrakis-meso-substituted porphyrin structures which are loaded onto polymeric nanoparticles. Additionally, the novel compounds extend their applications as they can be used for fluorescence diagnosis and PDT treatment of a non-tumorous indication such as arthritis and similar inflammatory diseases.

Figure 1:
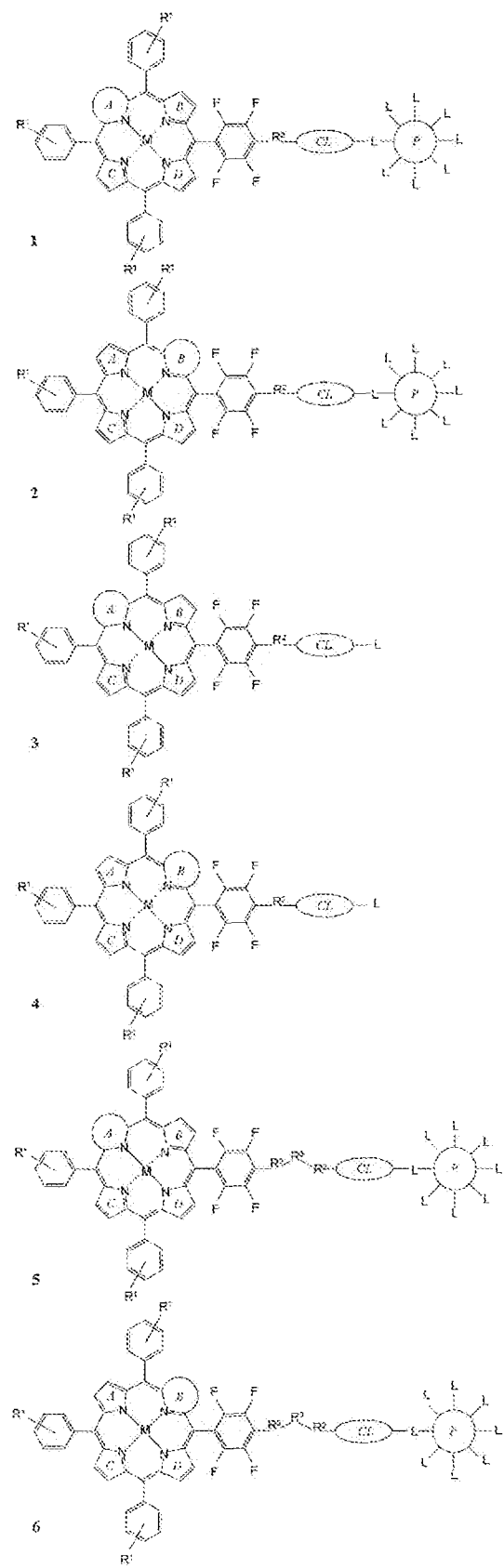
FIG. 1 shows one embodiment of the chemically stable porphyrin and chlorin derivatives used to obtain the novel photosensitizers disclosed herein.

In order to obtain the novel photosensitizers the present disclosure uses the chemically stable porphyrin and chlorin derivatives according to formulae shown in FIG. 1 and provides methods of preparation to obtain meso substituted porphyrins, more particularly the $A_3B$-tetrakis-meso-substituted porphyrin loaded on polymeric nanoparticles structures that can be used in the photodynamic therapy.

Figure 2:
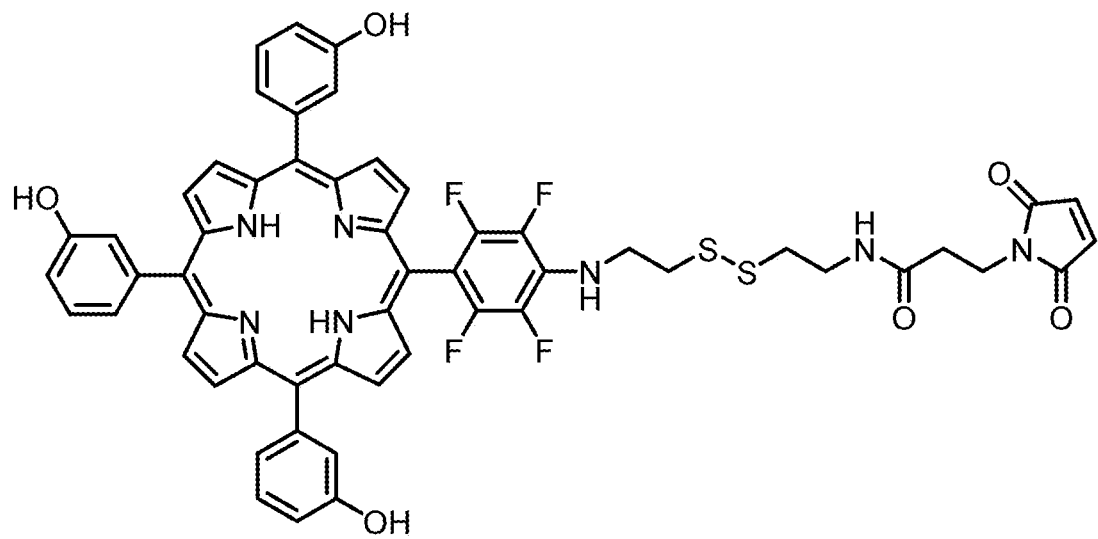
FIG. 2 illustrates one embodiment of a porphyrin of the $A_3B$ type where A is the polar substituent and B the cleavable linker with the functional group.
Figure 3:
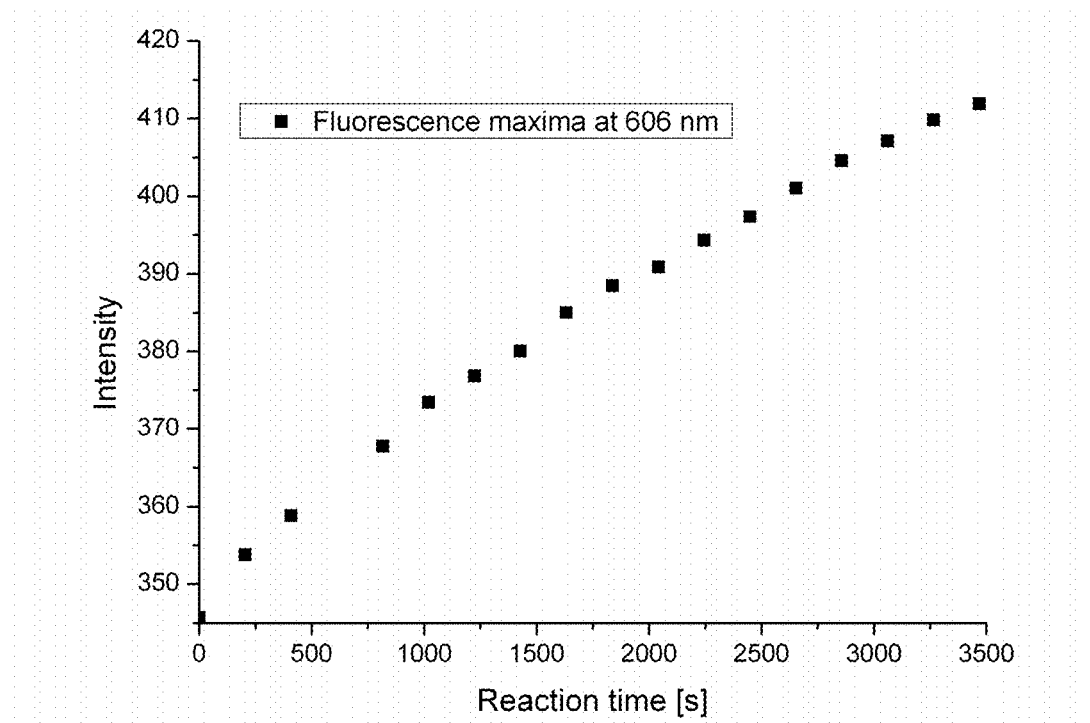
FIG. 3 shows the fluorescence spectra of the quenching experiment of one embodiment of the present disclosure (compound 1.16), showing the variation of intensity versus the reaction time.
Figure 4:
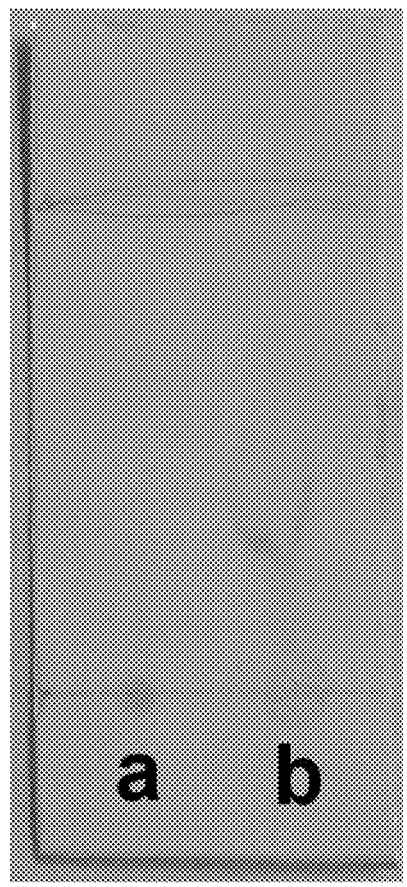
FIG. 4 shows the release study followed by thin layer chromatography of one embodiment of the present disclosure (compound 1.16).
Figure 5:
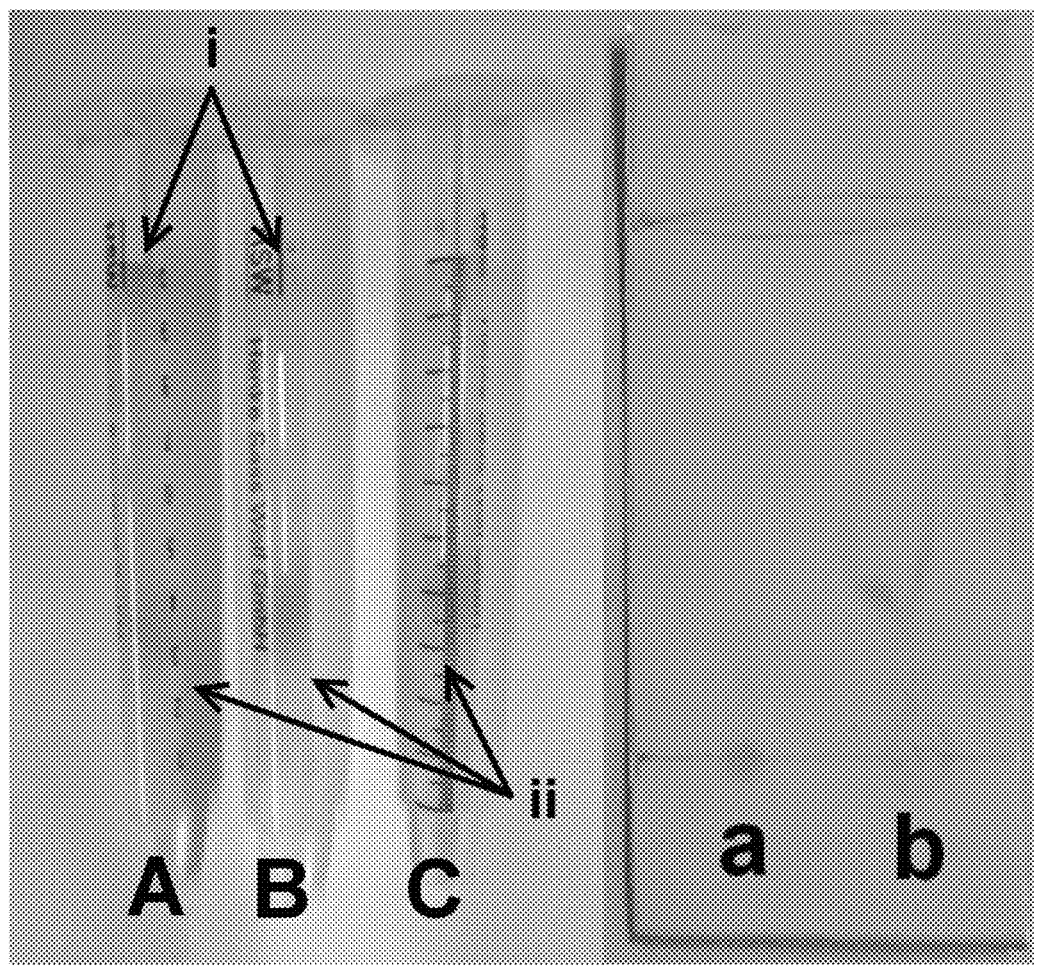
FIG. 5 shows the release study followed by SEC of one embodiment of the present disclosure (compound 1.16).
Figure 6A:
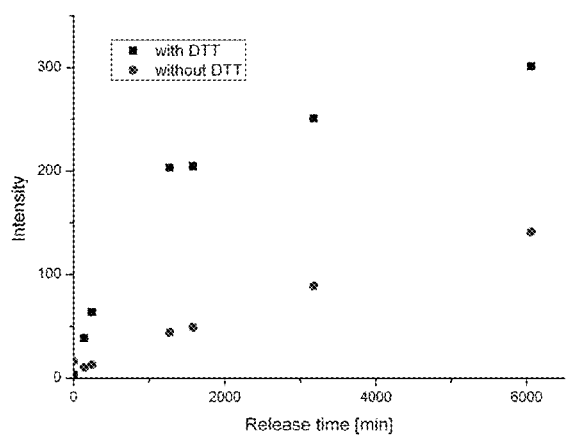
FIG. 6a shows the fluorescence spectra of a release study followed by dialysis of one embodiment of the present disclosure (compound 1.16), indicating the variation of fluorescence intensity versus release time under reductive and non-reductive conditions.
Figure 6B:
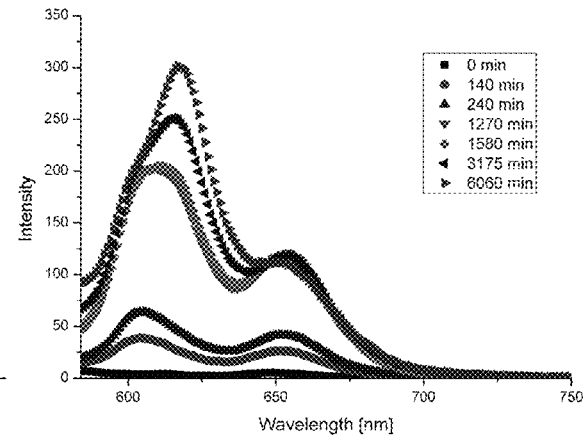
FIG. 6b shows the fluorescence spectra of a release study followed by dialysis of one embodiment of the present disclosure (compound 1.16), indicating the variation of fluorescence intensity depending on time.

An embodiment of the present disclosure consists of a method to synthesize an $A_3B$-porphyrin or chlorin with defined of meso-substituents. The B substituent contains the functionality (maleimide, cyclooctyne, alkyne, alkene, amine or hydroxyl) for linking it to the carrier system and the cleavable moiety (e.g. an acetal or disulfide containing linker; an example of a porphyrin of the $A_3B$ type is illustrated in FIG. 2, where e.g. A is the polar substituent and B the cleavable linker with the functional group) and then linking this porphyrin or chlorin to a polymeric carrier system e.g. by copper-catalyzed click or copper-free click reaction.

In yet another embodiment of the present disclosure an $A_3B$-porphyrin or chlorin is synthesized and connected via a cleavable disulfide moiety to the polymeric carrier system.

In yet another embodiment of the present disclosure an $A_3B$-porphyrin or chlorin is synthesized and connected via a cleavable acetal moiety to the polymeric carrier system.

In a specifically preferred embodiment of the present disclosure a porphyrin or chlorin of the $A_3B$-type is synthesized, having 3-hydroxyphenyl as substituent A and pentafluorophenyl residue as substituent B. Then this porphyrin is modified via a nucleophilic aromatic substitution with cystamine. To obtain the cyclooctyne functionality the porphyrin or chlorin is then reacted with (1R,8S,9r)-bicyclo[6.1.0]non-4-yn-9-methyl (4-nitrophenyl) carbonate. The final porphyrin can be linked via a copper-free click-reaction to hPG-azide.

In another specifically preferred embodiment of the present disclosure a porphyrin or chlorin of the $A_3B$-type is synthesized, having 3-hydroxyphenyl as substituent A and pentafluorophenyl residue as substituent B. Then this porphyrin is modified via a nucleophilic aromatic substitution with cystamine. To obtain the alkyne functionality the porphyrin or chlorin is then reacted with propiolic acid, and e.g. DCC and HOBt hydrate. The final porphyrin or chlorin can be linked to a polymer carrying azide groups (hPG-azide) via copper-catalyzed click-reaction.

In a specifically preferred embodiment of the present disclosure a porphyrin or chlorin of the $A_3B$-type is synthesized, having 3-hydroxyphenyl as substituent A and pentafluorophenyl residue as substituent B. Then this porphyrin is modified via a nucleophilic aromatic substitution with diaminohexane. To obtain the cyclooctyne functionality the porphyrin is then reacted with (1R,8S,9r)-Bicyclo[6.1.0]non-4-yn-9-methyl (4-nitrophenyl) carbonate. The final porphyrin or chlorin is linked via a copper-free click-reaction to a polymer (hPG) involving azide groups in connection with acetal groups thereby achieving the synthesis of a cleavable conjugate.

In a specifically preferred embodiment of the present disclosure a porphyrin or chlorin of the $A_3B$-type is synthesized, having 3-hydroxyphenyl as substituent A and pentafluorophenyl residue as substituent B. Then this porphyrin or chlorin is modified via a nucleophilic aromatic substitution with cystamine. To obtain the cyclooctyne functionality the porphyrin or chlorin is then reacted with (1R,8S,9r)-Bicyclo[6.1.0]non-4-yn-9-methyl (4-nitrophenyl) carbonate. The final porphyrin or chlorin is linked via copper-free click-reaction to a polymer (hPG) involving azide groups in connection with acetal groups, thereby achieving the synthesis of a cleavable conjugate. The specific advantage of this conjugate is that it can be cleaved under reductive (cystamine linker) as well as acidic (acetal linker) conditions.

In yet another specifically preferred embodiment of the present disclosure conjugates are prepared in which photosensitizers are attached to a polymer (hPG) and in which in addition glyco-substituents are also attached to this polymer, which render these glyco-photosensitizer-polymer conjugates especially suitable for a use in antibacterial photodynamic therapy. In this case the photosensitizers may directly be attached to the polymer or may be attached to the polymer via a cleavable linker. Adjusting the amount of glyco-substitution can be used to enhance the phototoxic effect of the conjugates against bacteria (see examples 3.2.2-3.2.6).

Acceptable starting materials for the synthesis of the porphyrins or chlorins which are the part of the subject of the present disclosure are pyrrole and aldehydes. More specifically, pyrrole and two aldehydes, two aromatic aldehydes are employed for the synthesis of the $A_3B$-substituted porphyrins which are the basis of the synthesis of the corresponding cleavable porphyrin or chlorin polymer conjugates. Pyrrole and aldehydes are subjected to a condensation reaction. Suitable methods for this condensation have long been known in the art [8]. For the synthesis of chlorins from porphyrins methods are known in the art e.g. [9], [10].

The synthesis of porphyrins that can be linked to polymers via linkers is exemplified with examples 1.1-1.10 and examples 1.17-1.19. The synthesis of porphyrins bearing specifically disulfide or acetal as the cleavable linker is exemplified with examples 1.1-1.4 and 1.6-1.10. The use of such cleavable porphyrins or chlorins as substrates for the linkage to hyperbranched polyglycerol (hPG) is a key feature of the present invention as it gives access to controlled release at the side of action for the active compound in biological systems. This is illustrated with examples 1.11-1.16. The linkage of porphyrins to hpyerbranched polyglycerol (hPG) via other linkers is exemplified with examples 1.20-1.32.

Linkages of porphyrins to polymeric carrier systems that are known in the art [7] use covalent bonds which are not cleavable like the conjugates of the present disclosure. The use of non-cleavable connections between the photosensitizer molecules and the polymer is not favorable because they can quench each other (reduction of phototoxicity). It is a specific advantage of the conjugates of the present disclosure that they can be prepared in diverse molecular weights and sizes which i.a. allows to fine-tune the properties of the conjugates in such a way that they enrich at the side of action via the EPR effect, which is limited to a specific nanoparticle size-range to achieve intra-tumoral accumulation [5]. To achieve the desired nanoparticle size-range the polymer-porphyrin or polymer-chlorin conjugates may also be prepared making use of specific polymerization techniques (e.g. nanogel precipitation).

Examples 2.1-2.4 illustrate the cleavability of the linkers, and examples 3.1-3.2 illustrate the phototoxic effect in cell culture and in bacteria.

PDT is accomplished by first incorporating the derivatives into a pharmaceutically acceptable application vehicle (which maybe e.g. an ethanolic or water-based solution of the conjugates or the porphyrin or chlorin derivatives but also a combination with other nanoparticles or a liposomal formulation) for delivery of the derivatives or conjugates to a specific treatment site. After administering the derivatives or conjugates in the vehicle to a treatment area, sufficient time is allowed so that the porphyrin and chlorin derivatives preferentially accumulate in the diseased tissue. Lastly, the treatment area is irradiated with light of a proper wavelength and sufficient power to activate the porphyrin or chlorin derivatives to induce necrosis or apoptosis in the cells of said diseased tissue. Thus, one of the main advantages is that convenient pharmaceutical formulations can be created for the biologically active compounds of the present invention such as the linkage to polymeric nanoparticles to be injected avoiding undesirable effects like precipitation at the injection site or delayed pharmacokinetics of the tetrapyrrole systems. Due to their amphiphilic nature, the chemically stable porphyrin and chlorin derivatives of the present disclosure can be prepared in various pharmaceutically acceptable and active preparations for different administration methods, e.g. injections. In a specifically preferred embodiment such amphiphilic compounds are loaded onto polymeric nanoparticles (examples 1.11-1.16 and 1.20-1.32). This polymeric nanoparticle formulation can then be injected avoiding undesirable effects such as precipitation at the injection site or delayed pharmacokinetics of the tetrapyrrole systems.

The following examples are presented to provide those of ordinary skill in the art with a full and illustrative disclosure and description of how to make the porphyrin derivatives of the invention and are not intended to limit the scope of what the inventor regards as the invention. Though examples are shown for porphyrins it is clear that the methods employed (e.g. the nucleophilic functionalization to the linkers and the connection to the polymer carriers) are also applicable to other porphyrinoids e.g. corroles or BODIPYs. Efforts have been made to ensure accuracy with respect to numbers used (e.g. amounts, temperature etc.), but some experimental errors and deviations should be accounted for. Also, best measures have been taken to name the compounds with their systematic IUPAC name, nevertheless the basic reference are the given structural formulas based on the experimental spectroscopic data.

Example 1: Synthesis of Porphyrinoids and Porphyrinoid-Polymer-Conjugates

Reagents:

L-Ascorbic acid sodium salt (99%); dimethyl sulfoxide (DMSO) (≥99.7%) extra dry over molecular sieves; dimethylformamide (DMF) (99.8%) extra dry over molecular sieves; nitromethane (≥99%) for analysis; sodium methoxide, 0.5 M solution in methanol; tetrahydrofuran (99.5%) extra dry over molecular sieve, stabilized; triethyl amine pure (99%) and trimethyl orthoformate (99%) were purchased from Acros Organics. Cystamine hydrochloride (≥97%); 1,3-dicyclohexylcarbodiimide (DCC) (99%); 1-hydroxybenzotriazole hydrate (HOBt hydrate); 3-maleimidopropionic acid N-hydroxysuccinimide ester (99%); methanol (≥99.8%); propargylamine (98%); propiolic acid (95%) and triethylamine (≥99%) were purchased from Sigma Aldrich. Dichloromethane (DCM) (≥99%) was purchased from Fisher Chemical. Sodium acetate×3 $H_2O$ for analysis (99.5%); sodium dihydrogen phosphate (99%) pure and zinc acetate×$2H_2O$ for analysis (99.5%) were purchased from Grussing. Ammonia solution (≥25%) pure; dimethyl sulfoxide ROTIDRY® (≤200 ppm $H_2O$) (≥99.5%); sodium chloride (≥99.5%) p.a, ACS, ISO; sodium hydroxide (≥99%) and sodium sulfate (≥99%) were purchased from Roth. 4-Hydroxybenzaldehyde (≥98%) for synthesis and sodium hydrogen phosphate (≥99.5%) for analysis were purchased from Merck. Indium(III) trifluoromethane sulfonate (99%) was purchased from ABCR. Tetrahydrofuran (THF) (≥99.7%) for HPLC was purchased from VWR. 1,6-Diaminohexane (≥98%) was purchased from Alfa Aesar. All these chemicals were used without further purification. Acetone-$D_6$ (99.8%); chloroform-$D_1$ (99.8%) stab. with silver; deuterium oxide (99.95%), methyl alcohol-$D_4$ (99.8%) and tetrahydrofuran-$D_8$ (99.5%) were purchased from Deutero GmbH. 1-(Allyloxy)-4-(dimethoxymethyl)benzene [11], 4-(oxiran-2-ylmethoxy)benzaldehyde [12], (1R,8S,9r)-Bicyclo[6.1.0]non-4-yn-9-methyl (4-nitrophenyl) carbonate exo+(1R,8S,9s)-Bicyclo[6.1.0]non-4-yn-9-methyl (4-nitrophenyl) carbonate endo ([13]); hPG-acetal-azide ([14]); Propargylated-mannose protected+hPG-mannose-azide [15]; hPG-azide [16]; 5,10,15-tris(3-hydro xyphenyl)-20-pentafluorophenylporphyrin+5,10,15-tris(3-acetoxyphenyl)-20-pentafluoro-phenylporphyrin [17] and 5,10,15-tris(3-hydroxyphenyl)-20-[4-(2,3-dihydroxypropoxy)tetrafluorophenyl]porphyrin [17] were prepared according to the literature or with slight modifications. All solvents were dry or distilled before using.

Thin-Layer Chromatography (TLC):

TLC analysis was performed on Merck silica gel 60 $F_{254}$ precoated aluminium sheets with fluorescence indicator $F_{254}$. In addition, detection of the intrinsic tetrapyrrole fluorescence was performed by UV light at 366 nm.

Column Chromatography:

The preparative purification of mixtures by column chromatography was conducted on Silica gel, pore size 60 A°, 40-63 μm particle size, high purity contains 0.1% Ca from Fluka or MN Silica Gel 60M, 0.04-0.063 mm/230-400 mesh, American Society for Testing (ASTM) for column chromatography from Machery-Nagel. The different eluents and the brand of the silica gel used in the synthesis are given in the individual procedures.

Dialysis:

Dialysis (dialysis tubing benzoylated, avg. flat width 32 mm (1.27 in.), Sigma Aldrich) was performed in a 1 or 2 L beaker and the solvents were changed 3 times over a period of 24 hours. The used solvents are described in synthesis.

NMR Spectroscopy:

$^1H$, $^{13}C$ and $^{19}F$ spectra were recorded on Bruker BioSpin™ AC250 ($^1H$ NMR: 250 MHz), JEOL™ ECX 400 ($^1H$ NMR: 400 MHz, $^{19}F$ NMR: 376 MHz), JEOL™ ECP 500 ($^1H$ NMR: 500 MHz, $^{13}C$ NMR: 126 MHz, $^{19}F$ NMR: 471 MHz) and Bruker BioSpin AVANCE700 ($^1H$ NMR: 700 MHz, $^{13}C$ NMR: 176 MHz) instruments. As deuterated solvents $CDCl_3$, [D6]Acetone, $D_2O$, $CD_3OD$ and [D8]THF were used. Chemical shifts δ are given in ppm relative to tetramethylsilane (TMS) as an internal standard or relative to the resonance of the solvent ($^1H$ NMR: chloroform: δ=7.26 ppm, acetone: δ=2.05 ppm, deuterium oxide: δ=4.79 ppm, methanol: δ=3.31 ppm+4.78 ppm and THF δ=3.58 ppm+1.73 ppm, $^{13}C$ NMR: chloroform: δ=77.16 ppm, acetone: δ=29.84 ppm+206.26 ppm, methanol: δ=49.00 ppm and THF δ=67.57 ppm+25.37 ppm). All spectra were recorded at RT. Abbreviations for the signals: s (singlet), bs (broad singlet), d (doublet), t (triplet), q (quartet), p (pentet), h (heptet), m (multiplet), dd (doublet of doublet), dt (doublet of triplet) and td (triplet of doublet).

MS Spectrometry:

Electrospray ionization (ESI) mass spectra were measured on an Agilent 6210 ESI-TOF from Agilent Technologies.

UV/Vis Spectroscopy:

The UV/Vis measurements were performed on a Specord S300 spectrometer from Analytik Jena at RT. The used solvents are given in the individual procedure.

Melting Point (m.p.) Measurements:

The m.p. measurements were performed on a Thermovar m.p. microscope from Reichert.

1.1 (±)-5,10,15-Tris(3-hydroxyphenyl)-20-[4-((2-(4-hydroxyphenyl)-1,3-dioxolan-4-yl)methoxy)tetrafluorophenyl]porphyrin In a sample tube with magnetic stirrer 4-hydroxybenzaldehyde (98%, 80.3 mg, 644 mol), trimethyl orthoformate (99%, 51 µl, 460 µmol) and indium(III) trifluoromethane sulfonate (99%, 4.2 mg, 7.4 µmol) were mixed and stirred neat for 3 h. 5,10,15-Tris(3-hydroxyphenyl)-20-[4-(2,3-dihydroxypropoxy)tetrafluorophenyl]porphyrin (30.0 mg, 36.4 µmol) was added and the mixture was stirred for another 2 h. The reaction was quenched with triethyl amine (99%, 500 µl, 3.55 mmol). The reaction mixture was diluted with 100 ml ethyl acetate and washed three times with 100 ml phosphate buffer (100 mM, pH 8). The organic layer was dried over $Na_2SO_4$ and the solvent was evaporated in vacuum. The crude product was purified by column chromatography (n-hexane/acetone 3:2, Fluka) to obtain (±)-5,10,15-tris(3-hydroxyphenyl)-20-[4-((2-(4-hydroxyphenyl)-1,3-dioxolan-4-yl)methoxy)tetrafluorophenyl]porphyrin 1 (25.3 mg, 27.2 µmol, 75% yield).

(±)-5,10,15-Tris(3-hydroxyphenyl)-20-[4-((2-(4-hydroxyphenyl)-1,3-dioxolan-4-yl)methoxy)tetrafluorophenyl]porphyrin $^1$H NMR ([D6]Acetone, 500 MHz): δ (ppm)=9.11-8.88 (bm, 11H, β+5,10,15-meso-3-Ar—OH), 8.59 (bs, 1H, acetal-4-Ar—OH), 7.79-7.71 (m, 6H, 5,10,15-meso-2,6-Ar), 7.637 (t, $^3$J(H,H)=7.8 Hz, 2H, 5,15-meso-5-Ar), 7.630 (t, $^3$J(H,H)=7.9 Hz, 1H, 10-meso-5-Ar), 7.49, 7.43 (d, $^3$J(H,H)=8.1, 8.7 Hz, 2H, acetal-2,6-Ar), 7.34 (d, $^3$J(H,H)=8.4 Hz,

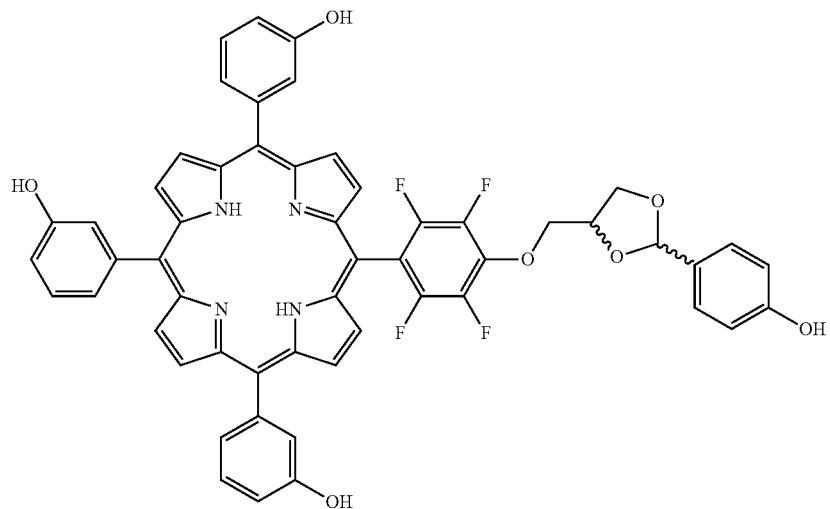 [SMILES: Oc1ccc(C2OCC(COc3c(F)c(F)c(-c4c5nc(c(-c6cccc(O)c6)c6ccc([nH]6)c(-c6cccc(O)c6)c6nc(c(-c7cccc(O)c7)c7ccc4[nH]7)C=C6)C=C5)c(F)c3F)O2)cc1]

3H, 5,10,15-meso-4-Ar), 6.91 (d, $^3$J(H,H)=8.4 Hz, 2H, acetal-3,5-Ar), 6.05, 5.85 (s, 1H, acetal-H), 4.88-4.72 (m, 3H), 4.53-4.09 (m, 2H), 2.75 (s, 2H, pyrrole-NH). $^{13}$C NMR ([D6]Acetone, 126 MHz): δ (ppm)=159.04, 159.24, 156.84, 156.80, 148.72, 146.78, 143.90, 143.71, 141.25, 139.36, 132.35, 128.68, 128.62, 127.20, 127.16, 122.83, 122.65, 121.45, 117.44, 117.10, 116.00, 115.83, 102.22, 76.82, 75.84, 75.75, 75.12, 66.14, 65.97, 51.54, 51.15. $^{19}$F NMR ([D6]Acetone, 471 MHz): δ (ppm)=-141.47-(-141.71) (m, 2F, m-Ar$_F$), -158.70-(-158.92) (m, 2F, o-Ar$_F$). HRMS (ESI): calc. for $C_{54}H_{37}F_4N_4O_7^+$ ([M+H]$^+$): 929.2598 found: 929.2632.

1.2 (±)-5,10,15-Tris(3-hydroxyphenyl)-20-[4-((2-(4-(oxiran-2-ylmethoxy)phenyl)-1,3-dioxolan-4-yl)methoxy)tetrafluorophenyl]porphyrin

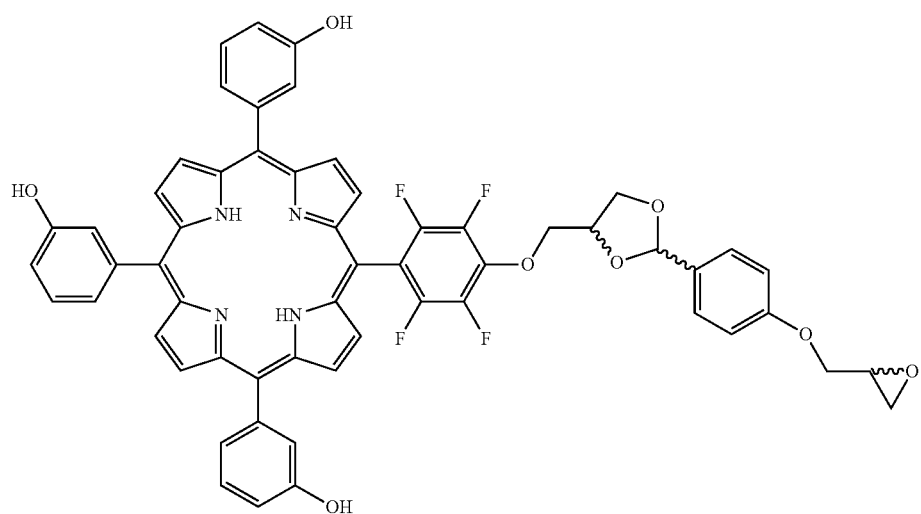 [SMILES: Oc1cccc(-c2c3nc(c(-c4cccc(O)c4)c4ccc([nH]4)c(-c4c(F)c(F)c(OCC5COC(c6ccc(OCC7CO7)cc6)O5)c(F)c4F)c4nc(c(-c5cccc(O)c5)c5ccc2[nH]5)C=C4)C=C3)c1]

In a sample tube with magnetic stirrer 4-(oxiran-2-ylmethoxy)benzaldehyde (92.4 mg, 519 µmol), trimethyl orthoformate (99%, 39 µl, 350 µmol) and indium(III) trifluoromethane sulfonate (99%, 4.2 mg, 7.4 µmol) were mixed and stirred neat for 3 h. 5,10,15-Tris(3-hydroxyphenyl)-20-[4-(2,3-dihydroxypropoxy)tetrafluorophenyl]-porphyrin (32.1 mg, 38.9 µmol) and 2 drops of DCM were added and the mixture was stirred for another 24 h. The reaction was quenched with triethyl amine (99%, 100 µl, 710 µmol). The reaction mixture was diluted with 100 ml ethyl acetate and washed three times with 100 ml phosphate buffer (100 mM, pH 8). The organic layer was dried over $Na_2SO_4$ and the solvent was evaporated in vacuum. The crude product was purified by column chromatography (n-hexane/acetone 1:1, Fluka) followed by a second column chromatography (n-hexane/acetone 3:2, Fluka) to obtain (±)-5,10,15-tris(3-hydroxyphenyl)-20-[4-(2-(4-(oxiran-2-ylmethoxy)phenyl)-1,3-dioxolan-[4-yl)methoxy)-tetrafluorophenyl]porphyrin 2 (10.4 mg, 10.6 µmol, 27% yield).

(±)-5,10,15-Tris(3-hydroxyphenyl)-20-[4(2-(4-(oxiran-2-ylmethoxy)phenyl)-1,3-dioxolan-4-yl)methoxy)]porphyrin $^1$H NMR ([D6]Acetone, 500 MHz): δ (ppm)=9.10-8.89 (bm, 11H, (δ+5,10,15-meso-3-Ar—OH), 7.77-7.70 (m, 6H, 5,10,15-meso-2,6-Ar), 7.67-7.61 (m, 3H, 5,10,15-meso-5-Ar), 7.57, 7.52 (d, $^3$J(H,H)=8.6, 8.6 Hz, 2H, acetal-2,6-Ar), 7.36-7.31 (m, 3H, 5,10,15-meso-4-Ar), 7.04, 7.03 (d, $^3$J(H,H)=8.7, 8.7 Hz, 2H, acetal-3,5-Ar), 6.07, 5.89 (s, 1H, acetal-H), 4.90-4.73 (m, 3H), 4.54-3.17 (m, 5.5H), 2.75-2.54 (m, 1.5H), −2.76 (−2.80) (m, 2H, pyrrole-NH). $^{13}$C NMR ([D6]Acetone, 126 MHz): δ (ppm)=159.84, 159.69, 156.06, 156.00, 143.09, 142.92, 142.91, 131.71, 131.66, 130.80, 130.25, 128.55, 128.28, 127.91, 127.84, 126.44, 126.38, 122.06, 122.01, 121.86, 121.85, 120.78, 120.76, 115.23, 114.96, 114.37, 114.33, 104.66, 104.64, 103.86, 75.48, 75.30, 75.16, 75.14, 69.37, 69.35, 69.32, 69.26, 66.93, 66.71, 49.76, 49.65, 43.61, 43.51. $^{19}$F NMR ([D6]Acetone, 471 MHz): δ (ppm)=−141.31-(−142.08) (m, 2F, m-Ar$_F$), −158.48-(−159.15) (m, 2F, m-Ar$_F$). HRMS (ESI): calc. for $C_{54}H_{41}F_4N_4O_8^+$ ([M+H]$^+$): 985.2861 found: 985.2851.

1.3 (±)-5,10,15-Tris(3-hydroxyphenyl)-20-[4-((2-(4-(allyloxy)phenyl)-1,3-dioxolan-4-yl)methoxy)tetra-fluorophenyl]porphyrin

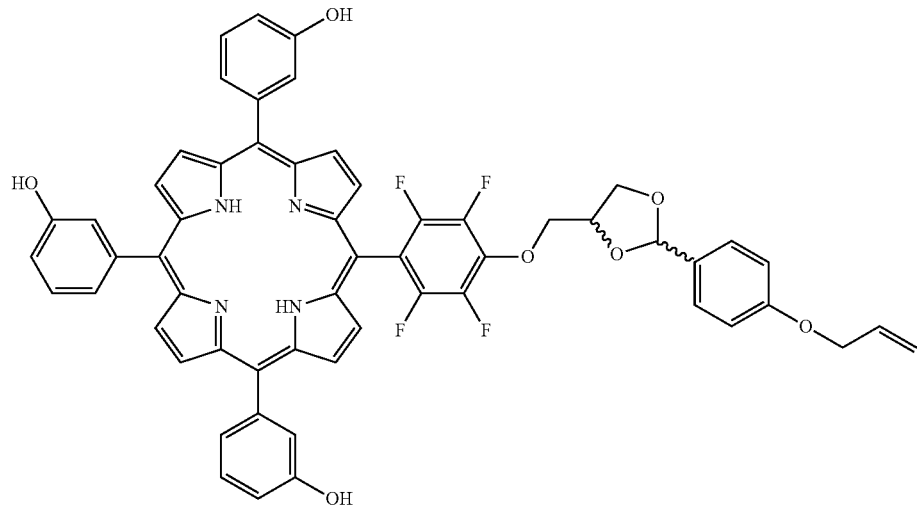 [SMILES: C=CCOc1ccc(C2OCC(COc3c(F)c(F)c(-c4c5nc(c(-c6cccc(O)c6)c6ccc([nH]6)c(-c6cccc(O)c6)c6nc(c(-c7cccc(O)c7)c7ccc4[nH]7)C=C6)C=C5)c(F)c3F)O2)cc1]

In a 10 ml flask with magnetic stirrer 1-(allyloxy)-4-(dimethoxymethyl)benzene (33.0 mg, 158 µmol), 5,10,15-tris(3-hydroxyphenyl)-20-[4-(2,3-dihydroxypropoxy)tetrafluoro-phenyl]porphyrin (80.3 mg, 97.4 µmol) and indium (III) trifluoromethane sulfonate (99%, 6.4 mg, 11 µmol) were dissolved in 5 ml of nitromethane. After 24 h 1 ml of dry THF was added and the reaction mixture was stirred for another 24 h. 1-(Allyloxy)-4-(dimethoxymethyl)benzene (275 mg, 1.32 mmol) and indium(III) trifluoromethane sulfonate (99%, 6.6 mg, 12 µmol) were added. After 3 d the reaction was completed. The reaction mixture was diluted with 50 ml MeOH/triethyl amine (99:1) and filtered over silica gel. The product was recrystallized from DCM/(MeOH/H$_2$O 4:1+NH$_3$ (pH 8)) to obtain (±)-5,10,15-tris(3-hydroxyphenyl)-20-[4-(2-(4-(allyloxy)phenyl)-1,3-dioxolan-4-yl)methoxy)tetrafluorophenyl]porphyrin 3 (52.5 mg, 54.2 µmol, 56% yield).

(±)-5,10,15-Tris(3-hydroxyphenyl)-20-[4-((2-(4-(allyloxy)phenyl)-1,3-dioxolan-4-yl)methoxy)tetra-fluorophenyl]porphyrin $^1$H NMR ([D6]Acetone, 700 MHz): δ (ppm)=9.10-8.83 (bm, 11H, β+5,10,15-meso-3-Ar—OH), 7.80-7.69 (m, 6H, 5,10,15-meso-2,6-Ar), 7.66-7.61 (m, 3H, 5,10,15-meso-5-Ar), 7.55, 7.51 (d, $^3$J(H,H)=8.6, 8.5 Hz, 2H, acetal-2,6-Ar), 7.34 (d, $^3$J(H,H)=8.4 Hz, 3H, 5,10,15-meso-4-Ar), 7.012, 7.006 (d, $^3$J(H,H)=8.5, 8.6 Hz, 2H, acetal-3,5-Ar), 6.07, 5.88 (s, 1H, acetal-H), 6.11-6.05, 5.97-5.89 (m, 1H, CH=CH$_2$), 5.46-5.38, 5.29-5.21, 5.11-5.05 (m, 2H, CH=CH$_2$), 4.90-4.72 (m, 3H), 4.61 (d, $^3$J(H,H)=5.2 Hz, 1H, CH$_2$CH=), 4.55-4.41 (m, 1.5H), 4.30 (d, $^3$J(H,H)=6.1 Hz, 1H, CH$_2$CH=), 4.16-4.06 (m, 0.5H), −2.75-(−2.76) (m, pyrrole-NH). $^{13}$C NMR ([D6]Acetone, 176 MHz): δ (ppm)=160.59, 160.44, 156.85, 156.80, 148.43, 147.06, 143.92, 143.74, 142.95, 141.57, 139.62, 134.64, 134.47, 131.36, 130.79, 129.28, 129.03, 128.71, 128.64, 127.26, 127.20, 122.87, 122.83, 122.69, 122.66, 122.65, 121.60, 121.58, 121.57, 117.45, 117.37, 116.03, 115.29, 115.25, 105.51, 104.73, 102.28, 76.29, 76.12, 76.10, 76.07, 75.95, 69.32, 69.26, 67.74, 67.53, 49.78. $^{19}$F NMR ([D6]Acetone, 471 MHz): δ (ppm)=−141.54-(−141.89) (m, 2F, m-Ar$_F$), −158.58-(−158.87) (m, 2F, m-Ar$_F$). m.p.: 140-162° C. HRMS (ESI): calc. for C$_{57}$H$_{41}$F$_4$N$_4$O$_7{}^+$ ([M+H]$^+$): 969.2911 found: 969.2929. UV/Vis (acetone): λ$_{max}$(ε)=644 (6000), 589 (13 000), 511 (41 000), 416 nm (231 000).

1.4 5,10,15-Tris(3-hydroxyphenyl)-20-[4-((2-((2-aminoethyl)disulfanyl)ethyl)-amino)tetrafluorophenyl]porphyrin

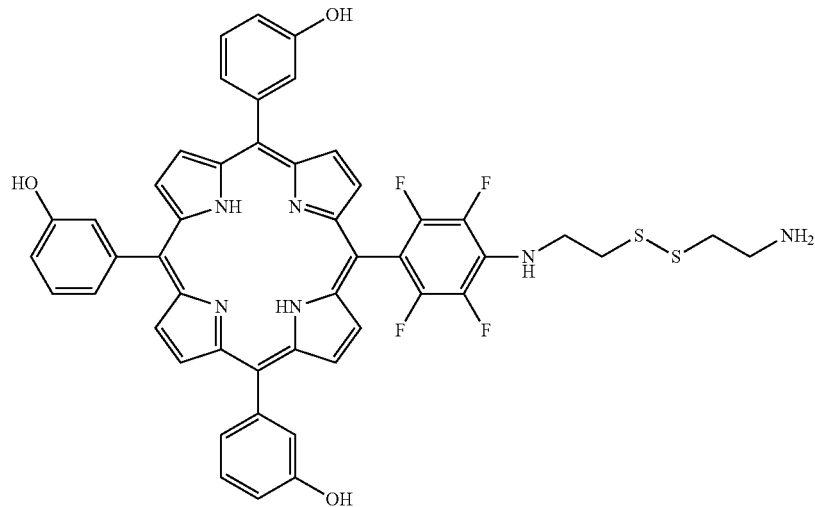

In a 100 ml flask with magnetic stirrer sodium hydroxide (99%, 1.55 g, 38.4 mmol) was dissolved in 20 ml of $H_2O$. To the stirring solution cystamine dihydrochloride (97%, 2.71 g, 11.7 mmol) was added. After 10 min stirring the aqueous solution was extracted four times with 100 ml of DCM. Afterwards the organic layer was dried over $Na_2SO_4$. The product was evaporated to dryness and the remaining residue was dissolved in 1.5 ml of DMSO (Roth). 5,10,15-Tris(3-hydroxyphenyl)-20-pentafluorophenylporphyrin (151 mg, 177 µmol) was added. The solution was stirred at 100° C. for 30 min in the microwave oven (300 W). The crude product was diluted with 100 ml of ethyl acetate and washed once with 50 ml of saturated NaCl-solution and twice with $H_2O$. Afterwards the organic layer was dried over $Na_2SO_4$. The crude product was evaporated to dryness and the remaining residue was purified by column chromatography (DCM/methanol 85:15, Fluka) and recrystallization from DCM to obtain 5,10,15-tris(3-hydroxyphenyl)-20-[4-((2-((2-aminoethyl)disulfanyl)ethyl)amino) tetrafluorophenyl]porphyrin (136 mg, 154 µmol, 87% yield) as a purple solid.

5,10,15-Tris(3-hydroxyphenyl)-20-[4-((2-((2-aminoethyl)disulfanyl)ethyl)amino)-tetrafluorophenyl] porphyrin $^1$H NMR ([D8]THF, 700 MHz): δ (ppm)=9.04-8.81 (m, 11H, β+5,10,15-meso-3-Ar—OH), 7.69-7.60 (m, 6H, 5,10,15-meso-2,6-Ar), 7.58-7.44 (m, 3H, 5,10,15-meso-5-Ar), 7.20 (d, $^3$J(H,H)=8.2 Hz, 1H, 10-meso-4-Ar), 7.18 (dd, $^3$J(H,H)=8.9, $^4$J(H,H)=2.1 Hz, 1H, 10-meso-4-Ar), 6.18 (bs, 1H, NH), 3.99 (q, $^3$J(H,H)=6.6 Hz, 2H, NHCH$_2$), 3.50 (t, $^3$J(H,H)=7.2 Hz, 2H, CH$_2$NH$_2$), 3.35 (t, $^3$J(H,H)=7.2 Hz, 2H, SCH$_2$), 3.24 (t, $^3$J(H,H)=6.8 Hz, 2H, SCH$_2$), −2.73 (s, 2H, pyrrole-NH). $^{13}$C NMR ([D8]THF, 176 MHz): δ (ppm)= 157.41, 148.83, 147.46, 144.37, 144.20, 138.86, 137.57, 130.01, 128.44, 128.39, 127.13, 123.16, 122.40, 121.50, 115.93, 108.36, 103.65, 45.62, 40.00, 39.80, 35.57. $^{19}$F NMR ([D8]THF, 376 MHz): δ (ppm)=−142.15-(−143.15) (m, 2F, m-Ar$_F$), −161.73-(−162.85) (m, 2F, o-Ar$_F$). m.p.: >230° C. HRMS (ESI): calc. for $C_{48}H_{37}F_4N_6O_3S_2^+$ ([M+H]$^+$): 885.2305 found: 885.2342. UV/Vis (ethanol): λ$_{max}$ (ε)= 645 (2000), 589 (4000), 547 (5000), 512 (14 000), 416 nm (257 000).

1.5 5,10,15-Tris(3-hydroxyphenyl)-20-[6-aminohexylamino)tetrafluorophenyl]-porphyrin

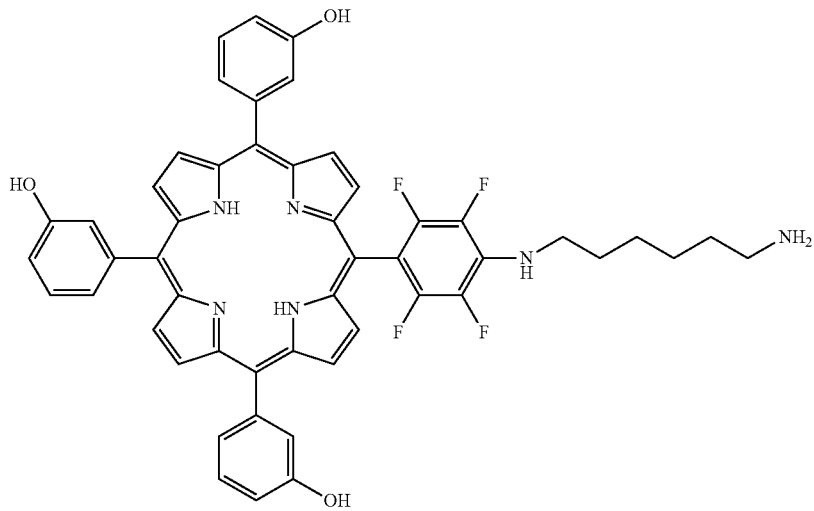 [SMILES: NCCSSCCNc1c(F)c(F)c(-c2c3nc(c(-c4cccc(O)c4)c4ccc([nH]4)c(-c4cccc(O)c4)c4nc(c(-c5cccc(O)c5)c5ccc2[nH]5)C=C4)C=C3)c(F)c1F]

In a 10 ml flask with magnetic stirrer 5,10,15-tris(3-hydroxyphenyl)-20-pentafluorophenylporphyrin (120 mg, 159 µmol) was dissolved in 4 ml of dry DMSO (Acros). To the stirring solution 1,6-diaminohexane (98%, 3.60 ml, 25.5 mmol) was added. The solution was stirred at 100° C. for 1 h. The crude product was diluted with 100 ml of ethyl acetate and washed twice with 150 ml of saturated NaCl-solution and twice with 150 ml $H_2O$. Afterwards the organic layer was dried over $Na_2SO_4$. The crude product was evaporated to dryness and the remaining residue was purified by column chromatography (DCM/methanol 8:2, Fluka) and recrystallization from DCM to obtain 5,10,15-tris(3-hydroxyphenyl)-20-[6-aminohexylamino)tetrafluorophenyl]porphyrin (107 mg, 127 µmol, 79% yield) as a purple solid.

5,10,15-Tris(3-hydroxyphenyl)-20-[6-aminohexylamino)tetrafluorophenyl]-porphyrin $^1$H NMR (CD$_3$OD, 500 MHz): δ (ppm)=8.94 (bs, 8H, β), 7.68-7.64 (m, 3H, 5,10,15-meso-2-Ar), 7.63 (t, $^3$J(H,H)=8.0 Hz, 3H, 5,10,15-meso-6-Ar), 7.543 (t, $^3$J(H,H)=7.7 Hz, 2H, 5,15-meso-5-Ar), 7.537 (t, $^3$J(H,H)=7.9 Hz, 1H, 10-meso-5-Ar), 7.24 (dd, $^3$J(H,H)=8.3, $^4$J(H,H)=1.6 Hz, 3H, 5,15-meso-4-Ar), 3.52 (t, $^3$J(H,H)=7.3 Hz, 2H, NHCH$_2$), 2.62 (t, $^3$J(H,H)=7.2 Hz, 2H, NHCH$_2$), 1.73 (p, $^3$J(H,H)=7.3 Hz, 2H, NHCH$_2$CH$_2$), 1.52-1.31 (m, 6H, NHCH$_2$CH$_2$+NHCH$_2$CH$_2$CH$_2$). $^{13}$C NMR (CD$_3$OD, 126 MHz): δ (ppm)= 157.50, 157.43, 144.36, 144.24, 128.77, 128.72, 127.42, 127.38, 123.37, 123.32, 122.81, 121.88, 116.21, 104.08, 46.49, 42.15, 32.90, 31.92, 27.65. $^{19}$F NMR (CD$_3$OD, 471 MHz): δ (ppm)=143.95 (d, $^3$J(F,F)=16.1 Hz, 2F, m-Ar$_F$); −163.40 (d, $^3$J(F,F)=16.1 Hz, 2F, o-Ar$_F$). m.p.: >300° C. HRMS (ESI): calc. for C$_{50}$H$_{41}$F$_4$N$_6$O$_3$$^+$ ([M+H]$^±$): 849, 3176; found: 849,3184. UV/Vis (MeOH): λ$_{max}$ (ε)=644 (2140), 588 (4680), 588 (5500), 545 (15 800), 415 (178 000).

1.6 5,10,15-Tris(3-hydroxyphenyl)-20-[4-((2-((2-((3-maleimidyl)propanamido)-ethyl)disulfanyl)ethyl)amino)tetrafluorophenyl]porphyrin

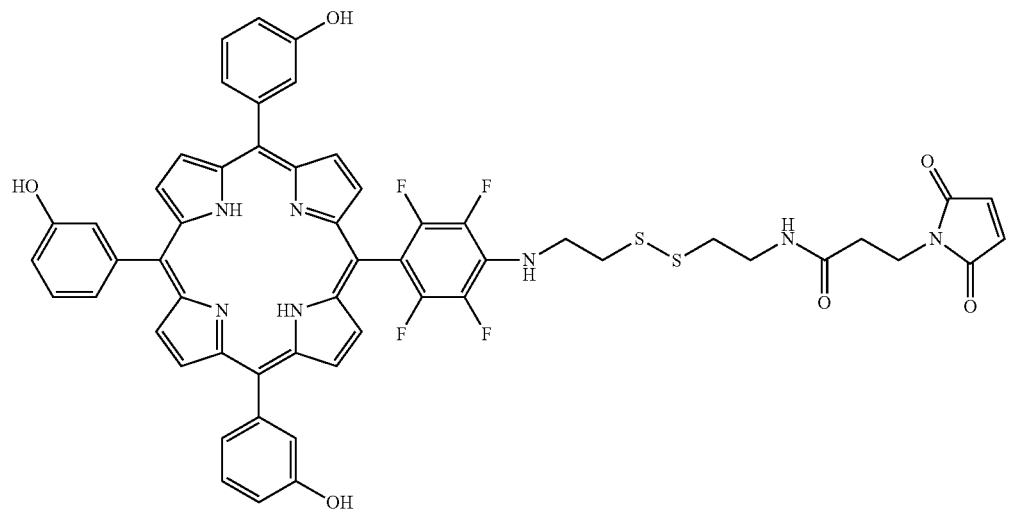 [SMILES: O=C(CCN1C(=O)C=CC1=O)NCCSSCCNc1c(F)c(F)c(-c2c3nc(c(-c4cccc(O)c4)c4ccc([nH]4)c(-c4cccc(O)c4)c4nc(c(-c5cccc(O)c5)c5ccc2[nH]5)C=C4)C=C3)c(F)c1F]

In a 10 ml flask with magnetic stirrer under argon 5,10,15-tris(3-hydroxyphenyl)-20-[4-((2-((2-aminoethyl)disulfanyl)ethyl)amino)tetrafluorophenyl]porphyrin (122 mg, 138 μmol) was dissolved in 1.5 ml of anhydrous DMF. 3-(Maleimido)propionic acid N-hydroxysuccinimide ester (99%, 47.1 mg, 177 μmol) was added and the solution was stirred for 1 h at RT. The reaction mixture was diluted with 100 ml ethyl acetate and washed four times with 150 ml $H_2O$. The organic layer was dried over $Na_2SO_4$ and the solvent was evaporated in vacuum. The crude product was purified by column chromatography (DCM/MeOH 95:5, Fluka). The product was recrystallized from n-hexane to obtain 5,10,15-tris(3-hydroxyphenyl)-20-[4-((2-((2-(3-maleimidyl)-propanamido)ethyl)disulfanyl)ethyl)amino)tetrafluorophenyl]porphyrin (116 mg, 112 μmol, 81% yield).

5,10,15-Tris(3-hydroxyphenyl)-20-[4-((2-((2-((3-maleimidyl)propanamido)ethyl)-disulfanyl)ethyl)amino)tetrafluorophenyl]porphyrin $^1$H NMR ([D8]THF, 500 MHz): δ (ppm)=9.02-8.85 (bm, 8H, β), 8.75-8.66 (m, 3H, 5,10,15-meso-3-Ar—OH), 7.72-7.61 (m, 6H, 5,10,15-meso-2,6-Ar), 7.55 (t, $^3$J(H,H)=7.8 Hz, 3H, 5,10,15-meso-5-Ar), 7.53-7.44 (m, 1H, NHCO), 7.26-7.14 (m, 3H, 5,10,15-meso-4-Ar), 6.74 (s, 2H, HC=CH), 6.07 (bs, 1H, $Ar_F$—NH), 3.98 (d, $^3$J(H,H)=7.3 Hz, 2H, $Ar_F$—NHCH$_2$), 3.83-3.69 (m, 2H, CH$_2$N), 3.53 (t, $^3$J(H,H)=6.2 Hz, 2H, CH$_2$NHCO), 3.19 (t, $^3$J(H,H)=6.8 Hz, 2H, $Ar_F$—NHCH$_2$CH$_2$S), 2.90 (t, $^3$J(H,H)=6.7 Hz, 2H, SCH$_2$CH$_2$NHCO), 2.50-2.36 (m, 2H, COCH$_2$), -2.72 (s, 2H, pyrrole-NH). $^{13}$C NMR ([D8]THF, 126 MHz): δ (ppm)= 171.04, 170.21, 157.08, 157.04, 148.77, 146.84, 144.03, 143.89, 138.88, 136.97, 134.86, 131.60, 129.65, 128.11, 128.05, 126.80, 122.81, 122.08, 121.16, 115.58, 108.21, 103.20, 45.44, 39.68, 39.07, 38.45, 34.93, 34.91. $^{19}$F NMR ([D8]THF, 471 MHz): δ (ppm)=-142.56-(-142.86) (m, 2F, m-$Ar_F$), -162.24-(-162.47) (m, 2F, o-$Ar_F$). m.p.: 185° C. HRMS (ESI): calc. for $C_{55}H_{42}F_4N_7O_6S_2^+$ ([M+H]$^+$): 1036.2569 found: 1036.2588. UV/Vis (methanol): $\lambda_{max}(\varepsilon)$= 645 (3000), 588 (5000), 546 (6000), 512 (16 000), 415 nm (229 000).

1.7 5,10,15-Tris(3-hydroxyphenyl)-20-[4-((2-((2-(((((1R,8S,9r)-bicyclo[6.1.0]non-4-yn-9-yl)methoxy)carbonyl)amino)ethyl)disulfanyl)ethyl)amino)tetrafluoro-phenyl]porphyrin

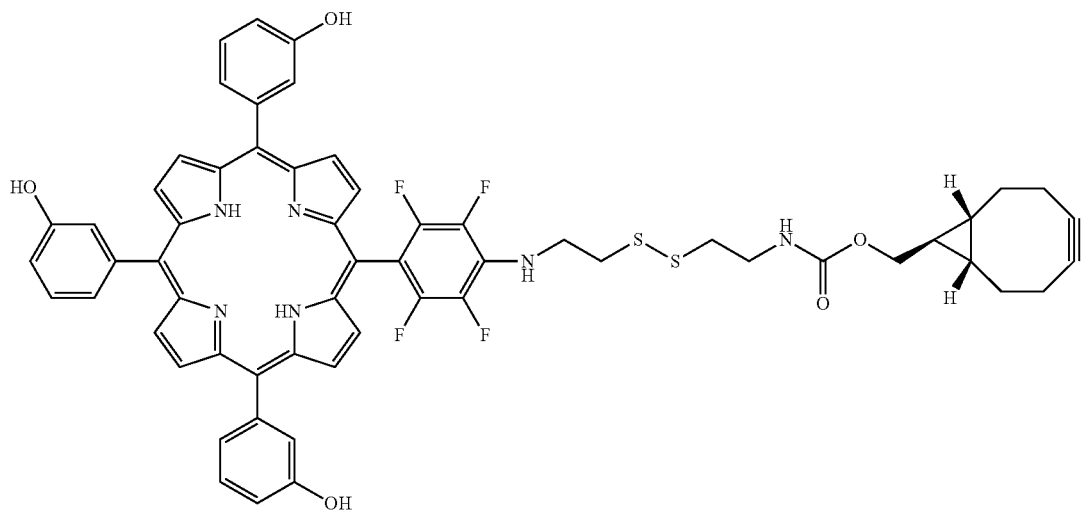 [SMILES: O=C(NCCSSCCNc1c(F)c(F)c(-c2c3nc(c(-c4cccc(O)c4)c4ccc([nH]4)c(-c4cccc(O)c4)c4nc(c(-c5cccc(O)c5)c5ccc2[nH]5)C=C4)C=C3)c(F)c1F)OC[C@H]1[C@@H]2CCC#CCC[C@@H]21]

In a 25 ml two-necked flask with magnetic stirrer under argon (1R,8S,9r)-Bicyclo[6.1.0]non-4-yn-9-methyl (4-nitrophenyl) carbonate exo (46.8 mg, 148 μmol) was dissolved in 3.5 ml of anhydrous DMF. 5,10,15-Tris(3-hydroxyphenyl)-20-[4-((2-((2-aminoethyl)disulfanyl)ethyl) amino)tetrafluorophenyl]porphyrin (105 mg, 118 μmol) and triethyl amine (99%, 8.7 μl, 62.0 μmol) were added and the solution was stirred for 20 min at RT. The reaction mixture was diluted with 50 ml ethyl acetate and washed four times with 30 ml $H_2O$. The organic layer was dried over $Na_2SO_4$ and the solvent was evaporated in vacuum. The crude product was purified by column chromatography (DCM/MeOH 96:4, Fluka). The product was recrystallized from n-hexane to obtain 5,10,15-tris(3-hydroxyphenyl)-20-[4-((2-((2-(((((1R,8S,9r)-bicyclo[6.1.0]non-4-yn-9-yl)-methoxy)carbonyl) amino)ethyl)disulfanyl)ethyl) amino)tetrafluorophenyl]porphyrin (123 mg, 116 μmol, 98% yield).

5,10,15-Tris(3-hydroxyphenyl)-20-[4-((2-((2-(((((1R,8S,9r)-bicyclo[6.1.0]non-4-yn-9-yl)methoxy)carbonyl)amino)ethyl)disulfanyl)ethyl)amino)tetrafluorophenyl]porphyrin $^1$H NMR ([D8]THF, 700 MHz): δ (ppm)=8.99-8.88 (m, 8H, (3), 8.70-8.67 (s, 3H, 5,10,15-meso-3-Ar—OH), 7.69-7.62 (m, 6H, 5,10,15-meso-2,6-Ar), 7.58-7.52 (m, 3H, 5,10,15-meso-5-Ar), 7.208 (dd, $^3$J(H,H)=8.4, $^4$J(H,H)=1.1 Hz, 1H, 10-meso-4-Ar), 7.203 (dd, $^3$J(H,H)=8.4, $^4$J(H,H)=1.2 Hz, 2H, 5,15-meso-4-Ar), 6.59 (t, $^3$J(H,H)=5.9 Hz, 1H, C(O)NH), 6.00 (t, $^3$J(H,H)=7.1 Hz, 1H, Ar$_F$—NH), 3.99 (q, $^3$J(H,H)=6.9 Hz, 2H, Ar$_F$—NHCH$_2$), 3.93 (d, $^3$J(H,H)=6.9 Hz, 2H, OCH$_2$), 3.50 (q, $^3$J(H,H)=6.6 Hz, 2H, C(O)N-HCH$_2$), 3.20 (t, $^3$J(H,H)=6.8 Hz, 2H, Ar$_F$—NHCH$_2$CH$_2$), 2.93 (t, $^3$J(H,H)=6.8 Hz, 2H, C(O)NHCH$_2$CH$_2$), 2.29 (d, $^3$J(H,H)=14.1 Hz, 2H, 2,7-Bicyclo), 2.16 (t, $^3$J(H,H)=14.0 Hz, 2H, 3,6-Bicyclo), 2.00 (d, $^3$J(H,H)=15.9 Hz, 2H, 3,6-Bicyclo), 1.35-1.26 (m, 2H, 2,7-Bicyclo), 0.71-0.64 (m, 2H, 1,8-Bicyclo), 0.61 (p, 1H, $^3$J(H,H)=6.5 Hz, 9-Bicyclo), 2.71 (s, 2H, inner core NH). $^{13}$C NMR ([D8]THF, 176 MHz): δ (ppm)=157.55, 157.19, 148.72, 147.38, 144.31, 144.18, 138.83, 137.48, 131.95, 129.86, 128.35, 128.30, 127.17, 127.14, 123.05, 122.29, 121.36, 115.78, 108.58, 98.97, 69.15, 45.69, 41.01, 40.01, 39.39, 34.24, 24.96, 23.86, 21.81. $^{19}$F NMR ([D8]THF, 471 MHz): δ (ppm)=−142.66 (t, $^3$J(F,F)=25.8 Hz, 2F, m-Ar$_F$), −162.43 (s, 2F, o-Ar$_F$). m.p.: >300° C. HRMS (ESI): calc. for C$_{59}$H$_{49}$F$_4$N$_6$O$_5$S$_2{}^+$ ([M+H]$^+$): 1061.3136 found: 1061.3008. UV/Vis (methanol): λ$_{max}$(ε)=645 (2450), 588 (5130), 545 (5890), 512 (17 000), 415 nm (240 000).

1.8 5,10,15-Tris(3-hydroxyphenyl)-20-[4-((2-((2-(((((1R,8S,9s)-bicyclo[6.1.0]non-4-yn-9-yl) methoxy) carbonyl) amino) ethyl) disulfanyl) ethyl) amino) tetrafluoro-phenyl]porphyrin

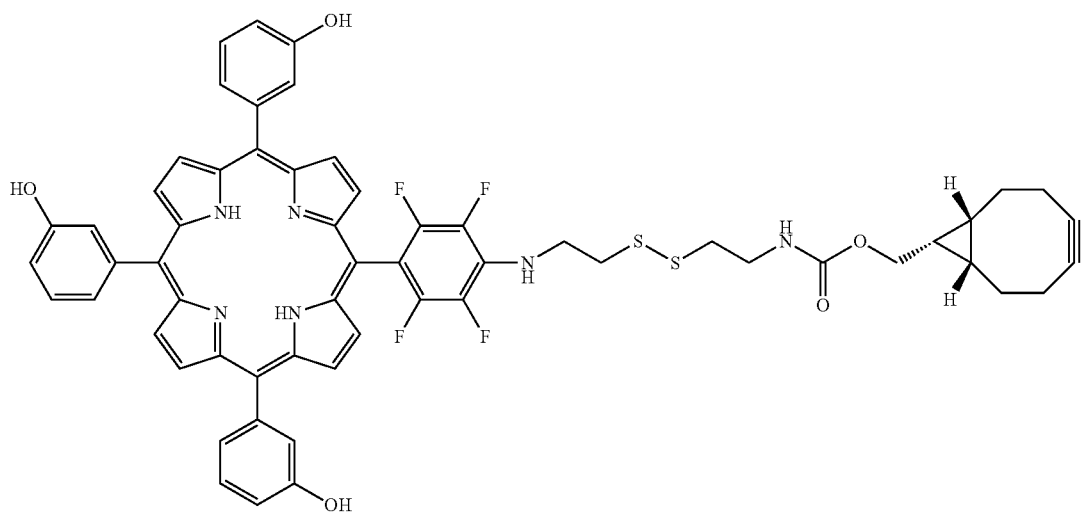 [SMILES: O=C(NCCSSCCNc1c(F)c(F)c(-c2c3nc(c(-c4cccc(O)c4)c4ccc([nH]4)c(-c4cccc(O)c4)c4nc(c(-c5cccc(O)c5)c5ccc2[nH]5)C=C4)C=C3)c(F)c1F)OC[C@@H]1[C@@H]2CCC#CCC[C@@H]21]

In a 25 ml two-necked flask with magnetic stirrer under argon (1R,8S,9s)-Bicyclo[6.1.0]non-4-yn-9-methyl (4-nitrophenyl) carbonate endo (97.0 mg, 308 μmol) was dissolved in 7.0 ml of anhydrous DMF. 5,10,15-Tris(3-hydroxyphenyl)-20-[4-((2-((2-aminoethyl)disulfanyl)ethyl) amino)tetrafluorophenyl]porphyrin (208 mg, 235 μmol) and triethyl amine (99%, 18.0 μl, 130 μmol) were added and the solution was stirred for 15 min at RT. The reaction mixture was diluted with 150 ml ethyl acetate and washed four times with 50 ml H$_2$O. The organic layer was dried over Na$_2$SO$_4$ and the solvent was evaporated in vacuum. The crude product was purified by column chromatography (DCM/MeOH 96:4, Fluka). The product was recrystallized from n-hexane to obtain 5,10,15-tris(3-hydroxyphenyl)-20-[4-((2-(2-(((((1R,8S,9s)-bicyclo [6.1.0]non-4-yn-9-yl)-methoxy)carbonyl)amino)ethyl)disulfanyl)ethyl) amino)tetrafluorophenyl]porphyrin (223 mg, 210 μmol, 90% yield).

5,10,15-Tris(3-hydroxyphenyl)-20-[4-((2-((2-(((((1R,8S,9s)-bicyclo[6.1.0]non-4-yn-9-yl)methoxy)carbonyl)amino)ethyl)disulfanyl)ethyl)amino)tetrafluorophenyl]porphyrin HRMS (ESI): calc. for C$_{59}$H$_{47}$F$_4$N$_6$O$_5$S$_2{}^-$ ([M−H]$^-$): 1059.2985 found: 1059.3858.

1.9 5,10,15-Tris(3-hydroxyphenyl)-20-[2,3,5,6-tetrafluoro-4-(N-(2-((2-amino-ethyl)disulfanyl)ethyl propiolamido))-phenyl]porphyrin

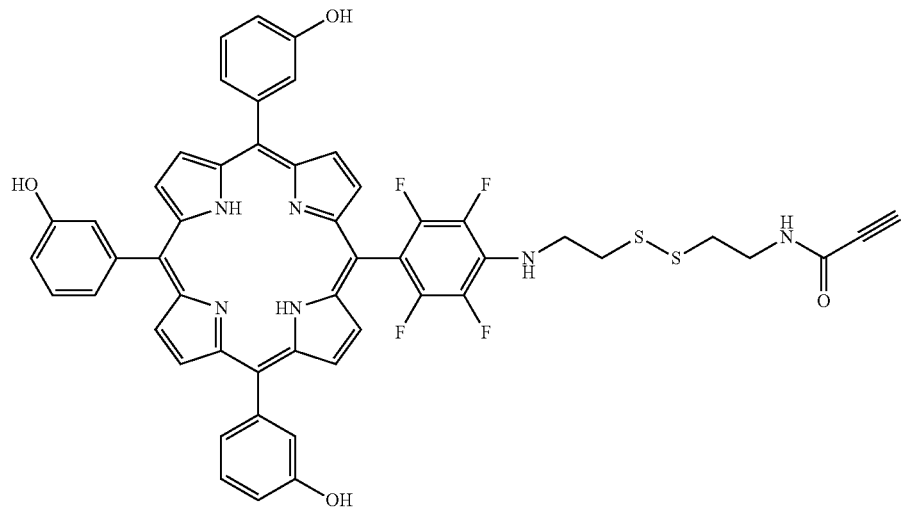 [SMILES: C#CC(=O)NCCSSCCNc1c(F)c(F)c(-c2c3nc(c(-c4cccc(O)c4)c4ccc([nH]4)c(-c4cccc(O)c4)c4nc(c(-c5cccc(O)c5)c5ccc2[nH]5)C=C4)C=C3)c(F)c1F]

In a 10 ml flask with magnetic stirrer DCC (99%, 16.0 mg, 76.7 mol), propiolic acid (95%, 4.82 µl, 73.9 µmol) and HOBt hydrate (12.0 mg, 88.8 µmol) were dissolved in 1 ml of THF and stirred for 10 min at RT. 5,10,15-Tris(3-hydroxyphenyl)-20-[2,3,5,6-tetrafluoro-4-(N-(2-((2-aminoethyl)disulfanyl)ethyl amino))phenyl]porphyrin (69.0 mg, 78.0 µmol) was added and the solution was stirred for 2 h at RT. The crude product was dissolved in 100 ml of ethyl acetate and washed three times with 50 ml of H$_2$O. Afterwards the organic layer was dried over Na$_2$SO$_4$ and the solution was evaporated to dryness. The crude product was purified by column chromatography (DCM/methanol 85:15, Machery-Nagel) and recrystallization from DCM/n-hexane to obtain 5,10,15-tris (3-hydroxyphenyl)-20-[2,3,5,6-tetrafluoro-4-(N-(2-((2-aminoethyl)disulfanyl)ethyl propiolamido))phenyl]porphyrin (56.0 mg, 59.8 µmol, 77% yield) as a purple solid.

5,10,15-Tris(3-hydroxyphenyl)-20-[2,3,5,6-tetrafluoro-4-(N-(2-((2-aminoethyl)-disulfanyl)ethyl propiolamido))phenyl]porphyrin $^1$H NMR ([D6]Acetone, 700 MHz): δ (ppm)=9.12 (bs, 2H, 2.18-β), 9.02 (bs, 2H, 3.17-β), 9.00-8.95 (m, 7H, 7,8,12,13-β+5,10,15-meso-3-Ar—OH), 8.08 (bs, 1H, NHC (O)), 7.76 (d, $^4$J(H,H)=2.1 Hz, 2H, 5,15-meso-2-Ar), 7.75 (d, $^4$J(H,H)=2.1 Hz, 1H, 10-meso-2-Ar), 7.73 (d, $^3$J(H,H)= 7.7 Hz, 2H, 5,15-meso-6-Ar), 7.72 (d, $^3$J(H,H)=8.7 Hz, 1H, 10-meso-6-Ar), 7.66-7.61 (m, 3H, 5,10,15-meso-5-Ar), 7.33 (dd, $^3$J(H,H)=8.5, $^4$J(H,H)=2.3 Hz, 3H, 5,10,15-meso-4-Ar), 5.91 (t, $^3$J(H,H)=7.1 Hz, 1H, Ar$_F$—NH), 4.04 (q, $^3$J(H,H)= 6.9 Hz, 2H, Ar$_F$—NHCH$_2$), 3.68 (q, $^3$J(H,H)=6.6 Hz, 2H, CH$_2$NHC(O)), 3.53 (s, 1H, C≡CH), 3.26 (t, $^3$J(H,H)=6.7 Hz, 2H, Ar$_F$—NHCH$_2$CH$_2$), 3.02 (t, $^3$J(H,H)=6.8 Hz, 2H, CH$_2$CH$_2$NHC(O)), 2.75 (s, 2H, pyrrole-NH). $^{13}$C NMR ([D6]Acetone, 176 MHz): δ (ppm)=156.86, 156.82, 152.92, 148.57, 147.22, 143.95, 143.81, 138.91, 137.55, 132.08, 129.96, 128.67, 128.61, 127.20, 127.15, 122.86, 122.82, 122.34, 121.39, 115.99, 108.25, 103.58, 78.69, 74.47, 45.44, 39.58, 39.44, 37.95. $^{19}$F NMR ([D6]Acetone, 376 MHz): δ (ppm)=143.11 (d, $^3$J(F,F)=21.0 Hz, 2F, m-Ar$_F$), 161.79 (d, $^3$J(F,F)=18.9 Hz, 2F, o-Ar$_F$). m.p.: >230° C. HRMS (ESI): calc. for C$_{51}$H$_{37}$F$_4$N$_6$O$_4$S$_2^+$ ([M+H]$^±$): 937.2254 found: 937.2294. UV/Vis (ethanol): λ$_{max}$(ε)=645 (3000), 589 (6000), 547 (7000), 512 (18 000), 416 nm (329 000).

1.10 {5,10,15-Tris(3-hydroxyphenyl)-20-[2,3,5,6-tetrafluoro-4-(N-(2-((2-aminoethyl)disulfanyl)ethyl propiolamido))-phenyl]porphyrinato}-zinc(II)

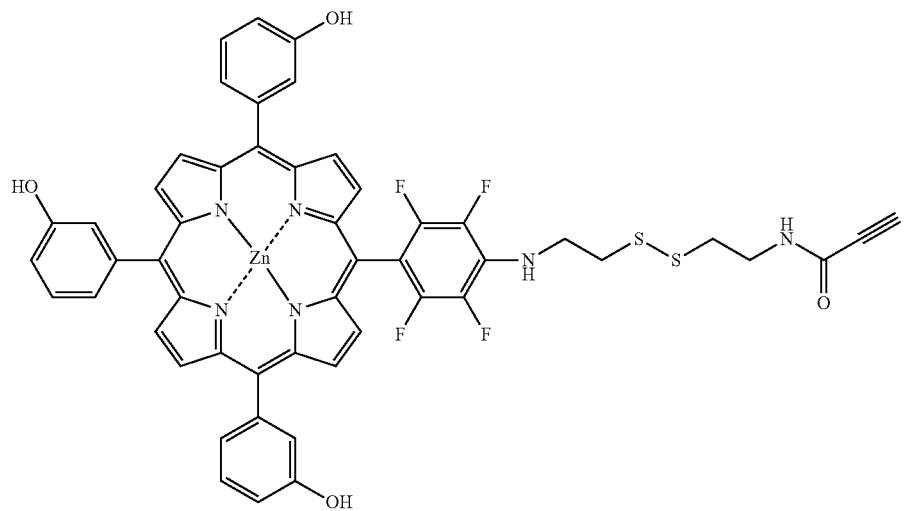

In a 10 ml flask with magnetic stirrer 5,10,15-tris(3-hydroxyphenyl)-20-[2,3,5,6-tetrafluoro-4-(N-(2-((2-aminoethyl)disulfanyl)ethyl-propiolamido))phenyl]porphyrin (56.0 mg, 59.8 μmol) was dissolved in 2 ml of methanol. A point of a spatula of sodium acetate and zinc acetate dihydrate (138 mg, 629 μmol) was added to the stirred solution. The solution was stirred for 30 min at RT. The crude product was dissolved in 100 ml of ethyl acetate and washed three times with 50 ml of $H_2O$. Afterwards the organic layer was dried over $Na_2SO_4$ and the solution was evaporated to dryness. The crude product was purified by recrystallization from DCM/n-hexane to obtain {5,10,15-tris-(3-hydroxyphenyl)-20-[2,3,5,6-tetrafluoro-4-(N-(2-((2-aminoethyl)disulfanyl)ethyl propiol-amido))phenyl]porphyrinato}-zinc(II) (58.0 mg, 58.0 mol, 97% yield) as a pink solid.

{5,10,15-Tris(3-hydroxyphenyl)-20-[2,3,5,6-tetrafluoro-4-(N-(2-((2-aminoethyl)disulfanyl)ethyl propiolamido))phenyl]porphyrinato}-zinc(II)

$^1$H NMR ([D6]Acetone, 700 MHz): δ (ppm)=9.02 (d, $^3$J(H,H)=4.5 Hz, 2H, 2.18-β), 8.98 (d, $^3$J(H,H)=4.5 Hz, 2H, 3.17-β), 8.95 (d, $^3$J(H,H)=4.5 Hz, 2H, 6.13-β), 8.94 (d, $^3$J(H,H)=4.5 Hz, 2H, 8.12-β), 8.88 (bs, 3H, 5,10,15-meso-3-Ar—OH), 8.08 (bs, 1H, NHC(O)), 7.72 (s, 3H, 5,10,15-meso-2-Ar), 7.69 (d, $^3$J(H,H)=7.2 Hz, 3H, 5,10,15-meso-6-Ar), 7.62-7.57 (m, 3H, 5,10,15-meso-5-Ar), 7.29 (dd, $^3$J(H,H)=8.6, $^4$J(H,H)=2.6 Hz, 3H, 5,10,15-meso-4-Ar), 5.79 (t, $^3$J(H,H)=6.6 Hz, 1H, Ar$_F$—NHCH$_2$), 4.01 (q, $^3$J(H,H)=6.8 Hz, 2H, Ar$_F$—NHCH$_2$CH$_2$), 3.67 (q, $^3$J(H,H)=6.5 Hz, 2H, CH$_2$NHC(O)), 3.52 (s, 1H, CCH), 3.25 (t, $^3$J(H,H)=6.7 Hz, 2H, Ar$_F$—NHCH$_2$CH$_2$), 3.01 (t, $^3$J(H,H)=6.8 Hz, 2H, CH$_2$CH$_2$NHC(O)). $^{13}$C NMR ([D6]Acetone, 176 MHz): δ (ppm)=156.55, 156.53, 152.90, 151.18, 151.11, 150.84, 150.62, 148.56, 147.21, 145.40, 145.34, 138.87, 137.53, 133.45, 132.63, 132.33, 131.05, 129.33, 128.19, 128.17, 127.22, 122.89, 122.67, 121.69, 115.38, 109.95, 103.56, 78.67, 74.46, 45.49, 39.56, 39.42, 37.94. $^{19}$F NMR ([D6]Acetone, 376 MHz): δ (ppm)=142.72 (d, $^3$J(F,F)=21.3 Hz, 2F, m-Ar$_F$), −161.99 (−162.12) (m, 2F, o-Ar$_F$). m.p.: >230° C. HRMS (ESI): calc. for $C_{51}H_{34}F_4N_6O_4S_2Zn^+$ ([M]$^+$): 998.1311 found: 998.1294. UV/Vis (ethanol): λ$_{max}$(ε)=597 (5000), 556 (18 000), 423 nm (411 000).

1.11 (2-(2-Methoxy-4-(3-((5aS,6R,6aR)-6-((((6-((2, 3,5,6-tetrafluoro-4-(10,15,20-tris(3-hydroxyphenyl) porphyrin-5-yl)phenyl)amino)hexyl)carbamoyl)oxy) methyl)-5,5a,6,6a,7,8-hexahydrocyclopropa[5,6] cycloocta[1,2-d][1,2,3]triazol-1(4H)-yl)propoxy) phenyl)-1,3-dioxolan-4-yl)-hPG$_{9.1}$ with 6 Porphyrin Groups (MS154/BLC 4176)

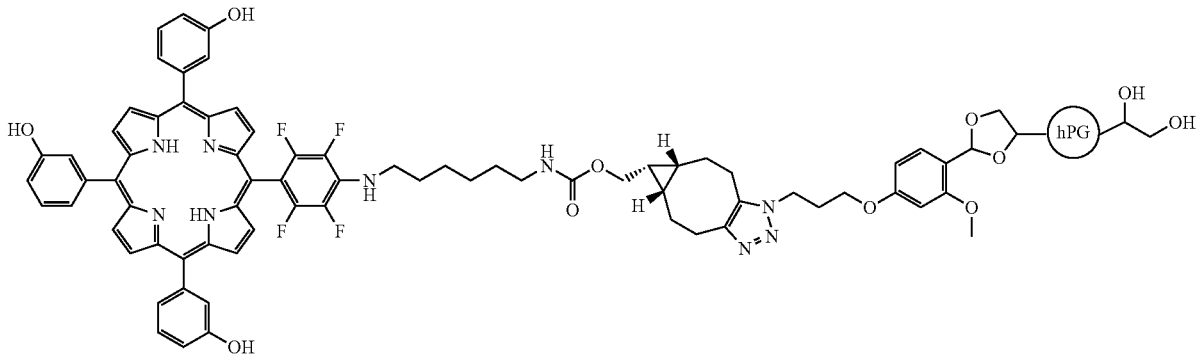

In a 5 ml flask with magnetic stirrer hPG$_{9.1}$-acetal-azide with 6% azide groups (23.0 mg, 2.07 mol, 20.7 µmol azide groups) was dissolved in 1 ml of dry DMSO (Acros) basified with 0.1% v/v NEt$_3$. 5,10,15-Tris(3-hydroxyphenyl)-20-[2, 3,5,6-tetrafluoro-4-(N-((1R,8S,9s,Z)-bicyclo [6.1.0]non-4-in-9-yl)methylcarbonyl)hexylamino)phenyl]-porphyrin (22.7 mg, 22.1 µmol) was added and the solution was stirred at RT for 1 d. The crude product was purified by dialysis in acetone/H$_2$O (9:1)+0.1% v/v NEt$_3$ for 3 d to obtain the purple product (2-(2-methoxy-4-(3-((5aS,6R,6aR)-6-((((6-((2,3,5,6-tetrafluoro-4-(10,15,20-tris (3-hydroxyphenyl)porphyrin-5-yl)phenyl)amino)hexyl)carbamoyl)oxy)methyl)-5,5a,6,6a,7,8-hexahydrocyclopropa[5,6]cycloocta[1,2-d][1,2,3]triazol-1(4H)-yl)propoxy)phenyl)-1,3-dioxolan-4-yl)-hPG$_{9.1}$ with 6 porphyrin groups (36.0 mg, 2.07 mol, 13.0 µmol porphyrin groups, quant. yield, 63% conversion).

(2-(2-Methoxy-4-(3-((5aS,6R,6aR)-6-((((6-((2,3,5,6-tetrafluoro-4-(10,15,20-tris(3-hydroxyphenyl)porphyrin-5-yl)phenyl)amino)hexyl)carbamoyl)oxy) methyl)-5,5a,6,6a,7,8-hexahydrocyclopropa[5,6] cycloocta[1,2-d][1,2,3]triazol-1(4H)-yl)propoxy) phenyl)-1,3-dioxolan-4-yl)-hPG$_{9.1}$ with 6 Porphyrin Groups $^1$H NMR ([D8]THF/D$_2$O (9:1), 700 MHz): δ (ppm)=9.02-8.86 (m, β), 7.72-7.18 (m, Ar+triazole-H), 6.46-6.18 (m, Ar), 6.14-5.90 (m, acetal-H), 5.14-3.23 (m, hPG-backbone+ CH$_2$), 2.14-1.82 (m, CH$_2$), 1.52-1.27 (m, CH$_2$, CH), 2.72 (s, pyrrole-NH). $^{13}$C NMR ([D8]THF/D$_2$O (9:1), 176 MHz): δ (ppm)=161.57, 159.95, 157.68, 157.26, 148.70, 147.34, 144.55, 144.07, 138.57, 137.20, 133.76, 130.55, 129.10, 128.33, 127.04, 123.07, 122.35, 121.42, 115.86, 107.53, 105.89, 103.61, 100.01, 99.79, 99.34, 81.29, 79.54, 75.80, 73.93, 72.86, 72.17, 71.96, 70.60, 70.31, 65.32, 64.49, 62.72, 62.41, 56.04, 46.41, 45.02, 41.53, 41.41, 31.95, 30.97, 30.31, 27.43, 26.47, 23.15, 22.29, 20.47, 19.83, 18.60.

1.12 ((5aR,6S,6aS)-1-(3-(4-(4-Ethyl-1,3-dioxolan-2-yl)phenoxy)propyl)-1,4,5,5a,6,6a,7,8-octahydrocyclopropat-[5,6]-cycloocta-[1,2-d]-[1,2,3]triazol-6-yl) methyl-(6-((2,3,5,6-tetrafluor-4-(10,15,20-tris-(3-hydroxyphenyl)porphyrin-5-yl)phenyl)-amino) hexyl)carbamat-hPG$_{19.5}$ with 11 Porphyrin Groups

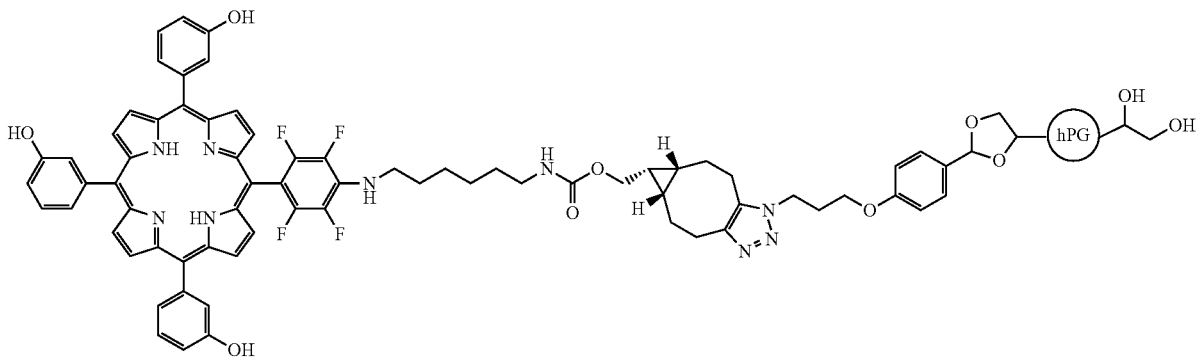

In a 25 ml two-necked flask with magnetic stirrer hPG$_{19.5}$-acetal-azide with 17 azide groups (28.7 mg, 1.25 µmol, 21.2 µmol azide groups) was dissolved in 2 ml of dry DMSO (Acros). 5,10,15-Tris(3-hydroxyphenyl)-20-[2,3,5,6-tetrafluoro-4-(N-((1R,8S,9s,Z)-bicyclo[6.1.0]non-4-in-9-yl)methylcarbonyl)hexylamino)phenyl]-porphyrin (37.4 mg, 36.5 µmol) was added and the solution was stirred at RT for 64 h. The crude product was purified by dialysis in THF+0.05 wt % aqueous ammonia for 3 d to obtain the purple product ((5aR,6S,6aS)-1-(3-(4-(4-ethyl-1,3-dioxolan-2-yl)phenoxy)propyl)-1,4,5,5a,6,6a,7,8-octahydrocyclopropa-[5,6]-cycloocta-[1,2-d]-[1,2,3]triazol-6-yl)methyl-(6-((2,3,5,6-tetrafluor-4-(10,15,20-tris-(3-hydroxyphenyl)porphyrin-5-yl)phenyl)-amino)-hexyl)carbamat-hPG$_{19.5}$ with 11 porphyrin groups (37.4 mg, 1.09 mol, 12.0 µmol porphyrin groups, 87% yield, 65% conversion).

((5aR,6S,6aS)-1-(3-(4-(4-Ethyl-1,3-dioxolan-2-yl)phenoxy)propyl)-1,4,5,5a,6,6a,7,8-octahydrocyclopropa-[5,6]-cycloocta-[1,2-d]-[1,2,3]triazol-6-yl)methyl-(6-((2,3,5,6-tetrafluor-4-(10,15,20-tris-(3-hydroxyphenyl)porphyrin-5-yl)phenyl)-amino)hexyl)carbamat-hPG$_{19.5}$ with 11 Porphyrin Groups $^1$H NMR ([D8]THF, 700 MHz): δ (ppm)=9.02-8.81 (m, (3), 7.68-7.57 (m, Ar), 7.48 (bs, Ar), 7.17 (bs, Ar+triazole-H), 6.55 (bs, Ar), 6.22 (bs, Ar), 5.81-5.43 (m, acetal-H), 5.24-3.19 (m, hPG-backbone+porphyrin), 3.03 (bs, porphyrin), 2.03-1.64 (m, porphyrin), 1.56-1.16 (m, porphyrin), 1.03-0.80 (m, porphyrin). $^{13}$C NMR ([D8]THF, 176 MHz): δ (ppm)=157.66, 157.25, 148.68, 147.35, 144.51, 144.06, 138.62, 137.28, 128.76, 128.34, 127.11, 123.12, 121.42, 115.78, 114.66, 108.44, 98.80, 81.31, 79.54, 75.94, 74.01, 72.95, 72.21, 71.98, 70.70, 70.36, 68.27, 64.57, 46.60, 44.97, 41.51, 34.22, 31.95, 31.00, 30.36, 30.00, 27.42, 23.18, 20.48. $^{19}$F NMR ([D8]THF, 376 MHz): δ (ppm)=143.57 (−144.19) (s, m-Ar-F); 163.42 (−164.26) (m, o-Ar—F).

1.13 ((5aR,6S,6aS)-1-(3-(4-(4-Ethyl-1,3-dioxolan-2-yl)phenoxy)propyl)-1,4,5,5a,6,6a,7,8-octahydrocyclopropat-[5,6]-cycloocta-[1,2-d]-[1,2,3]-triazol-6-yl)-methyl-((6-((2,3,5,6-tetrafluor-4-(10,15,20-tris-(3-hydroxyphenyl)porphyrin-5-yl)phenyl)-amino)disulfanyl)ethylamino)carbamat-hPG$_{19.5}$ with 15 Porphyrin Groups In a 25 ml two-necked flask with magnetic stirrer hPG$_{19.5}$-acetal-azide with 17 azide groups (19.6 mg, 852 nmol, 14.5 µmol azide groups) was dissolved in 2 ml of dry DMSO (Acros). 5,10,15-Tris(3-hydroxyphenyl)-20-[4-((2-(2-(((((1R,8S,9s)-bicyclo [6.1.0]non-4-yn-9-yl)methoxy)carbonyl)amino)ethyl)disulfanyl)ethyl)amino)tetrafluorophenyl]-porphyrin (26.4 mg, 24.9 µmol) was added and the solution was stirred at RT for 64 h. The crude product was purified by dialysis in THF+0.05 wt % aqueous ammonia for 3 d to obtain the purple product ((5aR,6S,6aS)-1-(3-(4-(4-Ethyl-1,3-dioxolan-2-yl)phenoxy)propyl)-1,4,5,5a,6,6a,7,8-octahydrocyclopropa-[5,6]-cycloocta[1,2-d]-[1,2,3]-triazol-6-yl)-methyl-((6-((2,3,5,6-tetrafluor-4-(10,15,20-tris-(3-hydroxyphenyl)-porphyrin-5-yl)phenyl)-amino)disulfanyl)ethylamino)carbamat-hPG$_{19.5}$ with 15 porphyrin groups (29.6 mg, 760 nmol, 11.4 µmol porphyrin groups, 89% yield, 88% conversion).

((5aR,6S,6aS)-1-(3-(4-(4-Ethyl-1,3-dioxolan-2-yl)phenoxy)propyl)-1,4,5,5a,6,6a,7,8-octahydrocyclopropa-[5,6]-cycloocta-[1,2-d]-[1,2,3]-triazol-6-yl)-methyl-6-((2,3,5,6-tetrafluor-4-(10,15,20-tris-(3-hydroxyphenyl)porphyrin-5-yl)phenyl)-amino)-disulfanyl)ethylamino)carbamat-hPG$_{19.5}$ with 15 Porphyrin Groups $^1$H NMR ([D8]THF, 700 MHz): δ (ppm)=9.03-8.77 (m, β), 7.67-7.56 (m, Ar), 7.47 (bs, Ar), 7.21-7.03 (m, Ar+triazole-H), 6.66-6.36 (m, Ar), 6.02-5.83 (m, acetal-H), 4.87-2.97 (m, hPG-backbone+porphyrin), 2.95-2.64 (m, porphyrin), 1.98-1.65 (m, porphyrin) 1.41-1.19 (m, porphyrin), 1.00-0.79 (m, porphyrin), 2.75 (m, pyrrole-NH). $^{13}$C NMR ([D8]THF, 176 MHz): δ (ppm)=157.68, 157.23, 148.72, 147.33, 144.47, 144.04, 138.77, 137.42, 128.76, 128.34, 127.12, 123.11, 121.43, 115.78, 114.62, 108.44, 98.80, 81.18, 79.63, 76.02, 73.94, 72.80, 72.21, 71.99, 70.83, 70.34, 65.06, 64.56, 62.76, 45.60, 44.95, 41.04, 39.98, 39.21, 34.22, 30.21, 30.00, 23.13, 20.39. $^{19}$F NMR ([D8]THF, 376 MHz): δ (ppm)=143.55 (−143.77) (m, —Ar—F), 163.11 (−163.31) (m, o-Ar—F).

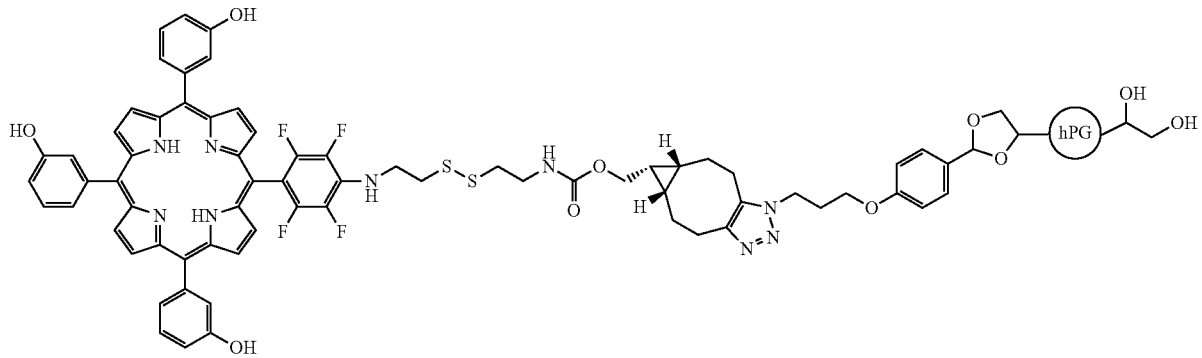

1.14 5,10,15-Tris(3-hydroxyphenyl)-20-[4-((2-((2-(((((1R,8S,9r)-bicyclo[6.1.0]non-4-yn-9-yl)methoxy)carbonyl)amino)ethyl)disulfanyl)ethyl)amino)tetrafluoro-phenyl]porphyrin-hPG$_{19.5}$-azide with 3.2% Porphyrin and 9.8% Azide Groups (MS109/BLC 3171)

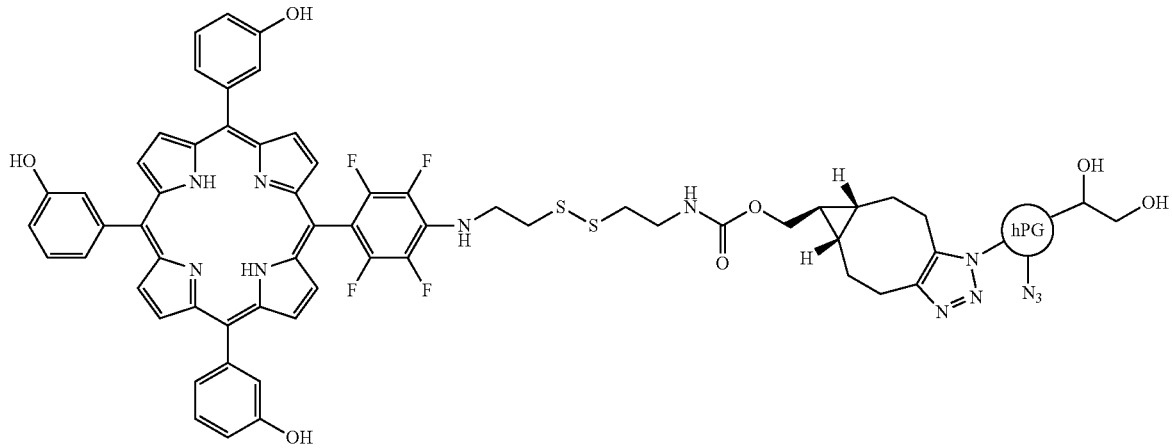

In a 5 ml flask with magnetic stirrer hPG$_{19.5}$-azide with 13% azide groups (43.6 mg, 2.14 μmol, 73.3 μmol azide groups) was dissolved in 1 ml of dry DMSO (Acros). 5,10,15-Tris(3-hydroxyphenyl)-20-[4-((2-(2-(((((1R,8S,9r)-bicyclo[6.1.0]non-4-yn-9-yl)-methoxy)carbonyl)amino)ethyl)disulfanyl)ethyl)amino)tetrafluorophenyl]porphyrin (20.1 mg, 18.9 μmol) was added and the solution was stirred at RT for 1 h. The crude product was purified by dialysis in acetone/H$_2$O (4:1) for 3 d to obtain the purple product 5,10,15-tris(3-hydroxyphenyl)-20-[4-((2-(2-(((((1R,8S,9r)-bicyclo [6.1.0]non-4-yn-9-yl)-methoxy)carbonyl)amino)ethyl)disulfanyl)ethyl)amino)tetrafluorophenyl)porphyrin-hPG$_{19.5}$-azide with 3.2% porphyrin and 9.8% azide groups (58.0 mg, 1.98 μmol, 16.7 μmol porphyrin and 51.1 μmol azide groups, 92% yield, 96% conversion).

5,10,15-Tris(3-hydroxyphenyl)-20-[4-2-((2-(((((1R, 8S,9r)-bicyclo[6.1.0]non-4-yn-9-yl)methoxy)carbonyl)amino)ethyl)disulfanypethyl)amino)tetrafluorophenyl]porphyrin-hPG$_{19.5}$-azide with 3.2% Porphyrin and 9.8% Azide Groups $^1$H NMR ([D6]Acetone/D$_2$O (6:1), 700 MHz): δ (ppm)= 8.89 (bs, β), 7.72-7.08 (m, Ar+triazole-H), 5.56-4.91 (m, meso-NH), 4.03-3.04 (m, hPG-backbone+cystamine-CH$_2$), 2.92-1.76 (m, cystamine-CH$_2$+cyclooctyne-CH$_2$), 1.31-0.06 (m, cyclooctyne-CH), −2.86 (s, pyrrole-NH). $^{13}$C NMR ([D6]Acetone/D$_2$O (6:1), 176 MHz): δ (ppm)=157.71, 156.29, 148.10, 146.75, 144.65, 143.35, 143.20, 138.41, 137.06, 135.30, 129.60, 128.39, 126.77, 122.40, 122.08, 121.10, 115.69, 107.67, 103.16 (porphyrin); 80.59, 80.41, 79.07, 78.81, 73.09, 71.95, 71.47, 71.23, 69.96, 69.64, 63.47, 61.68, 53.94 (hPG); 51.94, 50.71, 44.79, 40.23, 39.35, 38.52, 27.37, 26.62, 25.32, 24.40, 22.66 (porphyrin).

1.15 5,10,15-Tris(3-hydroxyphenyl)-20-[4-((2-((2-(((((1R,8S,9r)-bicyclo[6.1.0]non-4-yn-9-yl)methoxy)carbonyl)amino)ethyl)disulfanypethyl)amino)tetrafluorophenyl]-porphyrin-hPG$_{19.5}$-mannose-azide with 6.3% Porphyrin, 38% Mannose and 35.7% Azide Groups (MS153/BLC 4161)

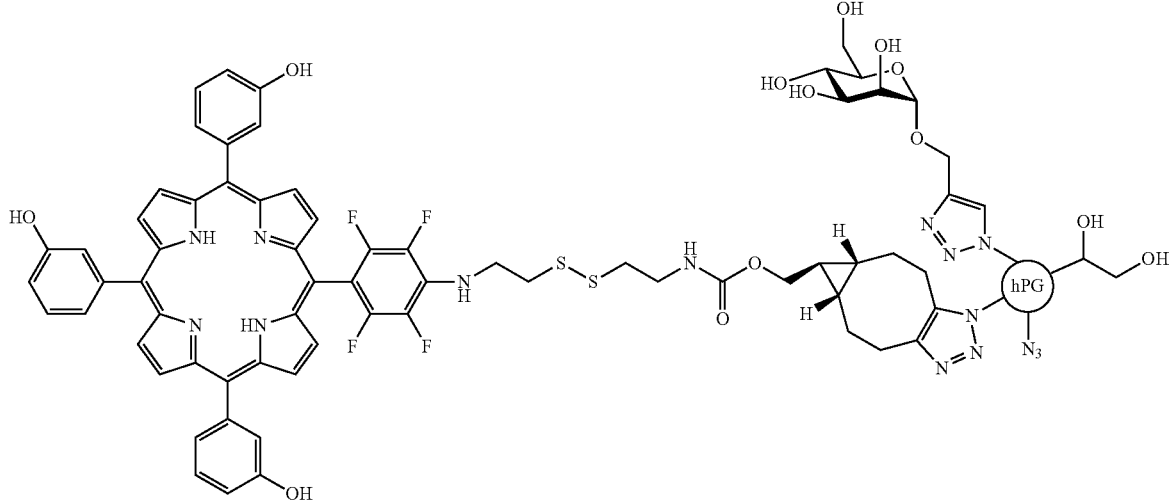

In a 5 ml flask with magnetic stirrer hPG$_{19.5}$-mannose-azide with 38% mannose and 42% azide groups (18.1 mg, 388 nmol, 38.9 µmol mannose and 43.0 µmol azide groups) was dissolved in 1 ml of dry DMSO (Acros). 5,10,15-Tris(3-hydroxyphenyl)-20-[4-((2-((2-(((((1R,8S,9r)-bicyclo[6.1.0]non-4-yn-9-yl)methoxy)carbonyl)amino)ethyl)disulfanyl)-ethyl)amino)tetrafluorophenyl]porphyrin (12.2 mg, 11.5 µmol) was added and the solution was stirred at RT for 1 d. The crude product was purified by dialysis in acetone for 3 d to obtain the purple product 5,10,15-tris(3-hydroxyphenyl)-20-[4-((2-((2-(((((1R,8S,9r)-bicyclo[6.1.0]non-4-yn-9-yl)methoxy)carbonyl)amino)ethyl)disulfanyl)-ethyl)amino)tetrafluorophenyl)porphyrin-hPG$_{19.5}$-mannose-azide with 6.3% porphyrin, 38% mannose and 35.7% azide groups (24.9 mg, 388 nmol, 6.44 µmol porphyrin, 38.9 mannose and 36.5 µmol azide groups, quant. yield, 56% conversion).

5,10,15-Tris(3-hydroxyphenyl)-20-[4-((2(2-(((((1R,8S,9s)-)-bicyclo[6.1.0]non-4-yn-9-yl)methoxy)carbonyl)amino)ethyl)disulfanypethyl)amino)tetrafluorophenyl]porphyrin-hPG$_{19.5}$-mannose-azide with 6.3% Porphyrin, 38% Mannose and 35.7% Azide Groups $^1$H NMR ([D6]Acetone/D$_2$O (85:15), 700 MHz): δ (ppm)= 8.87 (bs, (3), 7.78-6.97 (m, Ar+porphyrin/Man-triazole-H), 5.78-2.35 (m, Man: H-1, H-2, H-3, H-4, H-5, H-6, —OCH$_2$; hPG backbone; cystamine-CH$_2$+cyclooctyne-CH$_2$). $^{13}$C NMR ([D6]Acetone/D$_2$O (85:15), 176 MHz): δ (ppm)=157.49, 156.37, 148.19, 146.72, 144.55, 143.22, 138.45, 137.02, 129.47, 128.33, 126.78, 122.49, 122.11, 121.13, 115.68, 107.66, 103.21, 99.75, 73.97, 71.71, 71.01, 67.72, 61.94, 59.91, 55.49, 44.72, 40.18, 39.12, 38.42.

1.16 {5,10,15-Tris(3-hydroxyphenyl)-20-[2,3,5,6-tetrafluoro-4-N-((2-((2-(1H-1,2,3-triazol-4-yl-carboxamido)ethyl)-disulfanyl)ethyl)aminophenyl)]porphyrinato}-zinc(II)-hPG$_{19.5}$-azide with 0.6% Porphyrin Zinc(II) Complex and 1.4% Azide Groups In a 10 ml flask with magnetic stirrer hPG$_{19.5}$-azide with 2% azide groups (68.0 mg, 3.49 µmol, 18.4 µmol azide groups) was dissolved in 1 ml of DMSO (Roth). {5,10,15-Tris-(3-hydroxyphenyl)-20-[2,3,5,6-tetrafluoro-4-(N-(24(2-aminoethyl)disulfanyl)ethyl propiol-amido))phenyl]porphyrinato}-zinc(II) (20.0 mg, 20.0 µmol), L-ascorbic acid sodium salt (40.0 µl, 50 mM in 40 µl H$_2$O, 2.00 µmol) and copper(II) sulfate hydrate (50 µl, 40 mM in H$_2$O, 2.00 µmol) were added and the solution was stirred at RT for 1 d. The crude product was purified by dialysis in acetone/H$_2$O (4:1) for 2 d to obtain the purple honey-like product {5,10,15-tris(3-hydroxyphenyl)-20-[2,3,5,6-tetrafluoro-4-N-((2-((2-(1H-1,2,3-triazol-4-yl-carboxamido)ethyl)disulfanyl)ethyl)aminophenyl)]porphyrinato}-zinc(II)-hPG$_{19.5}$-azide with 0.6% porphyrin zinc(II) complex and 1.4% azide groups (71 mg, 3.38 µmol, 5.34 µmol porphyrin and 12.5 µmol azide groups, 97% yield, 28% conversion).

{5,10,15-Tris(3-hydroxyphenyl)-20-[2,3,5,6-tetrafluoro-4-N-((2-((2-(1H-1,2,3-triazol-4-yl-carboxamido)ethyl)-disulfanyl)ethyl)aminophenyl)]porphyrinatog-zinc(II)-hPG$_{19.5}$-azide with 0.6% Porphyrin Zinc(II) Complex and 1.4% Azide Group $^1$H NMR (D$_2$O, 700 MHz): δ (ppm)=9.33-8.75 (m, β), 8.08-7.16 (m, Ar+triazole-H), 4.14-3.18 (m, hPG backbone+cystamine-CH$_2$), 1.42 (CH$_2$-hPG starter unit), 0.92 (CH$_3$-hPG starter unit). $^{13}$C NMR (D$_2$O, 176 MHz): δ (ppm)= 154.71, 150.15, 144.00, 132.50, 128.00, 122.18, 114.94, 103.45 (porphyrin); 79.66, 79.44, 78.18, 77.93, 72.15, 70.89, 70.72, 70.43, 69.19, 68.89, 62.62, 60.77, 53.13 (hPG). UV/Vis (acetone/H$_2$O 4:1): $\lambda_{max}$=598, 557, 424 nm.

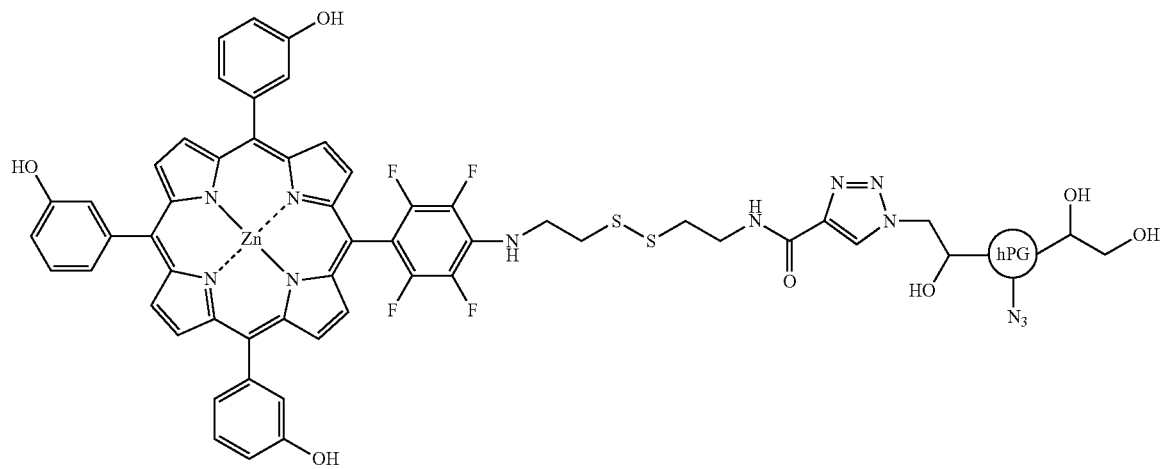

1.17 5,10,15-Tris(3-hydroxyphenyl)-20-[4-(prop-2-yn-1-ylamino))tetrafluoro-phenyl]porphyrin

1.18 {5,10,15-Tris(3-hydroxyphenyl)-20-[4-(prop-2-yn-1-ylamino))tetrafluoro-phenyl]porphyrinato}-zinc(II)

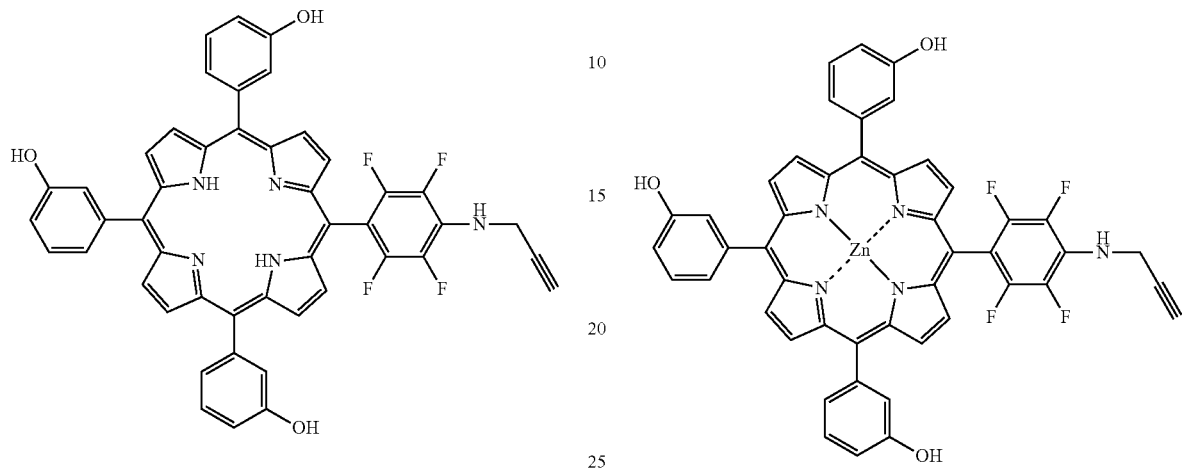

In a 10 ml flask with magnetic stirrer 5,10,15-tris(3-acetoxyphenyl)-20-pentafluorophenylporphyrin (203 mg, 231 μmol) was dissolved in 2 ml dry DMSO (Roth) under argon. Propargylamine (98%, 300 μl, 258 mg, 4.59 mmol) was added and the solution was stirred at 83° C. for 3 h. The crude product was diluted with 150 ml of ethyl acetate and washed three times with 30 ml H$_2$O. Afterwards the organic layer was dried over Na$_2$SO$_4$. The crude product was evaporated to dryness and the remaining residue was purified by column chromatography (DCM/acetone 9:1, Machery-Nagel) and recrystallization from DCM/n-hexane to obtain 5,10,15-tris(3-hydroxyphenyl)-20-[4-(prop-2-yn-1-ylamino))tetrafluorophenyl]porphyrin (170 mg, 216 μmol, 94% yield) as a purple solid.

5,10,15-Tris(3-hydroxyphenyl)-20-[4-(prop-2-yn-1-ylamino))tetrafluorophenyl]-porphyrin $^1$H NMR ([D6]Acetone, 500 MHz): δ=9.13-9.06 (m, 2H, 2.18-β), 9.03 (d, $^3$J(H,H)=4.8 Hz, 2H, 3.17-β), 8.97 (bs, 4H, 7,8,12,13-β), 8.87 (s, 3H, 5,10,15-meso-3-Ar—OH), 7.77 (t, $^4$J(H,H)=2.0 Hz, 2H, 5.15-meso-2-Ar), 7.76-7.71 (m, 4H, 10-meso-2-Ar+5,10,15-meso-6-Ar), 7.66-7.61 (m, 3H, 5,10,15-meso-5-Ar), 7.36-7.32 (m, 3H, 5,10,15-meso-4-Ar), 6.15 (t, $^3$J(H,H)=7.2 Hz, 1H, Ar$_F$—NH), 4.49-4.46 (m, 2H, CH$_2$), 2.98 (t, $^4$J(H,H)=2.5 Hz, 1H, C≡CH), −2.75 ppm (s, 2H, pyrrole-NH). $^{13}$C NMR ([D6]Acetone, 126 MHz): δ=156.83, 156.78, 148.78, 146.83, 143.97, 143.82, 139.72, 137.82, 132.39, 129.38, 128.70, 128.65, 127.27, 127.23, 122.88, 122.84, 122.42, 121.45, 116.00, 109.58, 103.30, 81.88, 73.55, 35.75 ppm. $^{19}$F NMR ([D6]Acetone, 471 MHz): δ=−142.99 (d, $^3$J(F,F)=20.5 Hz, 2F, m-Ar$_F$), 160.83 ppm (d, $^3$J(F,F)=19.3 Hz, 2F, o-Ar$_F$). m.p.: 135° C. HRMS (ESI): calc. for C$_{47}$H$_{30}$F$_4$N$_5$O$_3^+$ ([M+H]$^+$): 788.2285 found: 788.2270. UV/Vis (ethanol): λ$_{max}$(ε)=645 (3000), 589 (5000), 546 (6000), 512 (17 000), 416 nm (283 000).

In a 25 ml flask with magnetic stirrer 5,10,15-tris(3-hydroxyphenyl)-20-[4-(prop-2-yn-1-ylamino))tetrafluoro-phenyl]porphyrin (181 mg, 230 μmol) was dissolved in 10 ml of methanol. A point of a spatula of sodium acetate and zinc acetate dihydrate (506 mg, 2.31 mmol) were added to the stirring solution. The solution was stirred for 1 h at RT. The crude product was diluted with 150 ml ethyl acetate and washed three times with 50 ml of H$_2$O. Afterwards the organic layer was dried over Na$_2$SO$_4$ and the solution was evaporated to dryness. The crude product was purified by recrystallization from DCM/n-hexane to obtain {5,10,15-tris(3-hydroxyphenyl)-20-[4-(prop-2-yn-1-ylamino))tetra-fluorophenyl]porphyrinato}-zinc(II) (186 mg, 219 mol, 95% yield) as a pink solid.

{5,10,15-Tris(3-hydroxyphenyl)-20-[4-(prop-2-yn-1-ylamino))tetrafluorophenyl]-porphyrinato}-zinc(II)

$^1$H NMR ([D6]Acetone, 400 MHz): δ=8.99 (s, 4H, 2,3, 17,18-β), 8.97-8.91 (m, 4H, 7,8,12,13-β), 8.87 (bs, 3H, 5,10,15-meso-3-Ar—OH), 7.76-7.71 (m, 6H, 5,10,15-meso-2,6-Ar), 7.58 (t, $^3$J(H,H)=7.8 Hz, 3H, 5,10,15-meso-5-Ar), 7.287 (dd, $^3$J(H,H)=8.2 Hz; $^4$J(H,H)=1.2 Hz, 2H, 5.15-meso-4-Ar), 7.281 (dd, $^3$J(H,H)=8.1 Hz; $^4$J(H,H)=1.0 Hz, 1H, 10-meso-4-Ar), 6.04-5.94 (m, 1H, Ar$_F$—NH), 4.43-4.36 (m, 2H, CH$_2$), 2.95 ppm (t, $^4$J(H,H)=2.4 Hz, 1H, C≡CH). $^{13}$C NMR ([D6]Acetone, 126 MHz): δ=156.54, 156.51, 151.17, 151.05, 150.86, 150.69, 148.70, 146.81, 145.32, 145.25, 139.76, 137.84, 133.58, 132.74, 132.44, 130.93, 128.78, 128.73, 128.28, 128.25, 127.29, 122.91, 122.81, 121.82, 115.44, 111.25, 103.43, 81.91, 73.53, 35.81 ppm. $^{19}$F NMR ([D6]Acetone, 471 MHz): δ=−142.68 (d, $^3$J(F,F)=22.9 Hz, 2F, m-Ar$_F$), −160.99 ppm (d, $^3$J(F,F)=20.7 Hz, 2F, o-Ar$_F$). m.p.: >230° C. HRMS (ESI): calc. for C$_{47}$H$_{27}$F$_4$N$_5$O$_3$Zn$^+$ ([M]$^+$): 849.1341 found: 849.1331. UV/Vis (ethanol): λ$_{max}$(ε)=597 (5000), 556 (20 000), 423 nm (435 000).

1.19 5,10,15-Tris(3-hydroxyphenyl)-20-[4-((6-(((((1R,8S,9s)-bicyclo[6.1.0]non-4-yn-9-yl)methoxy)carbonyl)amino)hexyl)amino)tetrafluorophenyl]porphyrin

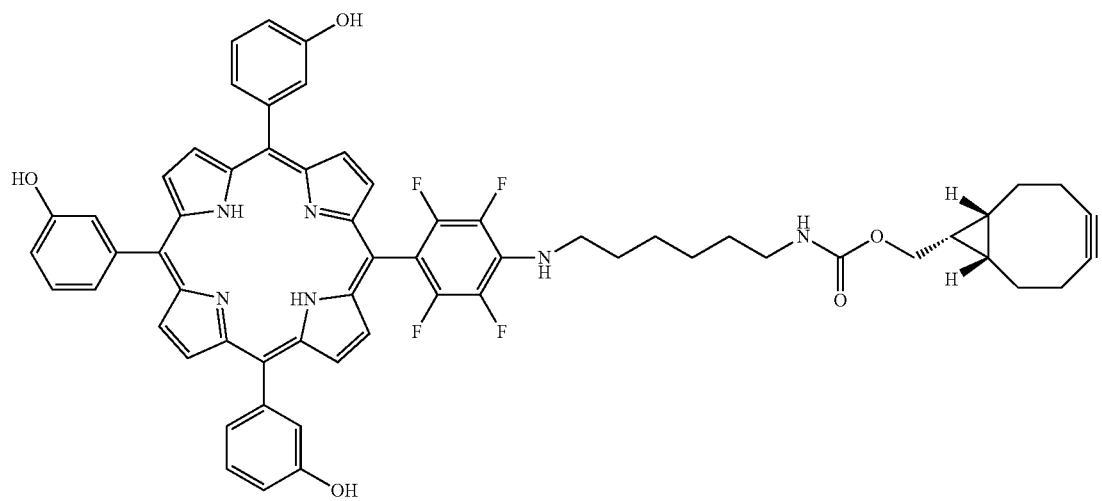 [SMILES: O=C(NCCCCCCNc1c(F)c(F)c(-c2c3nc(c(-c4cccc(O)c4)c4ccc([nH]4)c(-c4cccc(O)c4)c4nc(c(-c5cccc(O)c5)c5ccc2[nH]5)C=C4)C=C3)c(F)c1F)OC[C@@H]1[C@@H]2CCC#CCC[C@@H]21]

In a 25 ml flask with magnetic stirrer (1R,8S,9s)-bicyclo[6.1.0]non-4-yn-9-ylmethyl (4-nitrophenyl) carbonate endo (75.2 mg, 238 μmol) was dissolved in 3.5 ml of anhydrous DMF under argon. To the stirring solution 5,10,15-tris(3-hydroxyphenyl)-20-[6-amino-hexylamino)tetrafluorophenyl]porphyrin (146 mg, 172 μmol) and NEt$_3$ (99%, 8.62 μl, 6.29 mg, 61.5 μmol) were added. The solution was stirred for 15 min at RT. The crude product was diluted with 50 ml of ethyl acetate and washed four times with 30 ml of H$_2$O. Afterwards the organic layer was dried over Na$_2$SO$_4$. The crude product was evaporated to dryness and the remaining residue was purified by column chromatography (DCM/methanol 96:4, Fluka) to obtain 5,10,15-tris(3-hydroxyphenyl)-20-[4-((6-(((((1R,8S,9s)-bicyclo [6.1.0]non-4-yn-9-yl)methoxy)carbonyl)amino)hexyl)amino)tetrafluorophenyl]porphyrin (150 mg, 146 μmol, 88% yield) as a purple solid.

5,10,15-Tris(3-hydroxyphenyl)-20-[4-((6-(((((1R,8S,9s)-bicyclo[6.1.0]non-4-yn-9-yl)-methoxy)carbonyl)amino)hexyl)amino)tetrafluorophenyl]porphyrin $^1$H NMR ([D6]Acetone, 700 MHz): δ=9.10 (bs, 2H, 2.18-β), 9.05-8.99 (m, 2H, 3.17-β), 8.96 (bs, 4H, 7,8,12,13-β), 8.82 (s, 3H, 5,10,15-meso-3-Ar—OH), 7.76 (bs, 2H, 5,15-meso-2-Ar), 7.740 (d, $^3$J(H,H)=8.7 Hz, 3H, 10-meso-2-Ar+5,15-meso-6-Ar), 7.728 (d, $^3$J(H,H)=8.6 Hz, 3H, 10-meso-6-Ar), 7.637 (dd, $^3$J(H,H)=8.4 Hz, $^3$J(H,H)=7.2 Hz, 2H, 5,15-meso-5-Ar), 7.631 (dd, $^3$J(H,H)=8.4 Hz, $^3$J(H,H)=7.2 Hz, 1H, 10-meso-5-Ar), 7.338 (dd, $^3$J(H,H)=8.5 Hz, $^4$J(H,H)=2.4 Hz, 1H, 10-meso-4-Ar), 7.337 (dd, $^3$J(H,H)=8.5 Hz, $^4$J(H,H)=2.5 Hz, 1H, 5,15-meso-4-Ar), 6.19 (bs, 1H, C(O)NH), 5.65 (bs, 1H, Ar$_F$—NH), 4.09 (d, $^3$J(H,H)=8.1 Hz, 2H, OCH$_2$), 3.71 (q, $^3$J(H,H)=7.2 Hz, 2H, Ar$_F$—NHCH$_2$), 3.19 (q, $^3$J(H,H)=6.9 Hz, 2H, C(O)NHCH$_2$), 2.21-2.13 (m, 4H, 3,6-Bicyclo), 2.11-2.06 (m, 2H, 2,7-Bicyclo), 1.88 (q, $^3$J(H,H)=7.3 Hz, 2H, Ar$_F$—NHCH$_2$CH$_2$), 1.64-1.47 (m, 8H, C(O)NHCH$_2$CH$_2$CH$_2$CH$_2$+2,7-Bicyclo), 1.31 (p, $^3$J(H,H)=8.9 Hz, 2H, 9-Bicyclo), 0.89-0.81 (m, 2H, 1,8-Bicyclo), -2.74 (s, 2H, pyrrole-NH). $^{13}$C NMR ([D6]Acetone, 176 MHz): δ=157.54, 156.82, 156.77, 156.72, 156.67, 148.61, 147.26, 143.99, 143.86, 138.66, 137.31, 130.63, 128.68, 128.63, 127.26, 127.22, 122.88, 122.84, 122.29, 121.36, 115.98, 115.90, 107.39, 103.77, 99.32, 62.33, 46.36, 41.38, 31.64, 30.86, 30.31, 27.23, 27.19, 21.69, 20.84, 18.77. $^{19}$F NMR ([D6]Acetone, 471 MHz): δ=-143.28-(-143.56) (m, 2F, m-Ar$_F$), -162.56 ppm (d, $^3$J(F,F)=16.3 Hz, 2F, o-Ar$_F$). m.p.: 111° C. UV/Vis (acetone): λ$_{max}$ (ε)=644 (3020), 589 (5550), 545 (7080), 512 (20 000), 416 (316 000).

1.20 General Synthesis of {5,10,15-tris(3-hydroxyphenyl)-20-[4-(N-(1H-1,2,3-triazol-4-yl))amino)tetrafluorophenyl]porphyrinato}-zinc(II)-hPG-azide

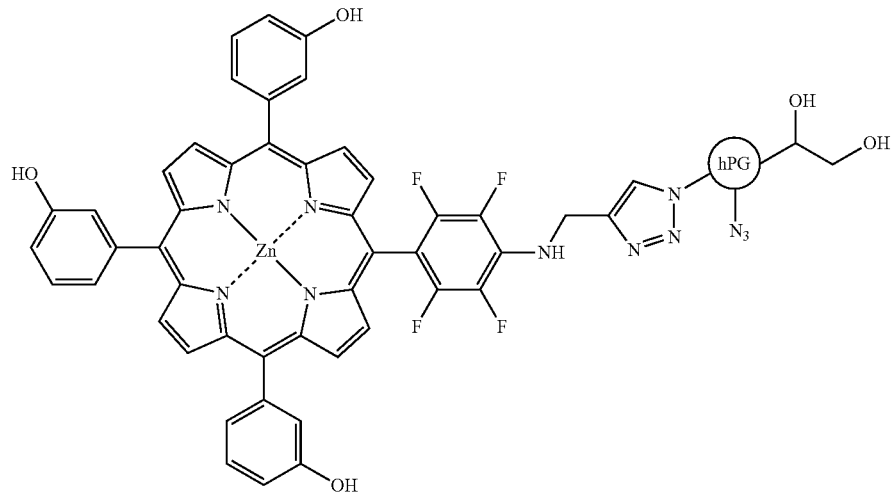

In a 5 ml flask with magnetic stirrer hPG-azide was dissolved in 1 ml of DMSO (Acros). {5,10,15-Tris (3-hydroxyphenyl)-20-[4-(prop-2-yn-1-ylamino))tetrafluorophenyl]porphyrinato}-zinc(II), L-ascorbic acid sodium salt in $H_2O$ and copper(II) sulfate hydrate in $H_2O$ were added and the solution was stirred at RT for 3 d. Afterwards the reaction mixture was heated to 60° C. for 3 h. The crude product was purified by dialysis for 3 d to obtain the purple product {5,10,15-tris(3-hydroxyphenyl)-20-[4-(N-(1H-1,2,3-triazol-4-yl))-amino)tetrafluorophenyl]porphyrinato}-zinc(II)-hPG-azide.

1.21 General synthesis of {5,10,15-tris(3-hydroxyphenyl)-20-[4-(N-(1H-1,2,3-triazol-4-yl))amino)tetrafluorophenyl]porphyrinato}-zinc(II)-hPG-mannose

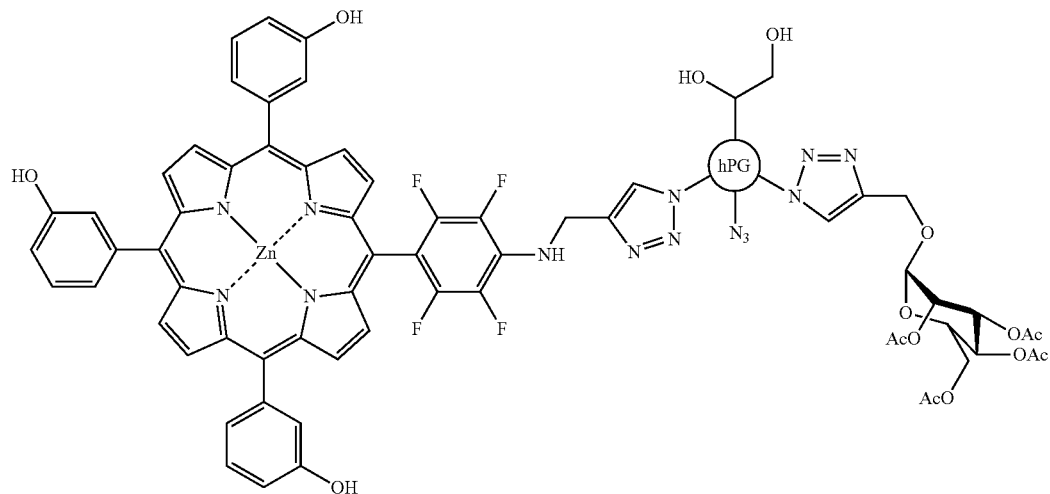

In a 5 ml flask with magnetic stirrer {5,10,15-tris(3-hydroxyphenyl)-20[4-(N-(1H-1,2,3-triazol-4-yl))amino)tetrafluorophenyl]porphyrinato}-zinc(II)-hPG-azide was dissolved in 1 ml of DMSO (Acros). Propargylated-mannose protected, L-ascorbic acid sodium salt in H₂O and copper(II) sulfate hydrate in H₂O were added and the solution was stirred at RT for 3 d. Afterwards the reaction mixture was heated to 60° C. for 3 h. The crude product was purified by dialysis for 3 d to obtain the purple product {5,10,15-tris(3-hydroxyphenyl)-20-[4-(N-(1H-1,2,3-triazol-4-yl))amino)tetrafluorophenyl]porphyrinato}-zinc(II)-hPG-mannose protected.

1.22 General Synthesis of {5,10,15-tris(3-hydroxyphenyl)-20-[4-(N-(1H-1,2,3-triazol-4-yl))amino)tetrafluorophenyl]porphyrinato}-zinc(II)-hPG-mannose

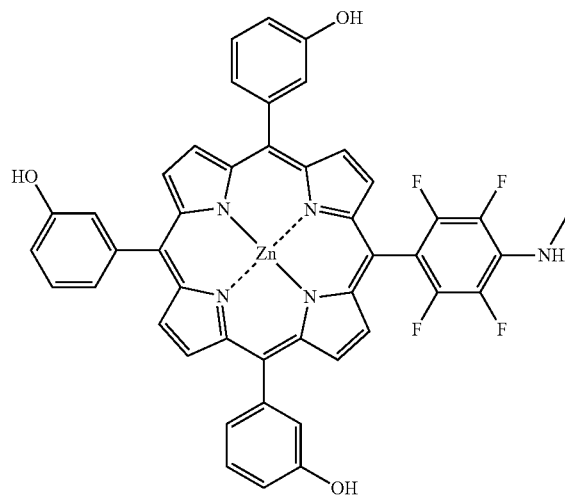
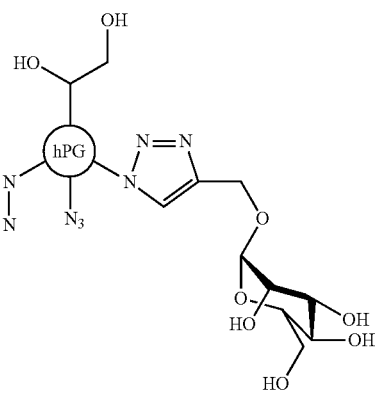

In a 25 ml two-necked flask with magnetic stirrer {5,10,15-tris(3-hydroxyphenyl)-20-[4-(N-(1H1,2,3-triazol-4-yl))amino)tetrafluorophenyl]porphyrinato}-zinc(II)-hPG-mannose protected was dissolved in 2 ml of anhydrous DMF and 3 ml of dry MeOH under argon. NaOMe in MeOH was added and the solution was stirred at RT for 16 d. H₂O was added and the solution was stirred for 4 h. The crude product was purified by dialysis for 3 d to obtain the purple product {5,10,15-tris(3-hydroxyphenyl)-20-[4-(N-(1H-1,2,3-triazol-4-yl))amino)tetrafluorophenyl]porphyrinato}-zinc(II)-hPG-mannose.

1.23 {5,10,15-Tris(3-hydroxyphenyl)-20-[4-(N-(1H-1,2,3-triazol-4-yl))amino)tetrafluorophenyl]porphyrinato}-zinc(II)-hPG$_{3.7}$-azide with 6.4% Porphyrins and 58.6% Azides (MS149)

According to the general synthesis procedure: hPG$_{3.7}$-azide with 65% azides (29.1 mg, 6.47 µmol, 210 µmol azide groups), {5,10,15-tris(3-hydroxyphenyl)-20-[4-(prop-2-yn-1-ylamino))tetrafluorophenyl]porphyrinato}-zinc(II) (18.3 mg, 21.5 µmol), L-ascorbic acid sodium salt (8.60 µl, 0.5 M in H₂O, 4.30 µmol) and copper(II) sulfate hydrate (5.38 µl, 0.4 M in H₂O, 2.15 mol), were used. The crude product was purified by dialysis (acetone/H₂O (9:1)) to obtain the product {5,10,15-tris(3-hydroxyphenyl)-20-[4-(N-(1H-1,2,3-triazol-4-yl))amino)tetrafluorophenyl]porphyrinato}-zinc(II)-hPG$_{3.7}$-azide with 6.4% porphyrins and 58.6% azides (37.7 mg, 5.24 µmol, 16.8 µmol porphyrin and 153 µmol azide groups, 81% yield, 96% conversion).

{5,10,15-Tris(3-hydroxyphenyl)-20-[4-(N-(1H-1,2,3-triazol-4-yl))amino)tetrafluorophenyl]porphyrinato}-zinc(II)-hPG$_{3.7}$-azide with 6.4% Porphyrins and 58.6% Azides $^1$H NMR ([D6]Acetone/D₂O 9:1, 700 MHz): δ=9.09-8.66 (bs, β), 7.81-7.00 (m, Ar+triazole-H), 4.21-2.58 (m, hPG-backbone+porphyrin-CH₂).

1.24 {5,10,15-Tris(3-hydroxyphenyl)-20-[4-(N-(1H-1,2,3-triazol-4-yl))amino)tetra-fluorophenyl]porphyrinato}-zinc(II)-hPG$_{9.8}$-azide with 10.0% Porphyrins and 55.0% Azides (M5147)

According to the general synthesis procedure: hPG$_{9.8}$-azide with 65% azides (23.5 mg, 1.96 µmol, 169 µmol azide groups), {5,10,15-tris(3-hydroxyphenyl)-20-[4-(prop-2-yn-1-ylamino))tetrafluorophenyl]porphyrinato}-zinc(II) (25.3 mg, 29.7 µmol), L-ascorbic acid sodium salt (11.8 µl, 0.5 M in H₂O, 5.96 µmol) and copper(II) sulfate hydrate (7.42 µl, 0.4 M in H₂O, 2.97 mol), were used. The crude product was purified by dialysis (acetone/H₂O (9:1)) to obtain the product {5,10,15-tris(3-hydroxyphenyl)-20-[4-(N-(1H-1,2,3-triazol-4-yl))amino)tetrafluorophenyl]porphyrinato}-zinc(II)-hPG$_{9.8}$-azide with 10.0% porphyrins and 55.0% azides (32.9 mg, 1.41 µmol, 18.7 µmol porphyrin and 103 µmol azide groups, 72% yield, 87% conversion).

{5,10,15-Tris(3-hydroxyphenyl)-20-[4-(N-(1H-1,2,3-triazol-4-yl))amino)tetrafluorophenyl]porphyrinato}-zinc(II)-hPG$_{9.8}$-azide with 10.0% Porphyrins and 55.0% Azides $^1$H NMR ([D6]Acetone/D₂O 9:1, 700 MHz): δ=9.04-8.57 (bs, β), 7.77-6.91 (m, Ar+triazole-H), 4.04-2.48 (m, hPG-backbone+porphyrin-CH₂).

1.25 {5,10,15-Tris(3-hydroxyphenyl)-20-[4-(N-(1H-1,2,3-triazol-4-yl))amino)tetra-fluorophenyl]porphyrinato}-zinc(II)-hPG$_{19.5}$-azide with 7.2% Porphyrins and 58.8% Azides (MS117)

According to the general synthesis procedure: hPG$_{19.5}$-azide with 66% azides (23.9 mg, 1.00 µmol, 174 µmol azide groups), {5,10,15-tris(3-hydroxyphenyl)-20-[4-(prop-2-yn-1-ylamino))tetrafluorophenyl]porphyrinato}-zinc(II) (16.3 mg, 19.2 µmol), L-ascorbic acid sodium salt (75.9 µl, 50 mM in H$_2$O, 3.80 µmol) and copper(II) sulfate hydrate (4.78 µl, 0.4 M in H$_2$O, 1.91 µmol), were used. The crude product was purified by dialysis (acetone/H$_2$O (9:1)) to obtain the product {5,10,15-tris(3-hydroxyphenyl)-20-[4-(N-(1H-1,2,3-triazol-4-yl))amino)tetrafluorophenyl]porphyrinato}-zinc(II)-hPG$_{19.5}$-azide with 7.2% porphyrins and 58.8% azides (30.9 mg, 773 nmol, 14.7 µmol porphyrin and 120 µmol azide groups, 77% yield, quant. conversion).

{5,10,15-Tris(3-hydroxyphenyl)-20-[4-(N-(1H-1,2,3-triazol-4-yl))amino)tetrafluoro-phenyl]porphyrinato}-zinc(II)-hPG$_{19.5}$-azide with 7.2% Porphyrins and 58.8% Azides $^1$H NMR ([D6]Acetone, 700 MHz): δ=9.18-8.62 (bs, β+OH), 7.93-7.08 (m, Ar+triazole-H), 4.51-2.57 (m, hPG-backbone+porphyrin-CH$_2$).

1.26 {5,10,15-Tris(3-hydroxyphenyl)-20-[4-(N-(1H-1,2,3-triazol-4-yl))amino)tetra-fluorophenyl]porphyrinato}-zinc(II)-hPG$_{3.7}$-mannose Protected with 6.4% Porphyrins, 28.0% Mannose Protected and 30.6% Azides (MS157)

According to the general synthesis procedure: {5,10,15-Tris(3-hydroxyphenyl)-20-[4-(N-(1H-1,2,3-triazol-4-yl))amino)tetrafluorophenyl]porphyrinato}-zinc(II)-hP G$_{3.7}$-azide with 6.4% porphyrins and 58.6% azides (37.7 mg, 5.24 µmol, 16.8 µmol porphyrin and 153 µmol, azide groups), propargylated-mannose protected (37.8 mg, 97.8 µmol), L-ascorbic acid sodium salt (38.8 µl, 0.5 M in H$_2$O, 19.6 µmol) and copper(II) sulfate hydrate (24.4 µl, 0.4 M in H$_2$O, 9.77 mol), were used. The crude product was purified by dialysis (acetone/H$_2$O (9:1)) to obtain the product {5,10,15-tris(3-hydroxyphenyl)-20-[4-(N-(1H-1,2,3-triazol-4-yl))amino)tetrafluorophenyl]porphyrinato}-zinc(II)-hPG$_{3.7}$-mannose protected with 6.4% porphyrins, 28.0% mannose protected and 30.6% azides (59.5 mg, 4.72 15.1 µmol porphyrin, 66.1 µmol mannose protected and 72.2 µmol azide groups, 90% yield, 75% conversion).

{5,10,15-Tris (3-hydroxyphenyl)-20-[4-(N-(1H-1,2,3-triazol-4-yl))amino)tetrafluoro-phenyl]porphyrinato}-zinc(II)-hPG$_{3.7}$-mannose Protected with 6.4% Porphyrins, 28.0% Mannose Protected and 30.6% Azides $^1$H NMR ([D6]Acetone, 700 MHz): δ=9.37-8.71 (bs, β+OH), 8.25-7.02 (m, Ar+porphyrin/Man-triazole-H), 5.51-5.07 (m, Man: H-1, H-2, H-3, H-4), 5.07-2.72 (m, hPG-backbone+porphyrin-CH$_2$+Man), 2.29-1.69 (m, OAc). $^{13}$C NMR ([D6]Acetone, 176 MHz): δ=170.96, 170.55, 170.24, 156.46, 151.14, 150.84, 150.65, 148.31, 146.97, 145.27, 143.99, 138.91, 137.51, 133.67, 132.64, 131.13, 128.31, 127.37, 125.74, 125.08, 122.99, 121.83, 115.45, 110.43, 103.53, 97.26, 79.44, 73.77, 71.64, 70.04, 69.56, 66.66, 63.07, 61.62, 60.85, 54.39, 53.77, 52.20, 51.33, 20.80.

1.27 {5,10,15-Tris(3-hydroxyphenyl)-20-[4-(N-(1H-1,2,3-triazol-4-yl))amino)tetra-fluorophenyl]porphyrinato}-zinc(II)-hPG$_{9.8}$-mannose Protected with 10.0% Porphyrins, 28.7% Mannose Protected and 26.3% Azides (MS156)

According to the general synthesis procedure: {5,10,15-Tris(3-hydroxyphenyl)-20-[4-(N-(1H-1,2,3-triazol-4-yl))amino)tetrafluorophenyl]porphyrinato}-zinc(II)-hPG$_{9.8}$-azide with 10.0% porphyrins and 55.0% azides (32.9 mg, 1.41 µmol, 18.7 µmol porphyrin and 103 azide groups), propargylated-mannose protected (34.5 mg, 89.3 µmol), L-ascorbic acid sodium salt (35.4 µl, 0.5 M in H$_2$O, 17.7 µmol) and copper(II) sulfate hydrate (22.3 µl, 0.4 M in H$_2$O, 8.93 mol), were used. The crude product was purified by dialysis (acetone/H$_2$O (9:1)) to obtain the product {5,10,15-tris(3-hydroxyphenyl)-20-[4-(N-(1H-1,2,3-triazol-4-yl))amino)tetrafluorophenyl]porphyrinato}-zinc(II)-hPG$_{9.8}$-mannose protected with 10.0% porphyrins, 28.7% mannose protected and 26.3% azides (48.5 mg, 1.28 µmol, 16.9 µmol porphyrin, 48.5 µmol mannose protected and 44.5 µmol azide groups, 91% yield, 60% conversion).

{5,10,15-Tris(3-hydroxyphenyl)-20-[4-(N-(1H-1,2,3-triazol-4-yl))amino)tetrafluoro-phenyl]porphyrinato}-zinc(II)-hPG$_{9.8}$-mannose Protected with 10.0% Porphyrins, 28.7% Mannose Protected and 26.3% Azides $^1$H NMR ([D6]Acetone, 700 MHz): δ=9.18-8.58 (bs, β+OH), 8.23-6.98 (m, Ar+porphyrin/Man-triazole-H), 5.50-5.07 (m, Man: H-1, H-2, H-3, H-4), 5.07-3.03 (m, hPG-backbone+porphyrin-CH$_2$+Man), 2.27-1.62 (m, OAc). $^{13}$C NMR ([D6]Acetone, 176 MHz): δ=170.97, 170.56, 170.25, 156.46, 151.14, 150.85, 150.63, 148.24, 146.96, 145.29, 144.02, 138.83, 137.48, 133.65, 132.56, 131.14, 128.22, 127.40, 126.06, 125.75, 125.05, 123.03, 121.80, 115.40, 110.54, 103.51, 97.52, 97.27, 79.42, 73.72, 72.28, 70.94, 70.06, 69.57, 66.66, 63.08, 60.83, 53.74, 51.32, 20.81.

1.28 {5,10,15-Tris(3-hydroxyphenyl)-20-[4-(N-(1H-1,2,3-triazol-4-yl))amino)tetra-fluorophenyl]porphyrinato}-zinc(II)-hPG$_{19.5}$-mannose Protected with 7.2% Porphyrins, 34.1% Mannose Protected and 24.7% Azides (MS124)

According to the general synthesis procedure: {5,10,15-Tris(3-hydroxyphenyl)-20-[4-(N-(1H-1,2,3-triazol-4-yl))amino)tetrafluorophenyl]porphyrinato}-zinc(II)-hPG$_{19.5}$-azide with 7.2% porphyrins and 58.8% azides (10.2 mg, 255 nmol, 4.84 µmol porphyrin and 39.5 µmol azide groups), propargylated-mannose protected (19.4 mg, 50.2 µmol), ascorbic acid sodium salt (19.9 µl, 0.5 M in H$_2$O, 9.94 µmol) and copper(II) sulfate hydrate (12.5 µl, 0.4 M in H$_2$O, 5.01 µmol), were used. The crude product was purified by dialysis (acetone/H$_2$O (8:1)) to obtain the product {5,10,15-tris(3-hydroxyphenyl)-20-[4-(N-(1H-1,2,3-triazol-4-yl))amino)tetrafluorophenyl]porphyrinato}-zinc(II)-hPG$_{19.5}$-mannose protected with 7.2% porphyrins, 34.1% mannose protected and 24.7% azides (17.1 mg, 230 nmol, 4.36 µmol porphyrin, 20.7 µmol mannose protected and 15.0 µmol azide groups, 90% yield, 58% conversion).

{5,10,15-Tris(3-hydroxyphenyl)-20-[4-(N-(1H-1,2, 3-triazol-4-yl))amino)tetrafluorophenyl]porphyrinato}-zinc(II)-hPG$_{19.5}$-mannose Protected with 7.2% Porphyrins, 34.1% Mannose Protected and 24.7% Azides $^1$H NMR (CDCl$_3$, 700 MHz): δ=9.46-8.65 (bs, β+OH), 8.14-7.16 (m, Ar+porphyrin/Man-triazole-H), 5.47-5.04 (m, Man: H-1, H-2, H-3, H-4), 5.04-2.79 (m, hPG-backbone+porphyrin-CH$_2$+Man), 2.35-1.46 (m, OAc). $^{13}$C NMR (CDCl$_3$, 176 MHz): δ=170.80, 170.14, 169.80, 143.45, 124.87, 96.79, 69.43, 68.78, 66.01, 62.42, 60.46, 20.97, 20.90, 20.82.

1.29 {5,10,15-Tris(3-hydroxyphenyl)-20-[4-(N-(1H-1,2,3-triazol-4-yl))amino)tetra-fluorophenyl]porphyrinato}-zinc(II)-hPG$_{3.7}$-mannose with 6.4% Porphyrins, 28.0% Mannose and 30.6% Azides (MS168/BLC 4174)

According to the general synthesis procedure: {5,10,15-Tris(3-hydroxyphenyl)-20-[4-(N-(1H-1,2,3-triazol-4-yl))amino)tetrafluorophenyl]porphyrinato}-zinc(II)-hPG$_{3.7}$-mannose with 6.4% porphyrins, 28.0% mannose protected and 30.6% azides (59.5 mg, 4.72 µmol, 15.1 µmol porphyrin, 66.1 µmol mannose protected and 72.2 µmol azide groups) and NaOMe (1.00 ml, 80 mM in MeOH, 80.0 µmol) were used. The crude product was purified by dialysis (H$_2$O) to obtain the product {5,10,15-tris(3-hydroxyphenyl)-20-[4-(N-(1H-1,2,3-triazol-4-yl))amino)tetrafluorophenyl]porphyrinato}-zinc(II)-hPG$_{3.7}$-mannose with 6.4% porphyrins, 28.0% mannose and 30.6% azides (47.0 mg, 4.56 µmol, 14.6 µmol porphyrin, 63.8 µmol mannose and 69.8 µmol azide groups, 97% yield, quant. conversion).

{5,10,15-Tris(3-hydroxyphenyl)-20-[4-(N-(1H-1,2, 3-triazol-4-yl))amino)tetrafluoro-phenyl]porphyrinato}-zinc(II)-hPG$_{3.7}$-mannose with 6.4% Porphyrins, 28.0% Mannose and 30.6% Azides $^1$H NMR (D$_2$O, 700 MHz): δ=9.46-8.75 (bs, (3), 8.35-7.19 (m, Ar+porphyrin/Man-triazole-H), 4.34-2.86 (m, hPG-backbone+porphyrin-CH$_2$+Man). $^{13}$C NMR (D$_2$O, 176 MHz): δ=143.68, 125.96, 125.51, 124.68, 99.35, 99.03, 78.09, 72.94, 72.20, 70.50, 69.95, 66.68, 60.88, 59.55, 59.24, 52.79, 50.55, 38.71.

1.30 {5,10,15-Tris(3-hydroxyphenyl)-20-[4-(N-(1H-1,2,3-triazol-4-yl))amino)tetra-fluorophenyl]porphyrinato}-zinc(II)-hPG$_{9.8}$-mannose with 10.0% Porphyrins, 28.7% Mannose and 26.3% Azides (MS167/BLC 4177)

According to the general synthesis procedure: {5,10,15-Tris(3-hydroxyphenyl)-20-[4-(N-(1H-1,2,3-triazol-4-yl))amino)tetrafluorophenyl]porphyrinato}-zinc(II)-hPG$_{9.8}$-mannose with 10.0% porphyrins, 28.7% mannose protected and 26.3% azides (48.5 mg, 1.28 µmol, 16.9 µmol porphyrin, 48.5 µmol mannose protected and 44.5 µmol azide groups) and NaOMe (1.00 ml, 65 mM in MeOH, 65.0 µmol) were used. The crude product was purified by dialysis (H$_2$O) to obtain the product {5,10,15-tris(3-hydroxyphenyl)-20-[4-(N-(1H-1,2,3-triazol-4-yl))amino)tetrafluorophenyl]porphyrinato}-zinc(II)-hPG$_{9.8}$-mannose with 10.0% porphyrins, 28.7% mannose and 26.3% azides (33.2 mg, 1.05 µmol, 13.9 µmol porphyrin, 39.9 µmol mannose and 36.6 µmol azide groups, 82% yield, quant. conversion).

{5,10,15-Tris (3-hydroxyphenyl)-20-[4-(N-(1H-1,2, 3-triazol-4-yl))amino)tetrafluoro-phenyl]porphyrinato}-zinc(II)-hPG$_{9.8}$-mannose with 10.0% Porphyrins, 28.7% Mannose and 26.3% Azides $^1$H NMR (D$_2$O, 700 MHz): δ=9.45-8.59 (bs, (3), 8.38-7.04 (m, Ar+porphyrin/Man-triazole-H), 4.23-3.13 (m, hPG-backbone+porphyrin-CH$_2$+Man). $^{13}$C NMR (D$_2$O, 176 MHz): δ=143.62, 126.03, 125.58, 124.43, 99.36, 99.03, 77.78, 72.94, 72.13, 70.49, 69.94, 68.85, 66.69, 60.88, 59.61, 59.27, 52.80, 50.65.

1.31 {5,10,15-Tris(3-hydroxyphenyl)-20-[4-(N-(1H-1,2,3-triazol-4-yl))amino)tetra-fluorophenyl]porphyrinato}-zinc(II)-hPG$_{19.5}$-mannose with 7.2% Porphyrins, 34.1% Mannose and 24.7% Azides (MS135/BLC 3175)

According to the general synthesis procedure: {5,10,15-Tris(3-hydroxyphenyl)-20-[4-(N-(1H-1,2,3-triazol-4-yl))amino)tetrafluorophenyl]porphyrinato}-zinc(II)-hPG$_{19.5}$-mannose protected with 7.2% porphyrins, 34.1% mannose protected and 24.7% azides (17.1 mg, 230 nmol, 4.36 µmol porphyrin, 20.7 µmol mannose protected and 15.0 µmol azide groups) and NaOMe (480 µl, 104 mM in MeOH, 50.0 µmol) were used. The crude product was purified by dialysis (H$_2$O) to obtain the product {5,10,15-tris(3-hydroxyphenyl)-20-[4-(N-(1H-1,2,3-triazol-4-yl))amino)tetrafluorophenyl]porphyrinato}-zinc(II)-hPG$_{19.5}$-mannose with 7.2% porphyrins, 34.1% mannose and 24.7% azides (12.5 mg, 210 nmol, 3.98 µmol porphyrin, 18.9 µmol mannose and 13.7 µmol azide groups, 91% yield, quant. conversion).

{5,10,15-Tris(3-hydroxyphenyl)-20-[4-(N-(1H-1,2, 3-triazol-4-yl))amino)tetrafluoro-phenyl]porphyrinato}-zinc(II)-hPG$_{19.5}$-mannose with 7.2% Porphyrins, 34.1% Mannose and 24.7% Azides $^1$H NMR ([D6]DMSO, 700 MHz): δ=8.97-8.51 (bs, β+OH), 8.14-7.03 (m, Ar+porphyrin/Man-triazole-H), 5.38-2.85 (m, hPG-backbone+porphyrin-CH$_2$+Man).

1.32 5,10,15-Tris(3-hydroxyphenyl)-20-[4-((6-(((((1R,8S,9s)-bicyclo[6.1.0]non-4-yn-9-yl)methoxy)carbonyl)amino)hexyl)amino)tetrafluorophenyl]porphyrin-hPG$_{19.5}$-mannose-azide with 7.2% Porphyrin, 38.0% Mannose and 34.8% Azide Groups (MS152/BLC 4163)

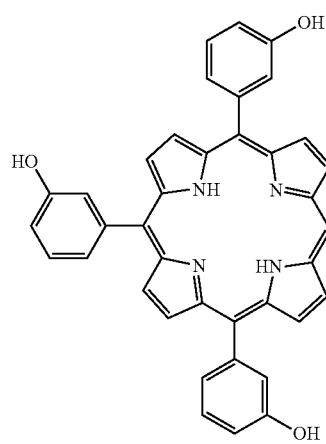
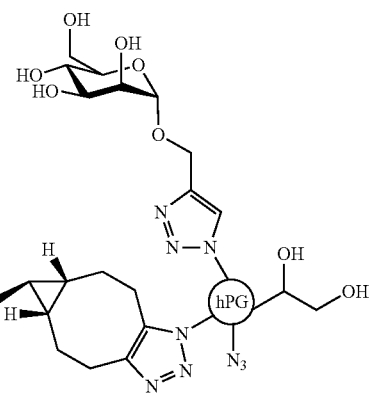

In a 5 ml flask with magnetic stirrer hPG$_{19.5}$-mannose-azide with 38% mannose and 42% azide groups (21.4 mg, 459 nmol, 45.9 µmol mannose and 50.8 µmol azide groups) was dissolved in 1 ml of dry DMSO (Acros). 5,10,15-Tris(3-hydroxyphenyl)-20-[4-((6-(((((1R,8S,9s)-bicyclo [6.1.0]non-4-yn-9-yl)methoxy)carbonyl)amino)hexyl)amino)tetrafluorophenyl]porphyrin (14.0 mg, 13.7 µmol) was added and the solution was stirred at RT for 1 d. The crude product was purified by dialysis in acetone for 3 d to obtain the purple product 5,10,15-tris(3-hydroxyphenyl)-20-[4-((6-(((((1R,8S,9s)-bicyclo [6.1.0]non-4-yn-9-yl)methoxy)carbonyl)amino)hexyl)amino)tetrafluorophenyl]porphyrin-hPG$_{19.5}$-mannose-azide with 7.2% porphyrin, 38.0% mannose and 34.8% azide groups (30.3 mg, 459 nmol, 8.71 µmol porphyrin, 45.9 µmol mannose and 42.1 µmol azide groups, quant. yield, 64% conversion).

5,10,15-Tris(3-hydroxyphenyl)-20-[4-((6-(((((1R,8S,9s)-bicyclo[6.1.0]non-4-yn-9-yl)-methoxy)carbonyl)amino)hexyl)amino)tetrafluorophenyl]porphyrin-hPG$_{19.5}$-mannose-azide with 7.2% Porphyrin, 38.0% Mannose and 34.8% Azide Groups $^1$H NMR ([D8]THF/D$_2$O (85:15), 700 MHz): δ (ppm)= 9.14-8.61 (bs, β), 8.26-7.06 (m, Ar+porphyrin/Man-triazole-H), 5.74-2.75 (m, Man: H-1, H-2, H-3, H-4, H-5, H-6, —OCH$_2$; hPG backbone; porphyrin-CH$_2$+cyclooctyne-CH$_2$), 1.93-1.00 (porphyrin-CH$_2$+cyclooctyne-CH$_2$). $^{13}$C NMR ([D8]THF/D$_2$O (85:15), 176 MHz): δ (ppm)=157.31, 148.72, 147.35, 145.03, 144.00, 143.89, 138.50, 137.19, 130.68, 128.47, 126.88, 123.02, 122.46, 121.54, 116.01, 107.31, 103.68, 100.58, 100.29, 79.61, 74.41, 72.03, 71.39, 62.28, 60.42, 51.54, 46.27, 41.52, 31.86, 30.90, 27.46.

Example 2: Quenching and Release Experiments of the Porphyrinoid-Polymer-Conjugates 2.1 Quenching Experiment Compound 1.16 ({5,10,15-Tris(3-hydroxyphenyl)-20-[2,3,5,6-tetrafluoro-4-N-((2(2-(1H-1,2,3-triazol-4-yl-carboxamido)ethyl)-disulfanyl)ethyl)aminophenyl)]porphyrinato}-zinc(II)-hPG19.5-azide with 0.6% porphyrin zinc(II) complex and 1.4% azide groups) (point of a spatula) was dissolved in methanol/H$_2$O (2 ml) in presence of DTT (50 mmolL$^{-1}$). The solution was heated to 37° C. Fluorescence spectra were measured after 0, 204, 408, 816, 1020, 1224, 1428, 1632, 1837, 2041, 2245, 2449, 2653, 2857, 3061, 3265 and 3469 s.

2.2 Release Study Followed by TLC

Compound 1.16 (point of a spatula) was dissolved in methanol (200 ml). DTT (1 mg) was added and the solution was heated to 50° C. for 1 min. A TLC in methanol was performed.

2.3 Release Study Followed by SEC

Compound 1.16 (point of a spatula) was dissolved in H$_2$O (200 ml). DTT (1 mg) was added and the solution was kept for 10 min at RT. A SEC in H$_2$O was performed.

2.4 Release Study Followed by Dialysis

Compound 1.16 (5 mg) was dissolved in methanol/H$_2$O (5 ml, 1:1). After the sample was been degassed with argon, it was filled into a dialysis tube. The sample was dialyzed in a beaker with DTT (50 mmolL$^{-1}$) in methanol/H$_2$O (245 ml, 1:1) for 6060 min. Compound 1.16 (5 mg) was dissolved in methanol/H$_2$O (5 ml, 1:1) and filled into a dialysis tube. The sample was dialyzed in a beaker with methanol/H$_2$O (250 ml, 1:1) for 6060 min. During the dialysis outside the tube fluorescence spectra were measured after 0, 140, 240, 1270, 1580, 3175 and 6060 min.

Example 3: Phototoxicity Testing 3.1 Phototoxicity Testing in Selected Cell Lines The photosensitzing activity was determined in the following cell lines:

HT29 (human colon adenocarcinoma cell line)
L929 (mouse fibroblast cell line)
A431 (human epidermoid carcinoma cell line)
A253 (submaxillary salivary gland, epidermoid cell line)
CAL-27 (human tongue squamous cell carcinoma cell line).

The cell lines were grown in DMEM (PAA Laboratories GmbH) supplemented with 10% heat-inactivated fetal calf serum (FCS, PAA Laboratories GmbH), 1% penicillin (10000 IU) and streptomycin (10000 µg/ml, PAA Laboratories GmbH). Cells were kept as a monolayer culture in a humidified incubator (5% $CO_2$ in air at 37° C.).

A photosensitizer stock solution was prepared in DMSO and was kept in the dark at 4° C. Further dilution was performed in DMEM medium without phenol red supplemented with 10% FCS to reach a final photosensitizer concentration of 2 or 10 µM, respectively.

$2 \cdot 10^4$ cells/ml were seeded in micro plates ($2 \cdot 10^5$ cells/well). Cells were incubated with fresh medium (DMEM without phenol red) containing 10% FCS with 2 or 10 µM of the photosensitizer for 24 h before light exposure. Before photosensitization, cells were washed, cell culture medium was exchanged with DMEM without phenol red and 10% FCS, then irridiated at room temperature with a 652 nm diode laser (Ceralas PDT 652, biolitec AG) or with a white light source at a fixed fluence rate of 100 mW/cm² (50 J/cm²). Following irradiation, cells were incubated in a humidified incubator (5% $CO_2$ in air at 37° C.) for 24 h until cell viability assay. The cell viability was assessed by the XTT assay. 500 mg XTT (sodium 3'-[phenylaminocarbonyl)-3,4-tetrazolium]-bis(4-methoxy-6-nitro)benzene sulfonic acid, Applichem GmbH) is dissolved in 500 ml PBS-Buffer (without $Ca^{2+}$ and $Mg^2$) and sterile filtered. Solution was stored in the dark at −20° C. until use. A sterile solution containing PMS (N-methyl dibenzopyrazine methyl sulfate, Applichem GmbH) was needed as an activation reagent for the XTT. 0.383 mg PMS was dissolved in 1 ml PBS-Buffer. The XTT reagent solution was thawed in a 37° C. water bath and the activation solution (PMS) was added immediately prior to use. To prepare a reaction solution sufficient for one micro plate (96 wells), 0.1 ml activation solution (PMS) was given to 5 ml XTT reagent. The medium in the micro plate was exchanged with RPMI without phenol red and 10% FCS (100 µl) prior adding 50 µl XTT reaction solution per well. The micro plate was incubated for 2-3 hours at 37° C. and 5% $CO_2$ until an orange dye is to be formed. The micro plate has been shaken gently to evenly distribute the dye in the wells.

The absorbance of the samples was measured with a spectrophotometer (Infinite 200, Tecan Group Ltd.) at a wavelength of 490 nm. In order to measure reference absorbance (to measure non-specific readings) a wavelength of 630-690 nm was used. The examples illustrate the photodynamic activity ("DT" means dark toxicity and "Laser" means photo toxicity).

3.1.1 Cell Toxicity testing of porphyrinoid-polymer-conjugate 5,10,15-Tris(3-hydroxyphenyl)-20-[4-((2 (2-(((((1R,8S,9s)-bicyclo[6.1.0]non-4-yn-9-yl) methoxy)-carbonyl)₋ amino)ethyl) disulfanyl)₋ ethyl)amino)₋ tetrafluorophenyl]-porphyrin-hPG19.5-mannose-azide with 6.3% Porphyrin, 38% Mannose and 35.7% Azide Groups (See Example 1.15)

Figure 7:
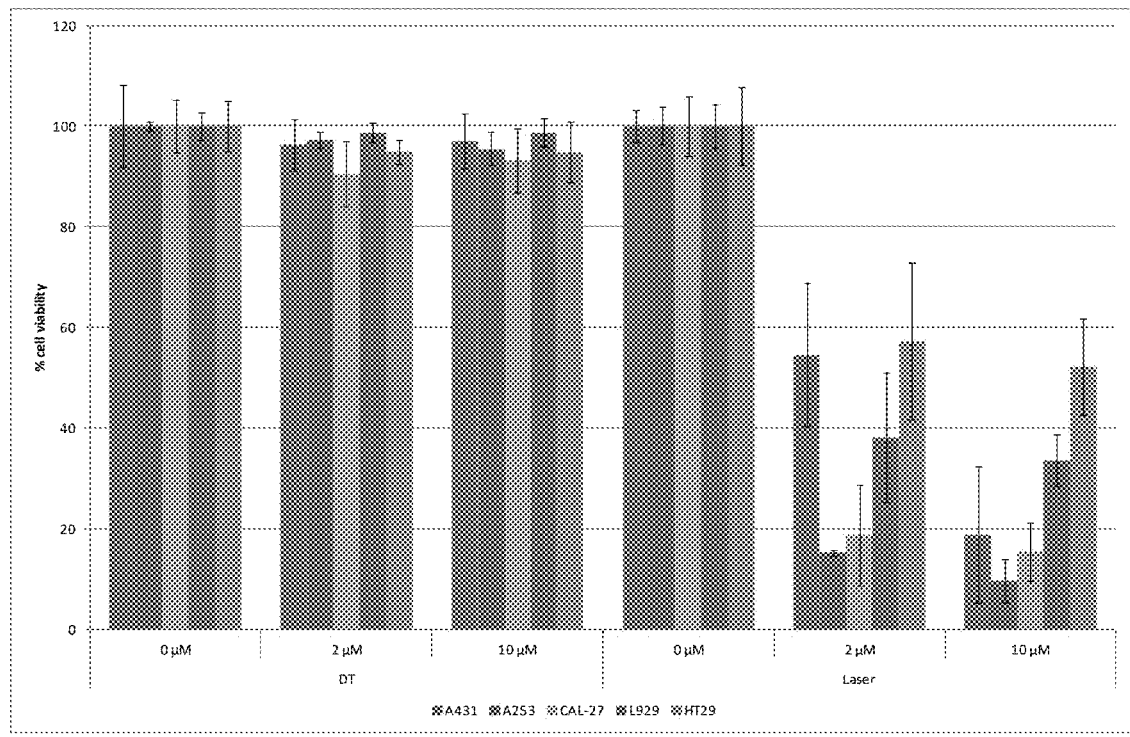
FIG. 7 shows the cell toxicity test of one embodiment of present disclosure (conjugate MS153/BLC 4161) after 24 h incubation time and irradiation with a 652 nm laser at 50 J/cm$^2$.

FIG. 7 shows the cell toxicity test of conjugate MS153/BLC 4161 after 24 h incubation and irradiation with a 652 nm laser at 50 J/cm².

3.1.2 Cell Toxicity Testing of porphyrinoid-polymer-conjugate (2-(2-Methoxy-4-(3-((5a8,6R,6aR)-6-(((((6-((2,3,5,6-tetrafluoro-4-(10,15,20-tris(3-hydroxyphenyl)porphyrin-5-yl)phenyl)amino)hexyl) carbamoyl)oxy)methyl)-5,5a,6,6a,7,8-hexahydrocyclopropa[5,6]cycloocta[1,2-d][1,2,3] triazol-1(4H)-yl)propoxy)phenyl)-1,3-dioxolan-4-yl)-hPG9.1 with 6 Porphyrin Groups (See Example 1.11)

Figure 8:
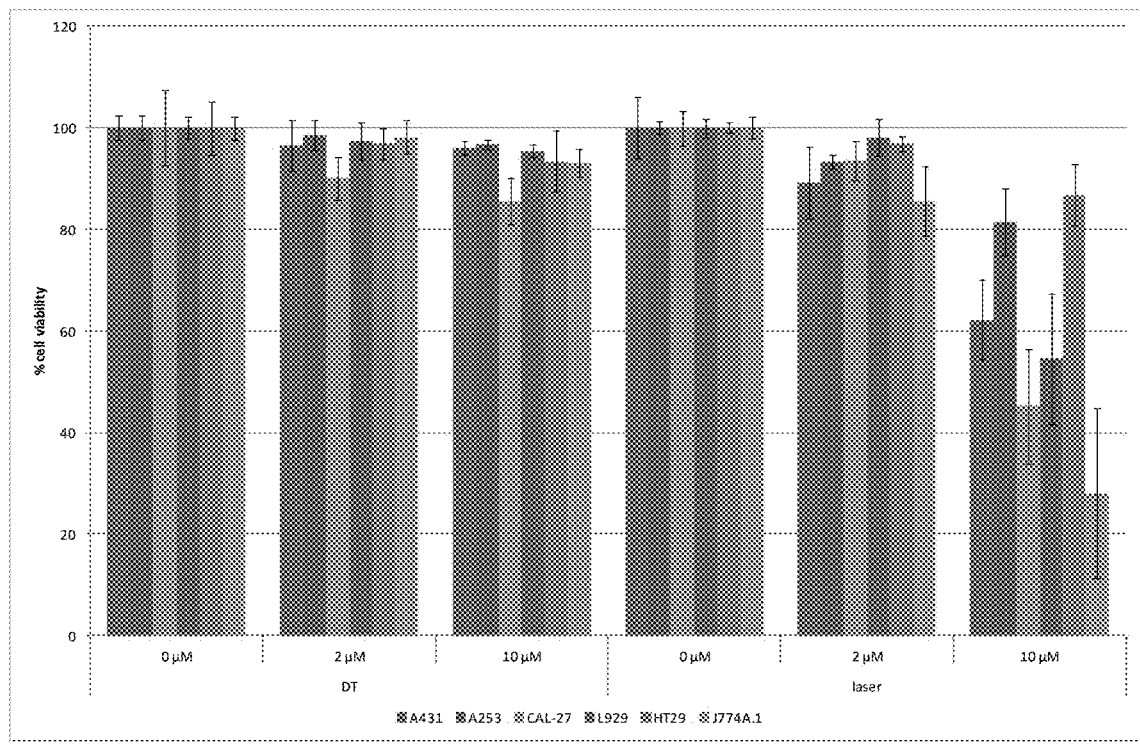
FIG. 8 shows the cell toxicity test of one embodiment of present disclosure (conjugate MS154/BLC 4176) after 24 h incubation and irradiation with a 652 nm laser at 50 J/cm$^2$.

FIG. 8 shows the cell toxicity test of conjugate MS154/BLC 4176 after 24 h incubation and irradiation with a 652 nm laser at 50 J/cm².

3.1.3 Cell Toxicity Testing of porphyrinoid-polymer-conjugate 5,10,15-Tris(3-hydroxyphenyl)-20-[4-((2-((2-(((((1R,8S,9r)-bicyclo[6.1.0]non-4-yn-9-yl)methoxy)carbonyl)amino)₋ ethyl)disulfanyl) ethyl)₋ amino)tetrafluoro-phenyl]porphyrin-hPG19.5-azide with 3.2% Porphyrin and 9.8% Azide Groups (See Example 1.14)

Figure 9:
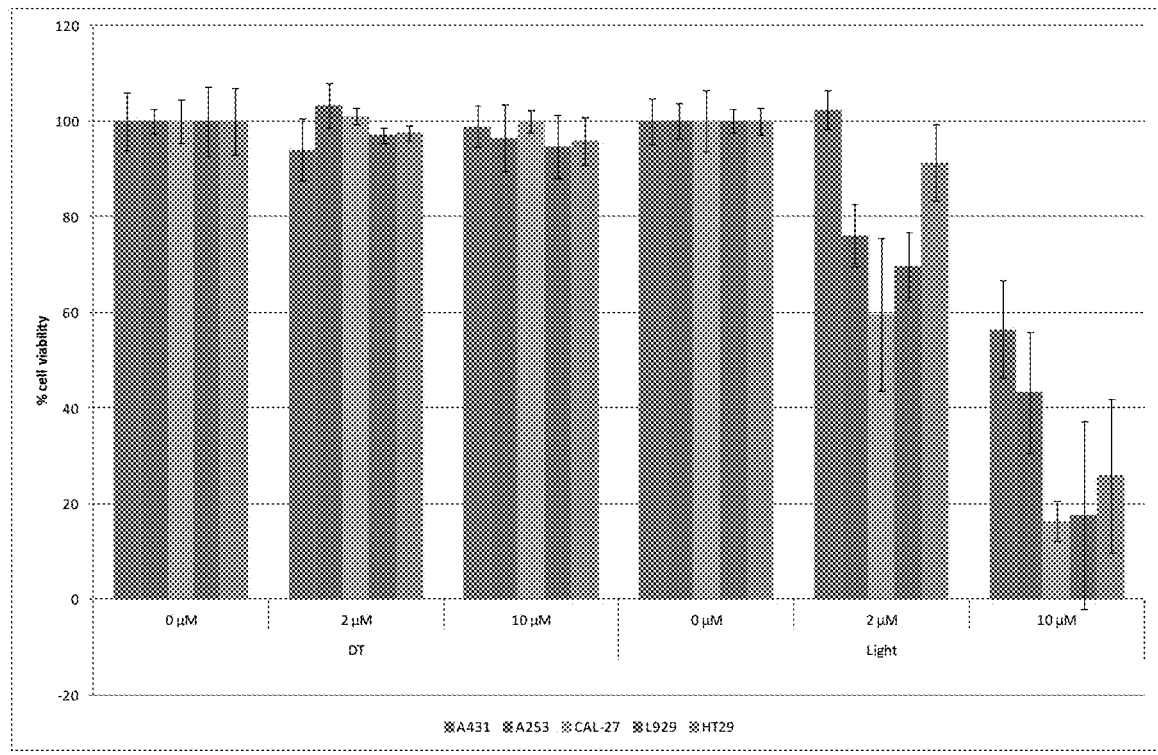
FIG. 9 shows the cell toxicity test of one embodiment of present disclosure (conjugate MS109a/BLC 3171) after 24 h incubation and irradiation with white light source.

FIG. 9 shows the cell toxicity test of conjugate MS109a/BLC 3171 after 24 h incubation and irradiation with white light source.

3.2 Phototoxicity Testing Against Bacteria

The organisms studied were two members of the microflora wounds; *Staphylococcus aureus* DSM 11729, Gram-positive; and *Pseudomonas aeruginosa* DSM 1117, Gram-negative.

Cultures cells are suspended in sterile phosphate-buffered saline (PBS) or sterile PBS supplemented with 10% sterile horse blood serum. The final OD (Optical Density) at 600 nm, 1 cm in all cases was 0.03. The bacterial suspensions are placed into sterile black well plates with clear bottoms. Concentrations of photosensitizer used in the study were as follows: 100 µM, 10 µM and 1 µM.

After an incubation time period of 90 minutes, the samples are exposed to laser light of 652 nm, power set 0.5 W, and irradiation time of 85 s. With the irradiation time, the resulting energy fluency is of about 100 J/cm². Control plates contained no photosensitizer and are not exposed to laser light. The control samples for dark toxicity are only exposed to photosensitizer without any illumination.

After irradiation, the samples are removed and suspended again in the culture media. The numbers of colony-forming units (CFU/ml) are enumerated after an adequate incubation time period.

Figure 10:
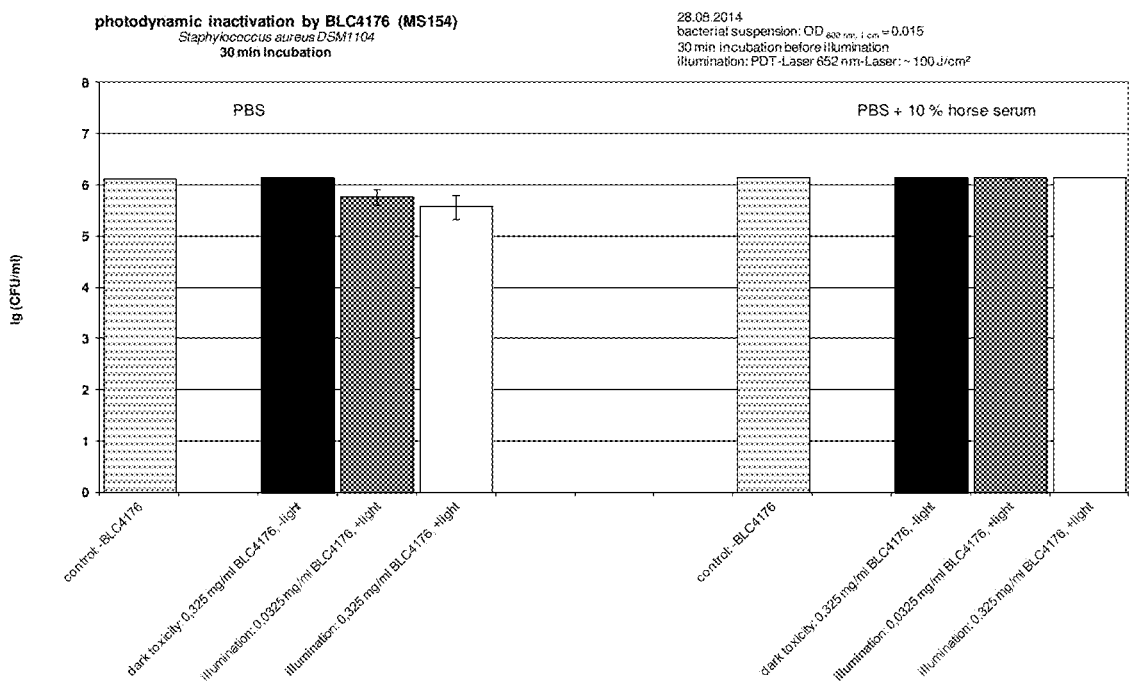
FIG. 10 shows the antibacterial phototoxicity testing of one embodiment of present disclosure (conjugate MS154/BLC 4176).

3.2.1 Testing of porphyrinoid-polymer-conjugate (2-(2-Methoxy-4-(3-((5a8,6R,6aR)-6-(((((6-((2,3,5,6-tetrafluoro-4-(10,15,20-tris(3-hydroxyphenyl)-porphyrin-5-yl)phenyl)amino)hexyl)carbamoyl)oxy) methyl)-5,5a,6,6a,7,8-hexa-hydrocyclopropa[5,6] cyclooctal[1,2-d][1,2,3]triazol-1(4H)-yl)propoxy) phenyl)-1,3-dioxolan-4-yl)-hPG9.1 with 6 Porphyrin Groups (See Example 1.11) Against Bacteria FIG. 10 shows the antibacterial phototoxicity testing of conjugate MS154/BLC 4176.

Figure 11:
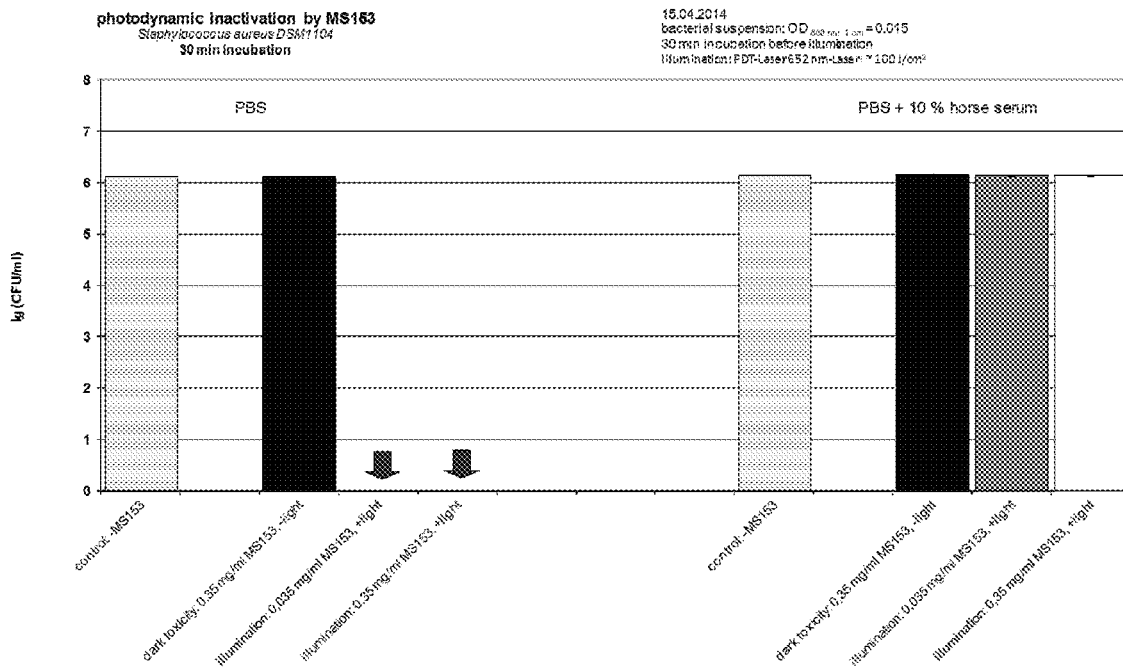
FIG. 11 shows the antibacterial phototoxicity testing of one embodiment of present disclosure (conjugate MS153/BLC 4161).

3.2.2 Testing of porphyrinoid-polymer-conjugate 5,10,15-Tris(3-hydroxyphenyl)-20-[4-((2(2-(((((1R, 8S,9s)-bicyclo[6.1.0]non-4-yn-9-yl)methoxy)-carbonyl)₋ amino)ethyl)disulfanyl)₋ ethyl)amino)₋ tetrafluorophenyl]-porphyrin-hPG19.5-mannose-azide with 6.3% Porphyrin, 38% Mannose and 35.7% Azide Groups (See Example 1.15) Against Bacteria FIG. 11 shows the antibacterial phototoxicity testing of conjugate MS153/BLC 4161.

Figure 12:
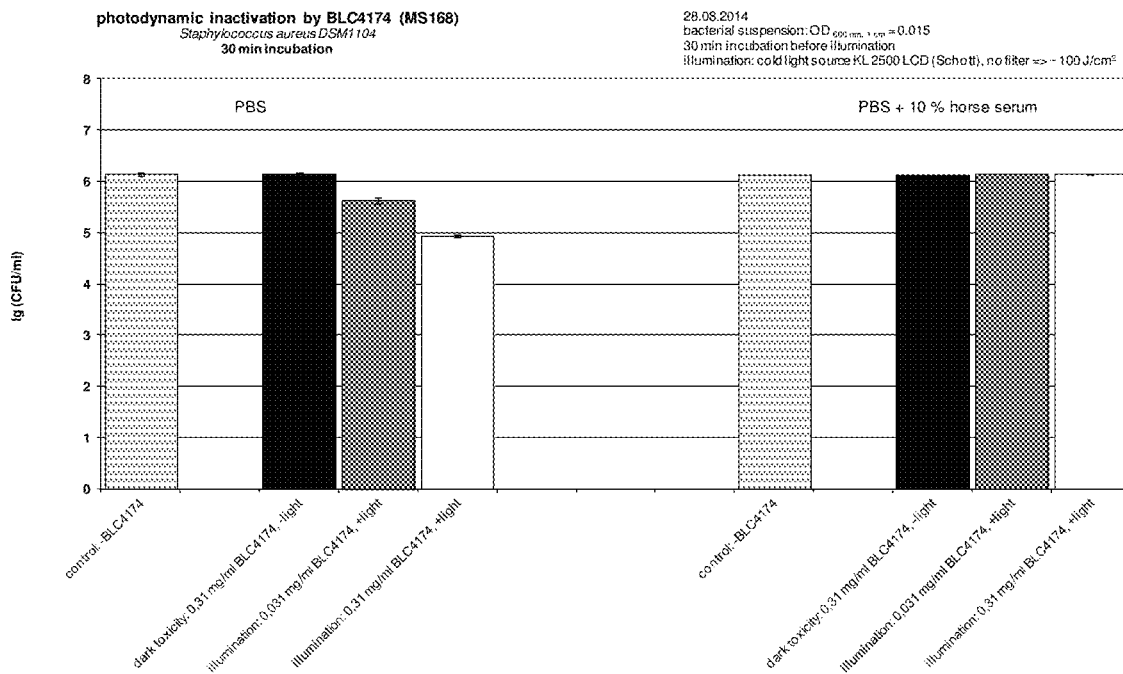
FIG. 12 shows the antibacterial phototoxicity testing of one embodiment of present disclosure (conjugate MS168/BLC 4174).

3.2.3 Testing of porphyrinoid-polymer-conjugate {5,10,15-Tris(3-hydroxyphenyl)-20-[4-(N-(1H-1,2, 3-triazol-4-yl))₋ amino)₋ tetra₋ fluoro-phenyl]₋ porphyrinato}-zinc(II)-hPG3.7-mannose with 6.4% Porphyrins, 28.0% Mannose and 30.6% Azides (See Example 1.29) Against Bacteria FIG. 12 shows the antibacterial phototoxicity testing of conjugate MS168/BLC 4174.

Figure 13:
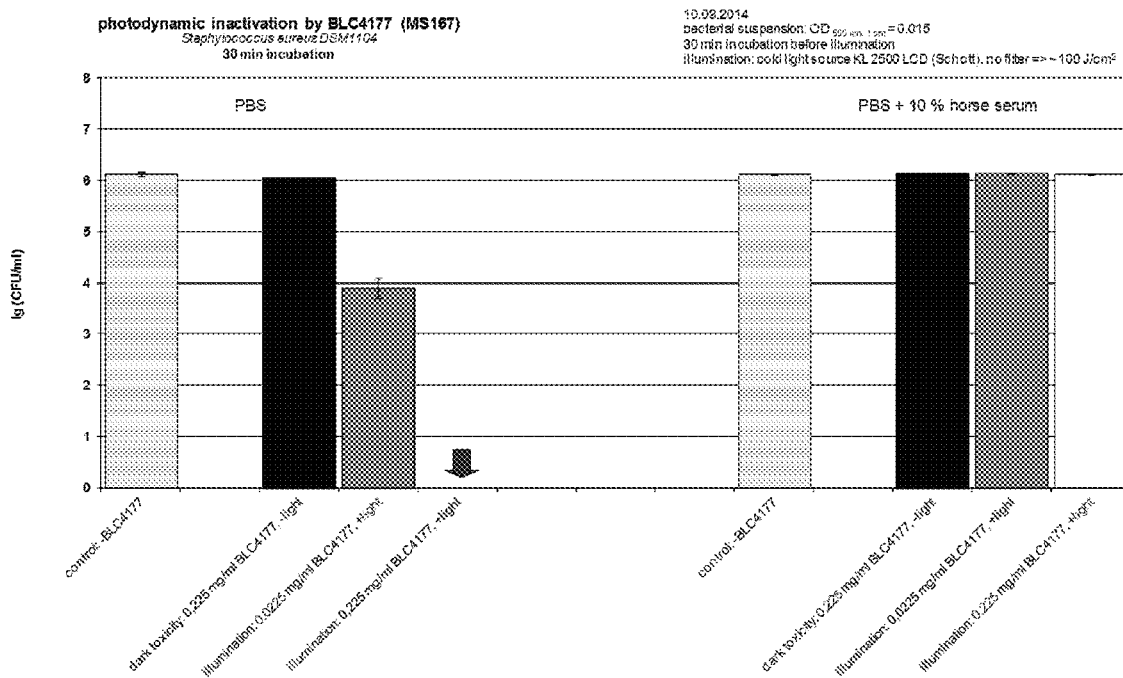
FIG. 13 shows the antibacterial phototoxicity testing of one embodiment of present disclosure (conjugate MS167/BLC 4177).

3.2.4 Testing of porphyrinoid-polymer-conjugate {5,10,15-Tris(3-hydroxyphenyl)-20[4-(N-(1H-1,2,3-triazol-4-yl))₋ amino)₋ tetra₋ fluoro-phenyl]₋ porphyrinato}-zinc(II)-hPG9.8-mannose with 10.0% Porphyrins, 28.7% Mannose and 26.3% Azides (See Example 1.30) Against Bacteria FIG. 13 shows the antibacterial phototoxicity testing of conjugate MS167/BLC 4177.

Figure 14:
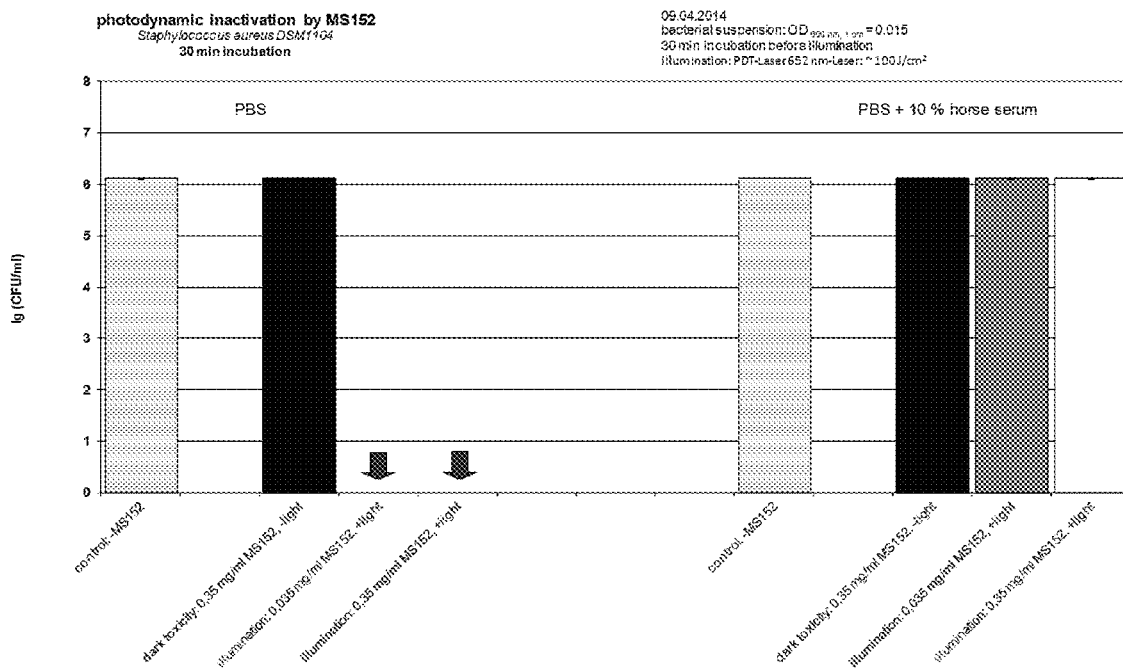
FIG. 14 shows the antibacterial phototoxicity testing of one embodiment of present disclosure (conjugate MS152/BLC 4163).

3.2.5 Testing of porphyrinoid-polymer-conjugate 5,10,15-Tris(3-hydroxyphenyl)-20-[4-((6-(((((1R,8 S,9s)-bicyclo[6.1.0]non-4-yn-9-yl)methoxy)carbonyl)amino)hexyl)-amino)₋ tetrafluorophenyl]₋ porphyrin-hPG19.5-mannose-azide with 7.2% Porphyrin, 38.0% Mannose and 34.8% Azide Groups (See Example 1.32) Against Bacteria FIG. 14 shows the antibacterial phototoxicity testing of conjugate MS152/BLC 4163.

Figure 15:
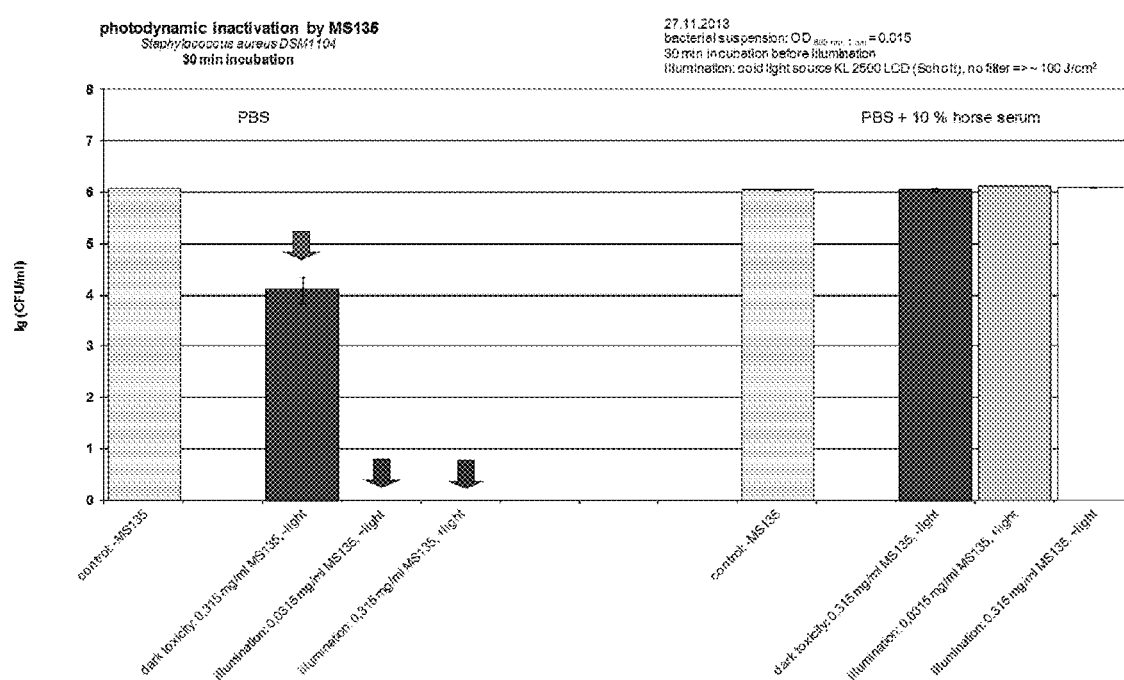
FIG. 15 shows the antibacterial phototoxicity testing of one embodiment of present disclosure (conjugate MS135/BLC 3175).

3.2.6 Testing of porphyrinoid-polymer-conjugate {5,10,15-Tris(3-hydroxyphenyl)-20-[4-(N-(1H-1,2, 3-triazol-4-yl))amino)tetrafluorophenyl]porphyrinato}-zinc(II)-hPG$_{19.5}$-mannose with 7.2% Porphyrins, 34.1% Mannose and 24.7% Azides (See Example 1.31) Against Bacteria FIG. 15 shows the antibacterial phototoxicity testing of conjugate MS135/BLC 3175.

Having described preferred embodiments of the invention with reference to the accompanying examples, it is to be understood that the invention is not limited to the precise embodiments, and that various changes and modifications may be effected therein by skilled in the art without departing from the scope of the invention as defined in the appended claims.

REFERENCES

[1] B. W. Henderson y T. J. Dougherty, Photodynamic therapy, basic principles and clinical applications, New York: Marcel Dekker, 1992.

[2] A. P. Castano, T. N. Demidova y M. R. Hamblin, «Mechanisms in photodynamic therapy: part one photosensitizers, photochemistry and cellular localization,» *Photodiagn. Photodyn. Ther.*, vol. 1, 279-293, 2004.

[3] J. G. Moser, Photodynamic tumor therapy. 2nd and 3rd generation photosensitizers, Amsterdam: Harwood Academic Publishers, 1998.

[4] M. S. Senge, J. C. Brandt, «Temoporfin (Foscan, 5,10, 15,20-Tetra(m-hydroxyphenyl)chlorin)—A Second-generation Photosensitizer,» *Photochem. Photobiol.*, vol. 87, 1240-1296, 2011.

[5] Y. Matsumura, H. Maeda, «A new concept for macromolecular therapeutics in cancer chemotherapy: mechanism of tumoritropic accumulation of proteins and the antitumor agent smancs,» *Cancer Res.*, vol. 46, 6387-6392, 1986.

[6] H. Maeda, J. Wu, T. Sawa, Y. Matsumura, K. Hori, «Tumor vascular permeability and the EPR effect in macromolecular therapeutics: a review,» *J. Contr. Rel.*, vol. 65, 271-284, 2000.

[7] S. Hackbarth, V. Horneffer, A. Wiehe, F. Hillenkamp, B. Röder, «Photophysical properties of pheophorbide-a-substituted diaminobutane poly-propylene-imine dendrimer,» *Chem. Phys.*, vol. 269, 339-346, 2001.

[8] J. S. Lindsey, I. C. Schreiman, H. C. Hsu, P. C. Kearney and A. M. Marguerettaz, «Rothemund and Adler-Longo Reactions Revisited: Synthesis of Tetraphenylporphyrins under Equilibrium Conditions,» *J. Org. Chem.*, vol 52, 827-836, 1987.

[9] R. Bonnett, R. D. White, U.-J. Winfield y M. C. Berenbaum, «Hydroporphyrins of the meso-tetra(hydroxyphenyl)porphyrin series as tumor photosensitizers,» *Biochem. J.*, vol. 261, 277-280, 1989.

[10] D. Aicher, S. Gräfe, C. B. W. Stark y A. Wiehe, «Synthesis of β-functionalized Temoporfin derivatives for an application in photodynamic therapy», *Bioorg. Med. Chem. Lett.*, no. 21, p. 5808-5811, 2011.

[11] S. K. De, R. A. Gibbs, «Ruthenium(III) chloride-catalyzed chemoselective synthesis of acetals from aldehydes», *Tetrahedron Lett.* 2004, vol. 45, issue 44, p. 8141-8144.

[12] M. R. Patel, A. Bhatt, J. D. Steffen, A. Chergui, J. Mural, Y. Pommier, J. M. Pascal, L. D. Trombetta, F. R. Fronczek, T. T. Talele, «Discovery and structure-activity relationship of novel 2,3-dihydrobenzofuran-7-carboxamide and 2,3-dihydrobenzofuran-3(2H)-one-7-carboxamide derivatives as poly(ADP-ribose)polymerase-1 inhibitors», *J. Med. Chem.* 2014, 57(13), 5579-5601.

[13] J. Dommerholt, S. Schmidt, R. Temming, L. J. A. Hendriks, F. P. J. T Rutjes, J. C. M. van Hest, D. J. Lefeber, P. Friedl, F. L. van Delft, «Readily Accessible Bicyclononynes for Bioorthogonal Labeling and Three-Dimensional Imaging of Living Cells», *Angew. Chem. Int. Ed.* 2010, 49, 9422-9425.

[14] D. Steinhilber, T. Rossow, S. Wedepohl, F. Paulus, S. Seiffert, R. Haag, «A Microgel Construction Kit for Bioorthogonal Encapsulation and pH-Controlled Release of Living Cells», *Angewandte Chemie Int. Ed.* 2013, 52, 13538-13543.

[15] I. Papp, J. Dernedde, S. Enders, S. B. Riese, T. C. Shiao, R. Roy, R. Haag, «Multivalent presentation of mannose on hyperbranched polyglycerol and their interaction with concanavalin A lectin», *ChemBioChem* 2011, 12, 1075-1083.

[16] S. Roller, H. Zhou, R. Haag, «High-loading polyglycerol supported reagents for Mitsunobu- and acylation- reactions and other useful polyglycerol derivatives», *Molecular Diversity* 2005,9, 305-316.

[17] H. R. A. Golf, H.-U. Reis sig, A. Wiehe, «Regioselective Nucleophilic Aromatic Substitution Reaction of meso-Pentafluorophenyl-Substituted Porphyrinoids with Alcohols», *Eur. J. Org. Chem.* 2015, 2015, 1548-1568.

What is claimed is:

1. A tetrapyrrolic compound of the formulas 1, 2, 3, 4, 5 or 6:

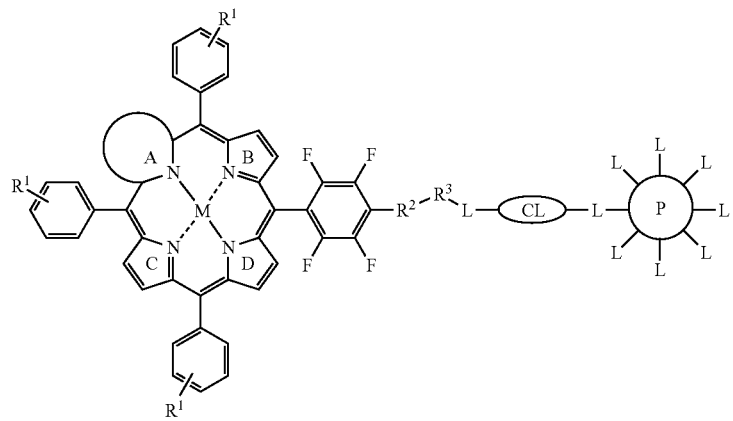

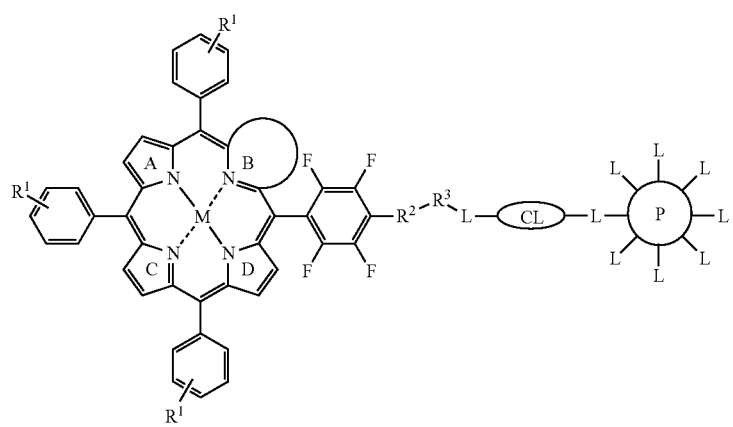

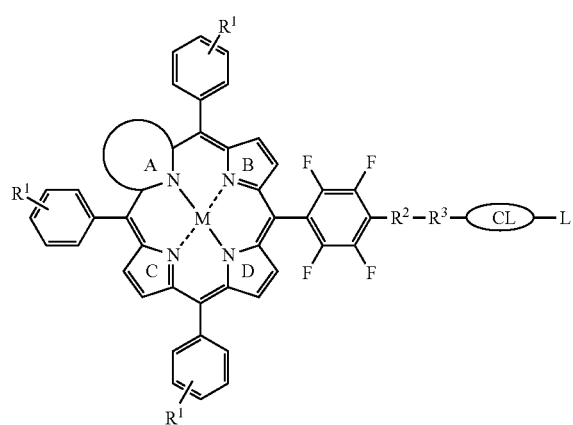

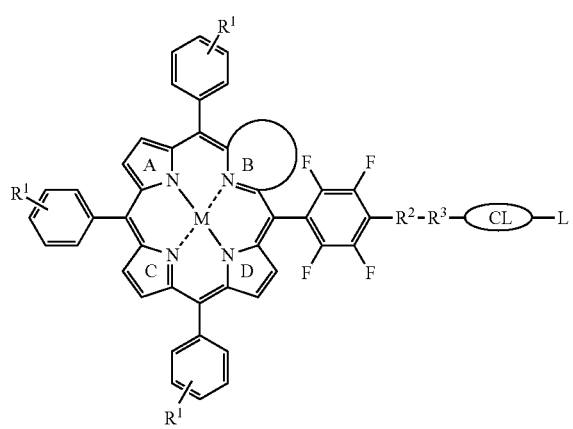

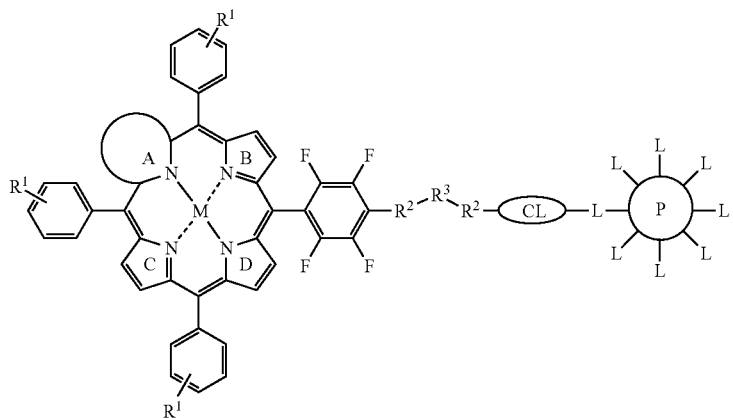

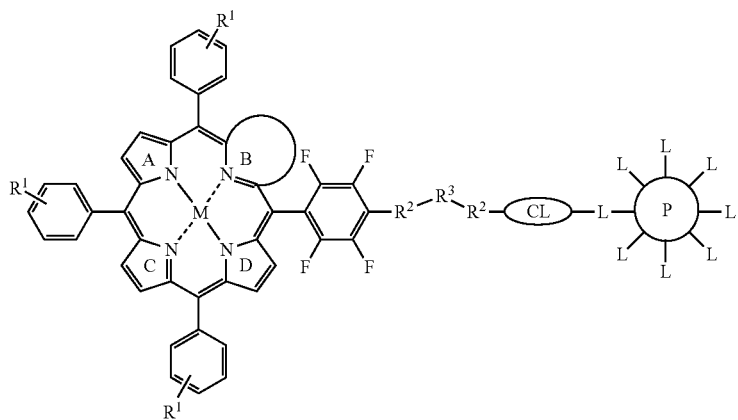

wherein:
A and B are selected from the group consisting of:

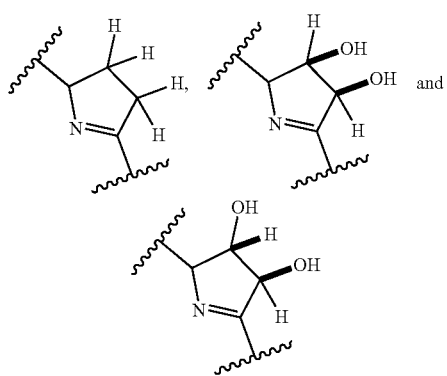

$R^2$ is —O—, —NH— or —S—;
$R^3$ is a substituted or unsubstituted alkyl group or fluoroalkyl group consisting of 1-15 carbon atoms;
M is Zn, Cu, Fe, Co, or Pd forming a metallated tetrapyrrole or void forming a metal-free tetrapyrrole;
CL is a cleavable linker based on disulfide, acetal, ester or imine;
L is selected from the group consisting of a functional group; a targeting group based on carbohydrates, an antibody, a protein, an oligopeptide, an oligonucleotide or a vitamin;
wherein the functional group is based on maleimide, cyclooctyne, alkyne, alkene, amine, carboxylic acid, hydroxyl, thiol, azide or acid chloride;
wherein the targeting group is based on carbohydrates selected from the group consisting of mannose, mannose-6-phosphate, and galactose;
wherein the antibody is selected from the group consisting of IgG, IgA, IgM, IgD, and IgE antibodies;
wherein the proteins is transferrin;
wherein the oligopeptides is selected from the group consisting of cyclic and acyclic RGD-containing oligopeptides,
wherein the oligonucleotide is an aptamer;
wherein the vitamins is a folate;
P is a polymeric structure selected from the group consisting of hyperbranched polyglycerol (hPG), poly-ε-caprolactone (PCL), polylactic acid (PLA), polybutyl cyanoacrylate (PBCA), polyhexyl cyanoacrylate (PHCA), polystyrene (PS) and poly(methyl methacrylate) (PMMA);
$R^1$ is a substituent either in the meta- or para-position of the phenyl ring selected from the group consisting of —OH, —COOH, —NH$_2$, —COOX, —NHX, OX, —NH—Y—COOH, and —CO—Y—NH$_2$; wherein X is a polyethyleneglycol-residue with $(CH_2CH_2O)_nCH_3$ with n=1-30 or a carbohydrate moiety; and Y is peptides or oligopeptides wherein n=1-30; and wherein —CL- may optionally be a covalent bond in compounds of formula 3 or 4.

2. The tetrapyrrolic compound according to claim 1 having the formulas 3, or 4 wherein —CL- is omitted and replaced by a covalent bond in formulas 3 and 4.

3. The tetrapyrrolic compound according to claim 1, the formulas 1, 2, 3, 4, 5 or 6, wherein $R^2$, $R^3$, M, CL and P are as defined in claim 1; L is a functional group based on maleimide, cyclooctyne, alkyne, alkene, amine, carboxylic acid, hydroxyl or azide/targeting group based on a carbohydrate selected from mannose, mannose-6-phosphate, galactose, an antibody selected from IgG, IgA, IgM, IgD, IgE antibodies, transferrin or an oligopeptide selected from cyclic and acyclic RGD-containing oligopeptides; and $R^1$ is a substituent either in the meta- or para-position of the phenyl ring with $R^1$=—OH, —COOH or —NH$_2$.

4. The tetrapyrrolic compound according to claim 3 having the formulas 3, or 4 wherein —CL- is omitted and replaced by a covalent bond in formulas 3 and 4.

5. The tetrapyrrolic compound according to claim 4, having the formula:

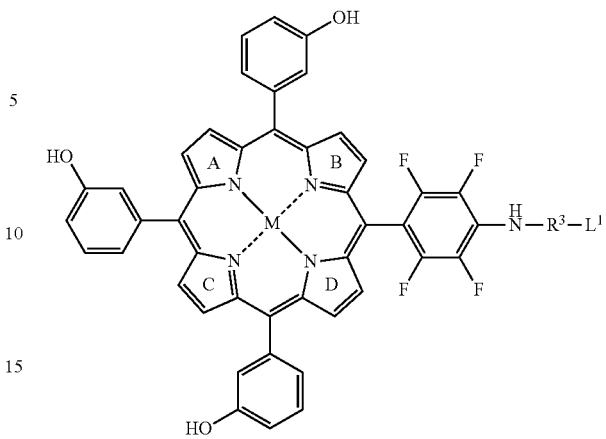

wherein $R^3$ is an unsubstituted alkyl group consisting of 1 or 6 carbon atoms; M is Zn forming a metallated porphyrin or void forming a metal-free porphyrin; and $L^1$ is a functional group based on cyclooctyne or alkyne.

6. The tetrapyrrolic compound according to claim 4, having the formula:

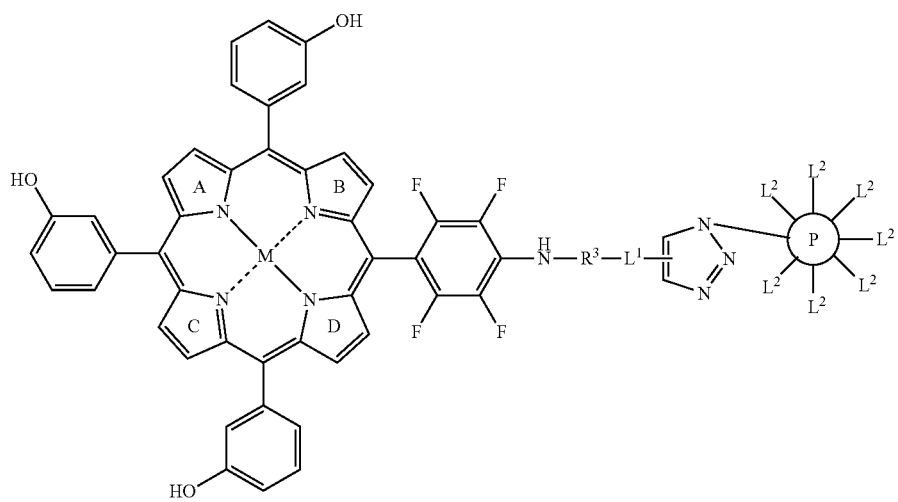

wherein M is Zn forming a metallated porphyrin or void forming a metal-free porphyrin; $R^3$ is an unsubstituted alkyl group consisting of 1 or 6 carbon atoms; $L^1$ is a functional group based on cyclooctyne or alkyne; $L^2$ is a functional group based on azide/targeting group based on mannose; P is hyperbranched polyglycerol (hPG).

7. The tetrapyrrolic compound according to claim 4, having the formula selected from the group consisting of:
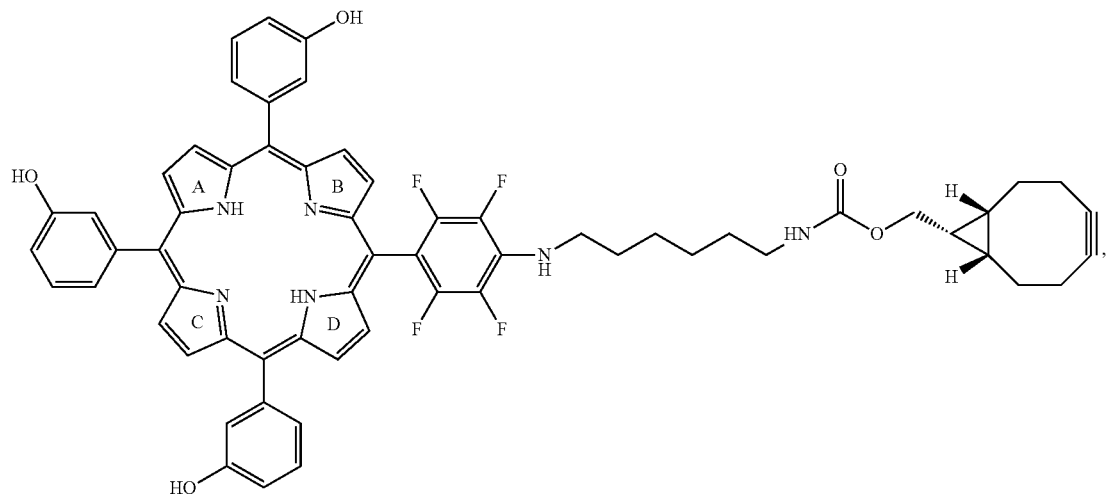
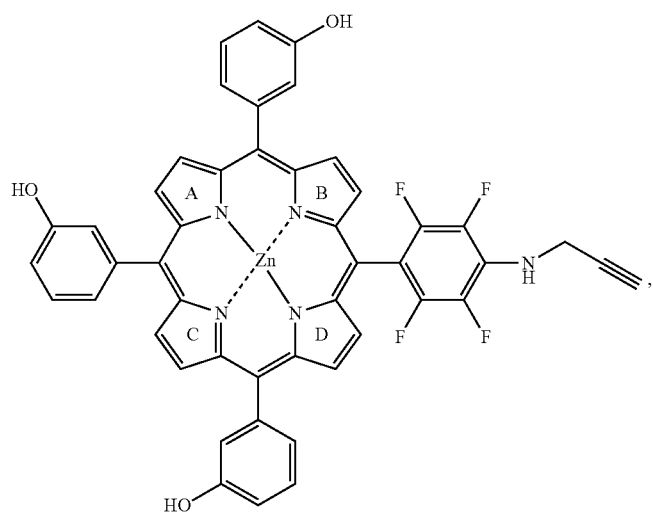
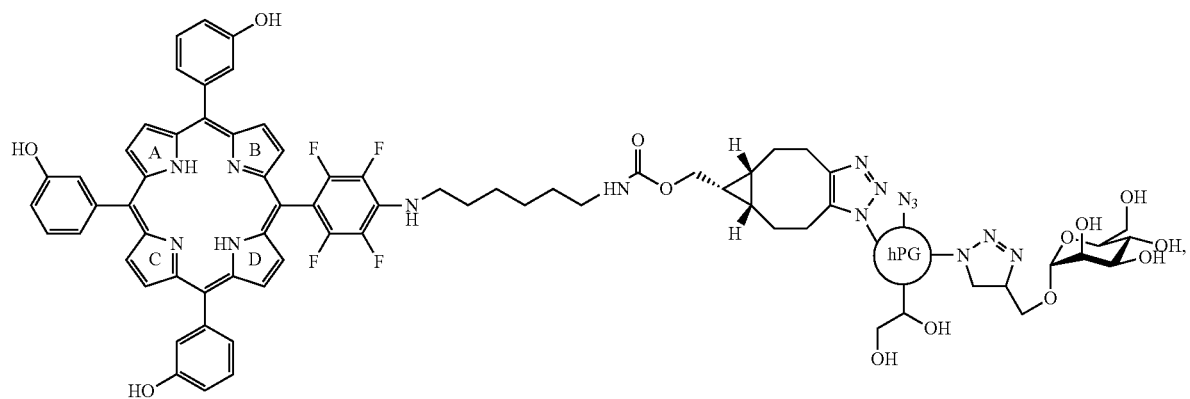

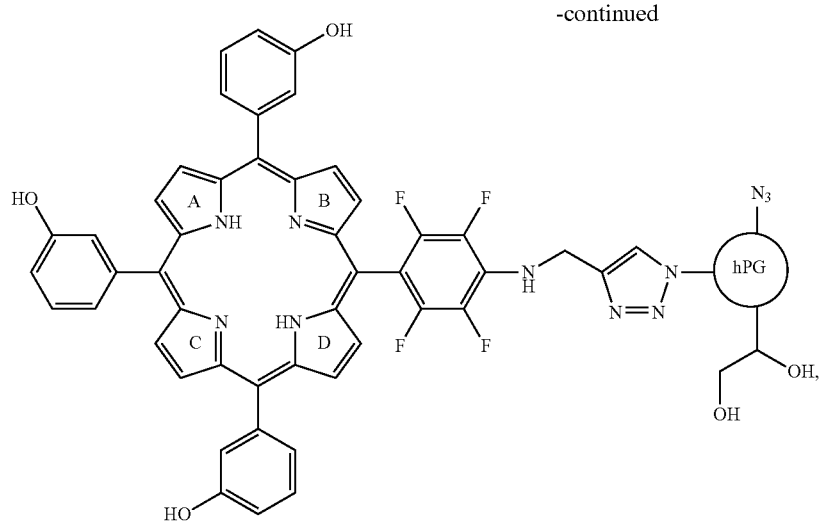
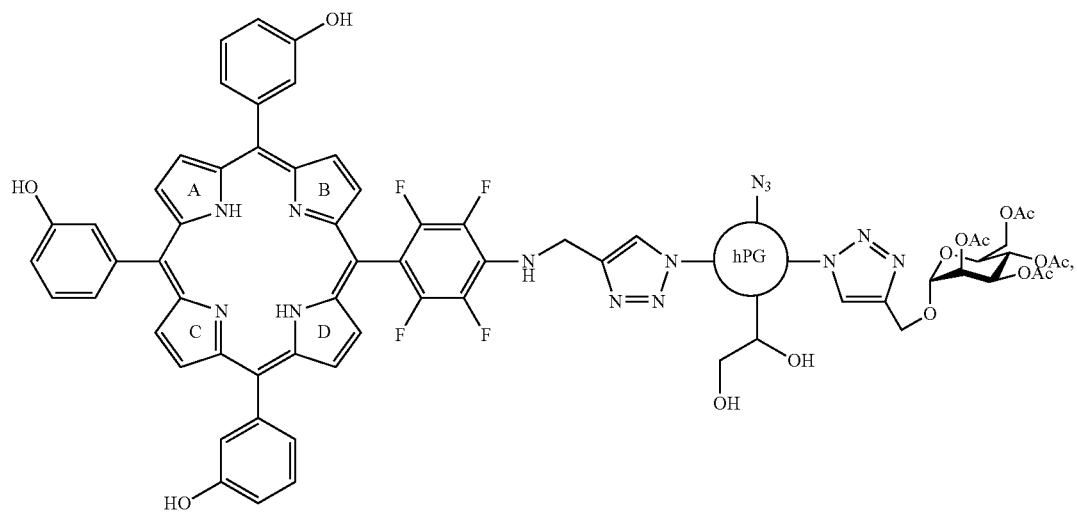
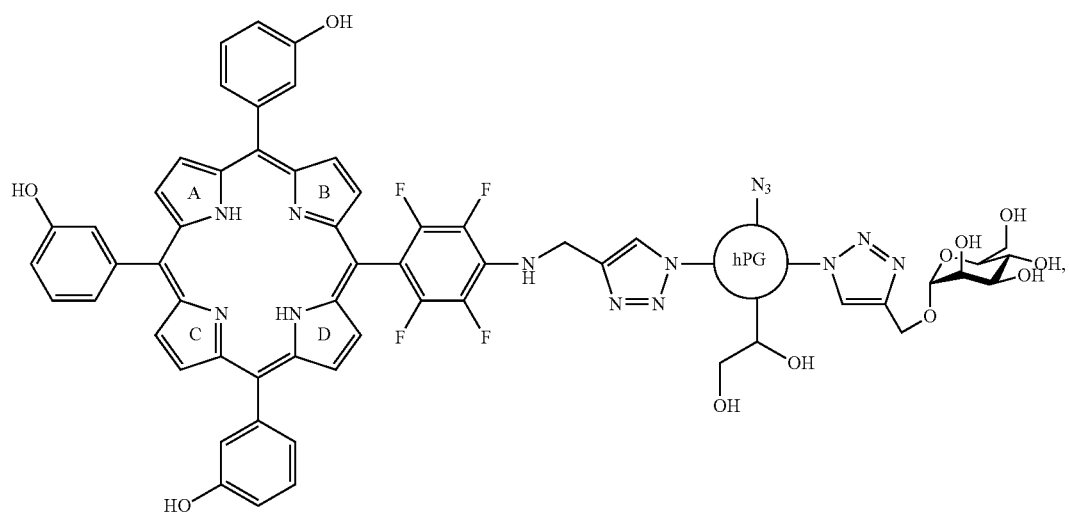
and
a pharmaceutically acceptable derivative thereof.

8. A tetrapyrrolic compound having the formula:

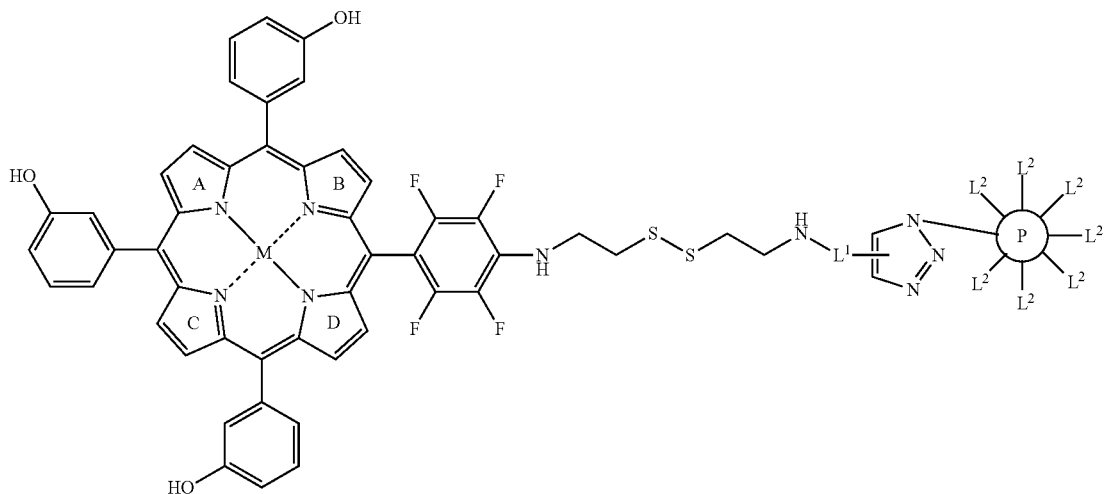

wherein M is Zn forming a metallated porphyrin or void forming a metal-free porphyrin; $L^1$ is a functional group based on cyclooctyne or alkyne; $L^2$ is a functional group based on azide/targeting group based on mannose; and P is an hyperbranched polyglycerol (hPG).

9. A tetrapyrrolic compound having the formula selected from the group consisting of

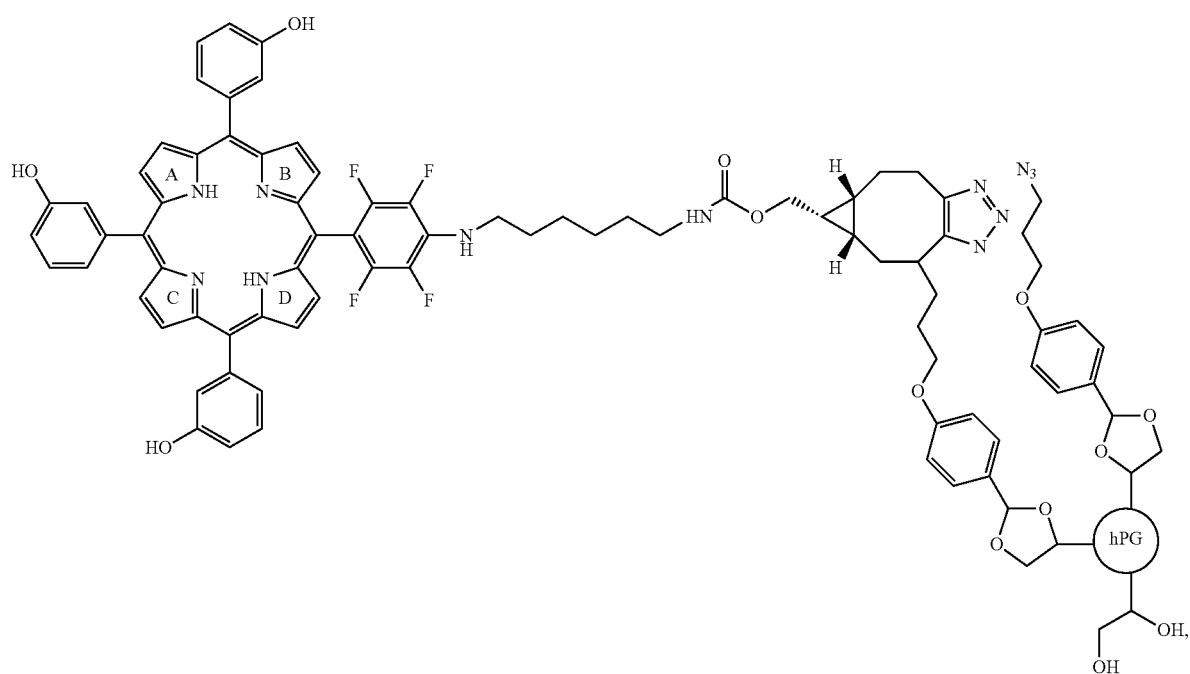

65
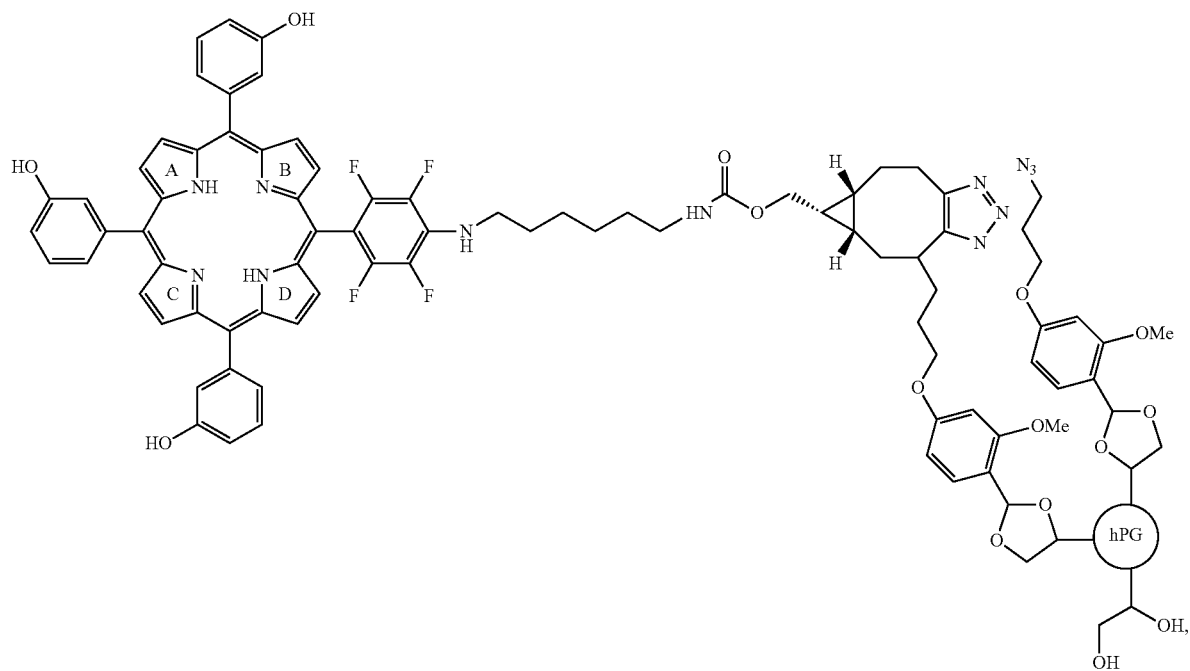
-continued
66
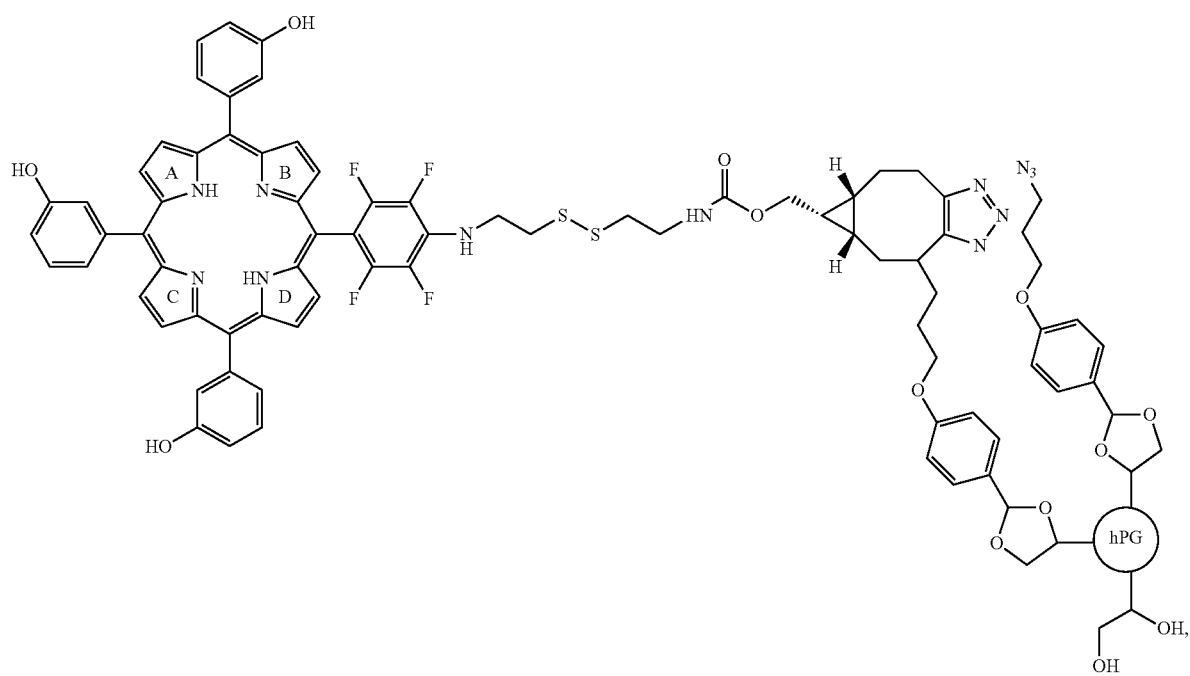

-continued
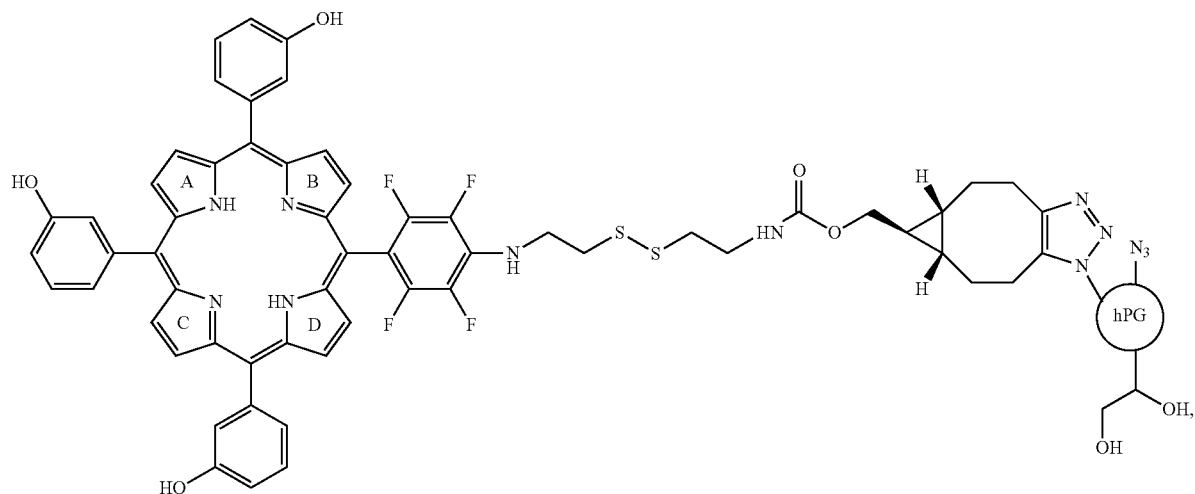
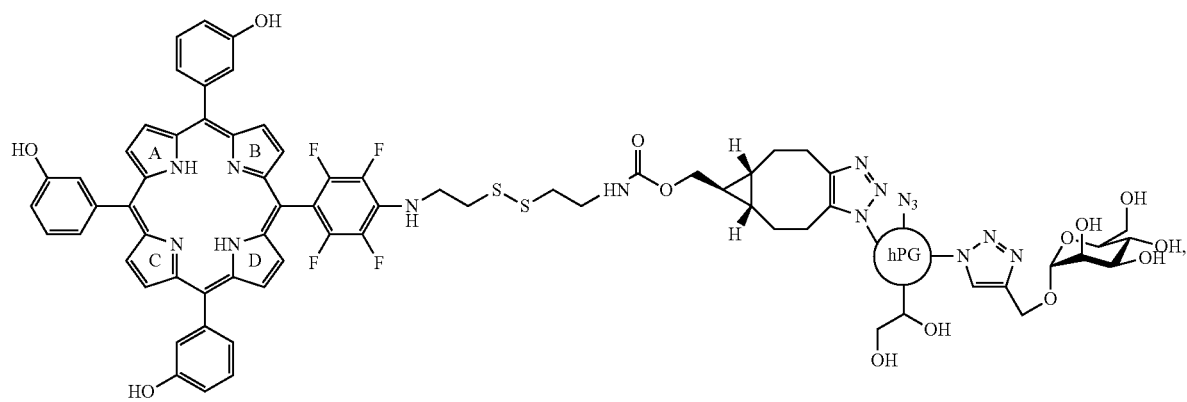
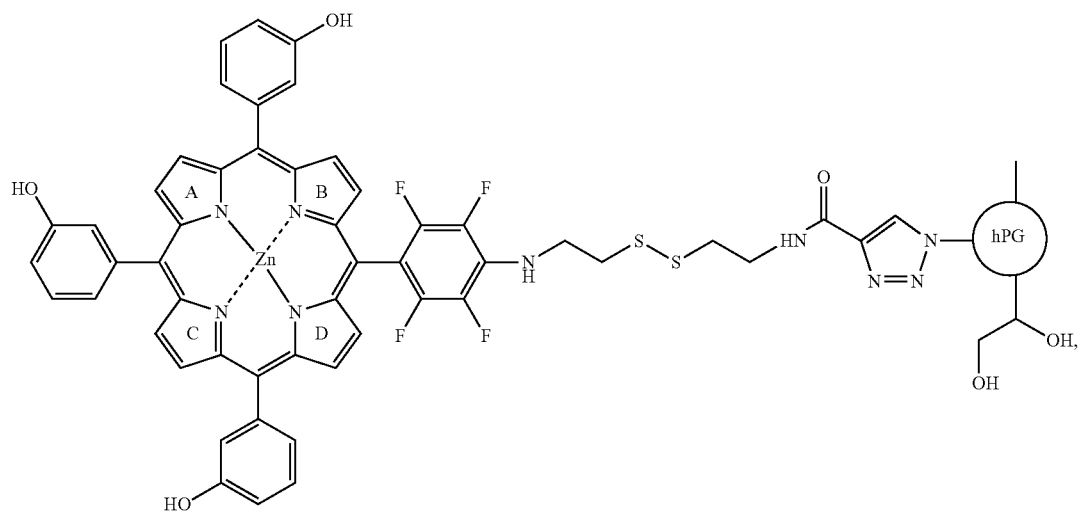

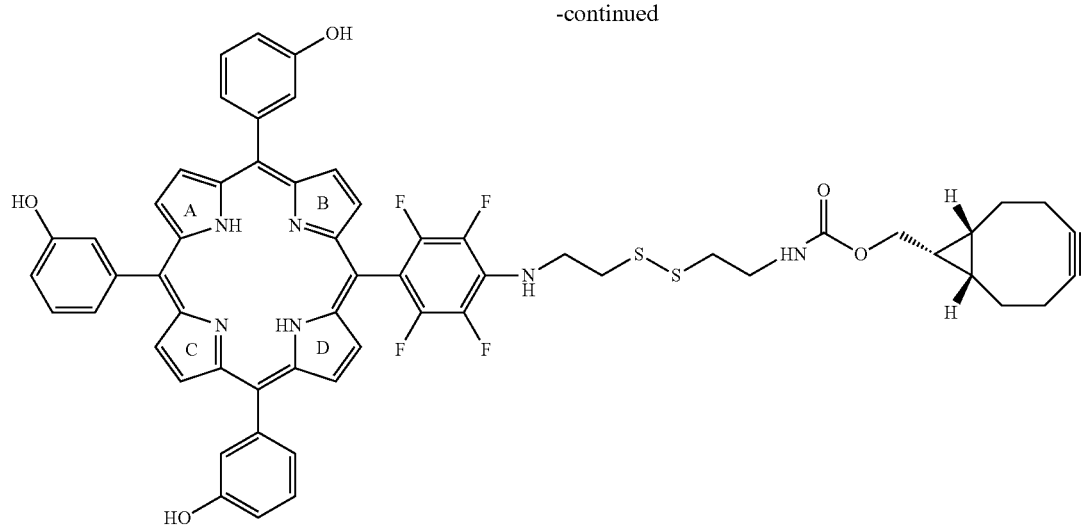
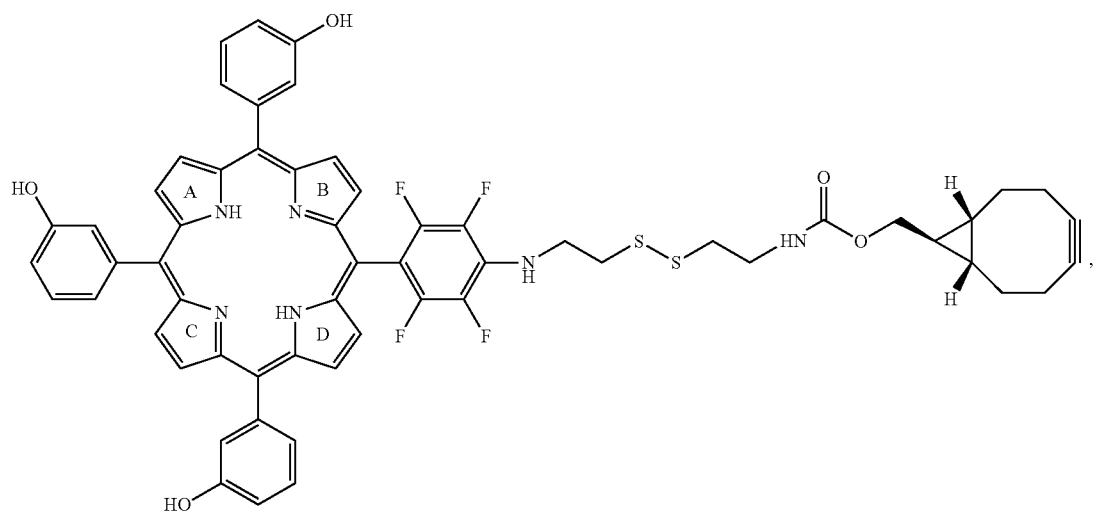
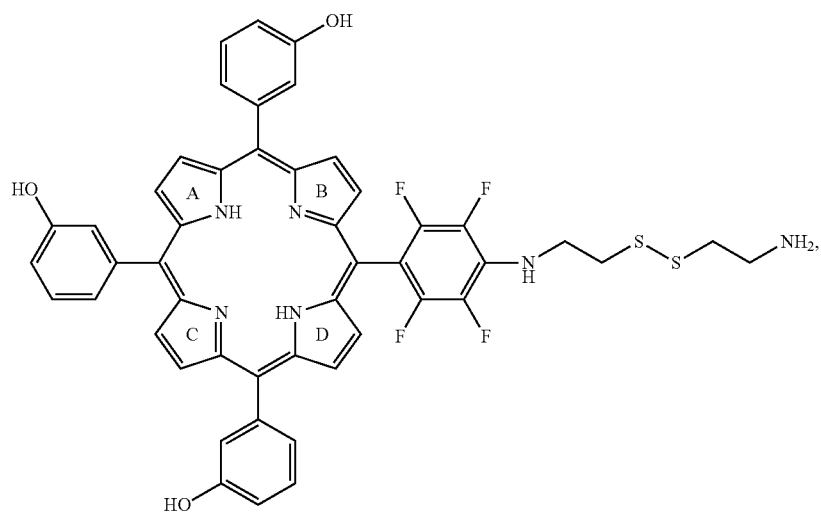

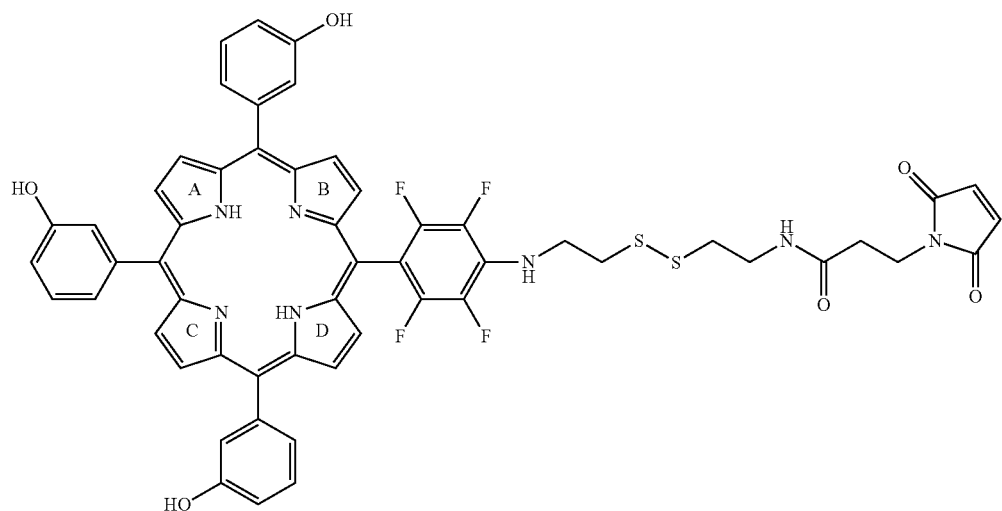
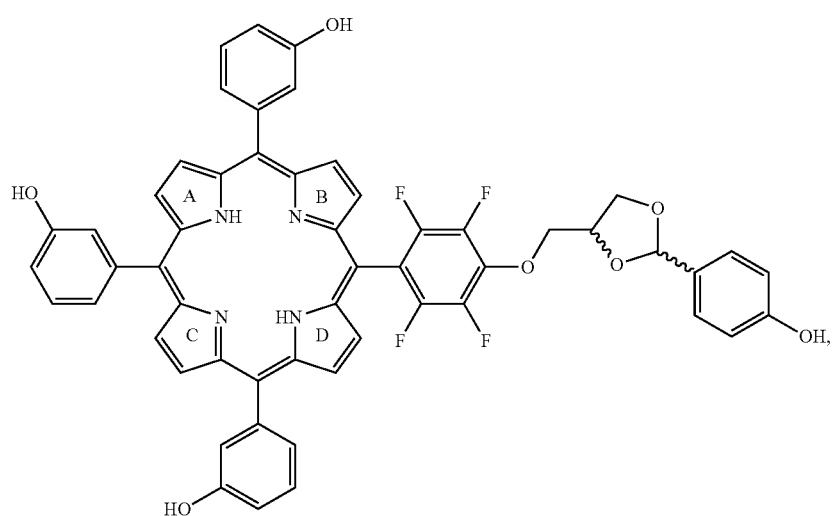
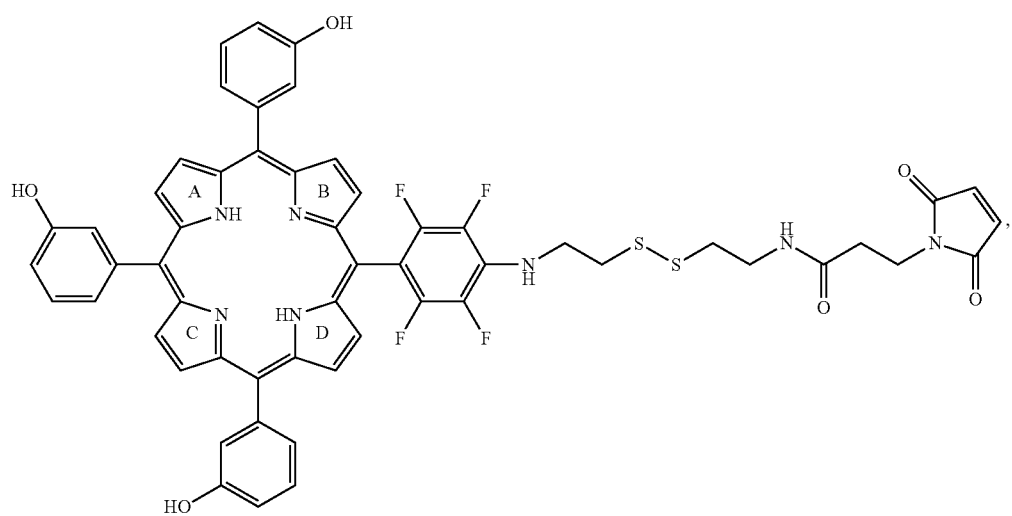

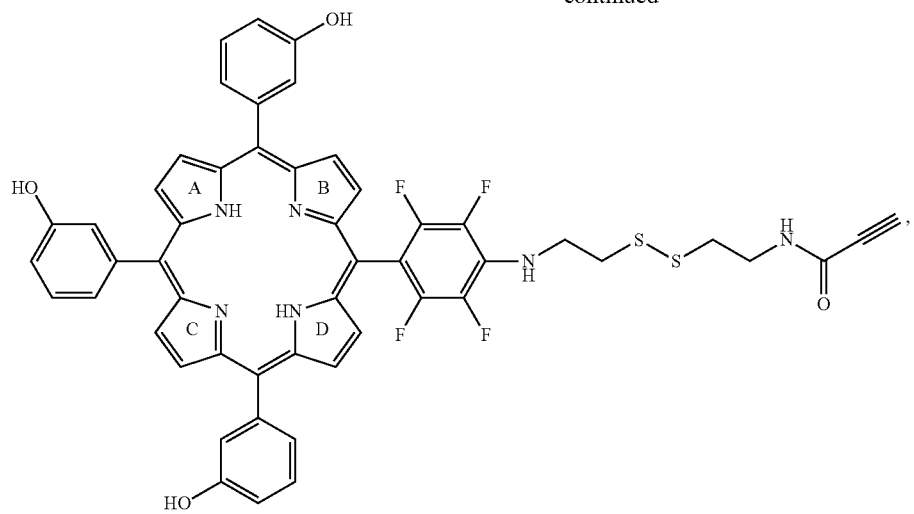
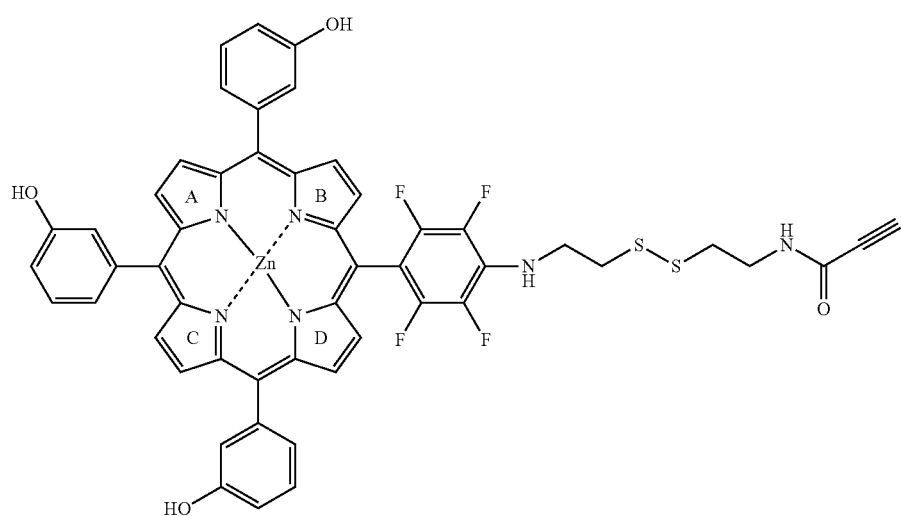
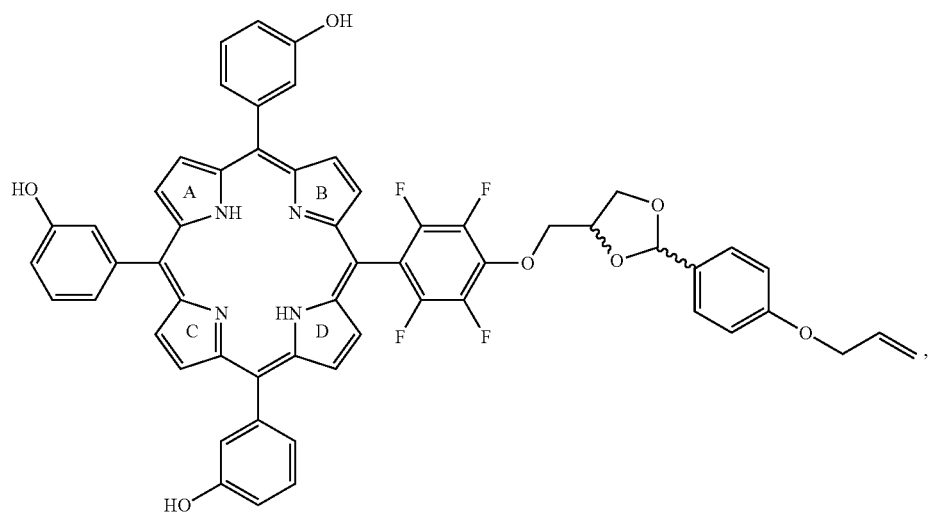

-continued

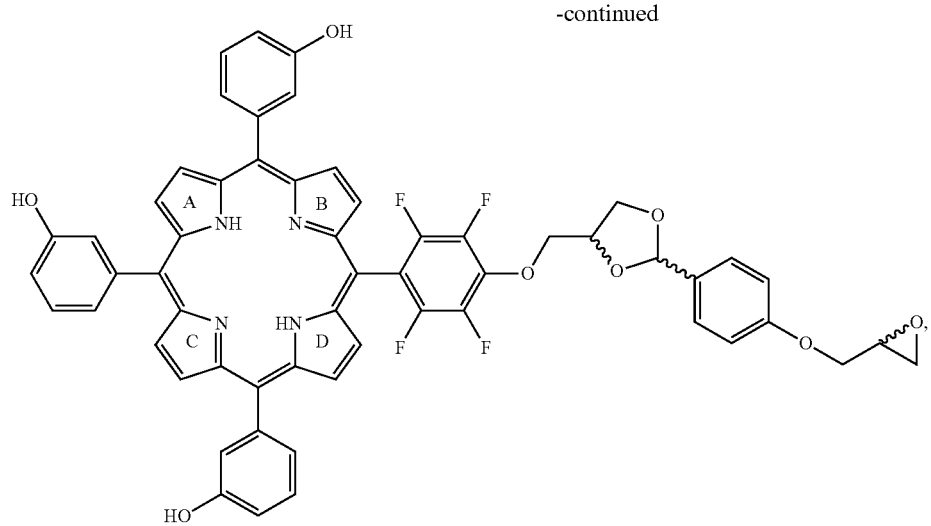

and
a pharmaceutically acceptable derivative thereof.

10. The compound of claim 1 for use in photodynamic therapy in the treatment of tumors, dermatological disorders, viral or bacterial infections, opthalmological disorders or urological disorders; arthritis and similar inflammatory diseases; or in the diagnosis of tumorous diseases, arthritis and similar inflammatory diseases.

11. A pharmaceutical composition comprising a compound according to claim 1 as an active ingredient.

12. The pharmaceutical composition according to claim 11, wherein said compound is conjugated to a targeting agent.

13. The pharmaceutical composition according to claim 12, wherein said targeting agent is selected from the group consisting of an antibody, a fragment of an antibody and a peptide.

* * * * *